United States Patent
Bertolotti et al.

(10) Patent No.: US 11,331,286 B2
(45) Date of Patent: May 17, 2022

(54) INHIBITORS AND THEIR USES

(71) Applicant: Medical Research Council, Swindon (GB)

(72) Inventors: Anne Bertolotti, Cambridge (GB); Indrajit Das, Cambridge (GB); Agnieszka Krzyzosiak, Cambridge (GB); Adrien Rousseau, Cambridge (GB); Kim Schneider, Cambridge (GB); Anna Gudny Sigurdardottir, Cambridge (GB)

(73) Assignee: United Kingdom Research and Innovation, Swindon (GB)

( * ) Notice: Subject to any disclaimer, the term of this patent is extended or adjusted under 35 U.S.C. 154(b) by 52 days.

(21) Appl. No.: 16/804,402

(22) Filed: Feb. 28, 2020

(65) Prior Publication Data

US 2020/0197337 A1   Jun. 25, 2020

Related U.S. Application Data

(63) Continuation of application No. 15/564,834, filed as application No. PCT/GB2016/050991 on Apr. 8, 2016, now Pat. No. 11,154,519.

(30) Foreign Application Priority Data

Apr. 8, 2015 (GB) .................................. 1505971
Apr. 8, 2015 (GB) .................................. 1505975

(51) Int. Cl.

| | | |
|---|---|---|
| *A61K 31/155* | (2006.01) | |
| *C07C 281/18* | (2006.01) | |
| *A61P 25/28* | (2006.01) | |
| *A61P 25/14* | (2006.01) | |
| *A61P 21/00* | (2006.01) | |
| *C12Q 1/42* | (2006.01) | |
| *C07D 239/30* | (2006.01) | |
| *C07D 213/61* | (2006.01) | |
| *G01N 33/573* | (2006.01) | |
| *C12N 11/14* | (2006.01) | |
| *G01N 21/31* | (2006.01) | |
| *G01N 33/53* | (2006.01) | |

(52) U.S. Cl.
CPC ............ *A61K 31/155* (2013.01); *A61P 21/00* (2018.01); *A61P 25/14* (2018.01); *A61P 25/28* (2018.01); *C07C 281/18* (2013.01); *C07D 213/61* (2013.01); *C07D 239/30* (2013.01); *C12N 11/14* (2013.01); *C12Q 1/42* (2013.01); *G01N 21/31* (2013.01); *G01N 33/53* (2013.01); *G01N 33/573* (2013.01); *C07K 2317/92* (2013.01); *G01N 2333/916* (2013.01)

(58) Field of Classification Search
None
See application file for complete search history.

(56) References Cited

U.S. PATENT DOCUMENTS

| | | |
|---|---|---|
| 3,982,020 A | 9/1976 | Houlihan et al. |
| 4,109,008 A | 8/1978 | Cognacq et al. |
| 2005/0136444 A1 | 6/2005 | Scully et al. |
| 2009/0306430 A1 | 12/2009 | Becq et al. |

(Continued)

FOREIGN PATENT DOCUMENTS

| | | |
|---|---|---|
| DE | 2700561 A1 | 7/1977 |
| GB | 1223491 A | 2/1971 |

(Continued)

OTHER PUBLICATIONS

Tribouillard-Tanvier et al. "Antihypertensive Drug Guanabenz is Active in Vivo against both Yeast and Mammalian Prions" PLoS One, 2008, vol. 3, Issue 4, Article e1981.*
Abdulkarim, Baroj et al., "A Missense Mutation in PPP1R15B Causes a Syndrome Including Diabetes, Short Stature, and Microcephaly," *Diabetes*, vol. 64, pp. 3951-3962, 2015.
Bairwa, R. et al., Novel Molecular Hybrids of Cinnamic Acids and Guanylhydrazones as Potential Antitubercular Agents, *Bioorganic & Medicinal Chem. Lett.*, vol. 20, pp. 1623-1625, 2010.

(Continued)

*Primary Examiner* — Joseph R Kosack
(74) *Attorney, Agent, or Firm* — Bookoff McAndrews, PLLC

(57) ABSTRACT

The present invention relates to inhibitors of PPP1 R15A and PPP1 R15B and their use in therapy, particularly in the treatment of a disease state alleviated by the inhibition of PPP1 R15A and PPP1 R15B, for example a disorder associated with accumulation of misfolded proteins or proteostatsis disorder. Compounds of the invention include compounds having the formula IA or a pharmaceutically acceptable salt thereof, wherein $R^{1a}$, $R^{3a}$, $R^{5a}$, $X^a$ and $Y^a$ are as defined herein.

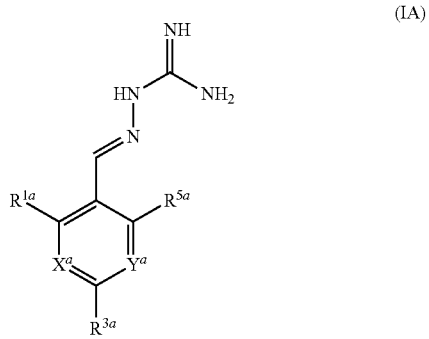

(IA)

15 Claims, 6 Drawing Sheets

(56) References Cited

U.S. PATENT DOCUMENTS

| | | | |
|---|---|---|---|
| 2018/0111896 A1 | 4/2018 | Bertolotti et al. | |
| 2018/0125801 A1 | 5/2018 | Bertolotti et al. | |
| 2020/0297668 A1* | 9/2020 | Bertolotti | C12N 11/14 |

FOREIGN PATENT DOCUMENTS

| | | |
|---|---|---|
| WO | WO 01/25192 A1 | 4/2001 |
| WO | WO 02/11715 A2 | 2/2002 |
| WO | WO 2005/031000 A2 | 4/2005 |
| WO | WO 2007/060342 A2 | 5/2007 |
| WO | WO 2008/041133 A2 | 4/2008 |
| WO | WO 2008/041134 A2 | 4/2008 |
| WO | WO 2014/108520 A1 | 7/2014 |
| WO | WO 2014/138298 | 9/2014 |
| WO | WO 2015/120446 A1 | 8/2015 |
| WO | WO 2016/001389 | 1/2016 |
| WO | WO 2016/001390 | 1/2016 |
| WO | WO 2016/162688 | 10/2016 |

OTHER PUBLICATIONS

Berge, Stephen M. et al., "Pharmaceutical Salts," *J. Pharm. Sci.*, vol. 66, pp. 1-19, 1977.
Bertolotti, Anne et al., Dynamic Interaction of BiP and ER Stress Transducers in the Unfolded-Protein Response, *Nature Cell Biology*, vol. 2, pp. 326-332, 2000.
Boens, Shannah et al., Interactor-Guided Dephosphorylation by Protein Phosphatase-1, *Phosphatase Modulators, Methods in Molecular Biology*, vol. 1053, pp. 271-281, 2013.
Bollen, Mathieu et al., "The Extended PP1 Toolkit: Designed to Create Specificity," *Trends Biochem. Sci.*, vol. 35, pp. 450-458, 2010.
Boyce, Michael et al., A Selective Inhibitor of EIF2α Dephosphorylation Protects Cells From ER Stress, *Science*, vol. 307, pp. 935-939, 2005.
CAPLUS Registry No. 849334-94-7, Hydrazinecarboximidamide, 2-[(2,3-dichlorophenyl)methylene]-hydrochloride, Apr. 27, 2005 (1 page).
CAPLUS Registry No. 94023-67-3, 2-[(2,3-Dichlorophenyl)methylene]hydrazinecarboximidamide, Sep. 8, 1985 (1 page).
Cao, Stewart Siyan et al., "Unfolded Protein Response," *Current Biology*, vol. 22, pp. R622-R626, 2012.
Chen, Ruming et al., "G-actin Provides Substrate-Specificity to Eukaryotic Initiation Factor 2α Holophosphatases," *eLife: Biochemistry, Biophysics and Structural Biology*, vol. 4, pp. 1-18, 2015.
Chen, Ting, et al., Chemical Genetics Identify eIF2α Kinase Heme Regulated Inhibitor as Anti-Cancer Target, *Nat. Chem. Biol.*, vol. 7, pp. 610-616, 2011.
Choy, Meng S. et al., Regulation of Protein Phosphatase 1 by Intrinsically Disordered Proteins, *Biochem. Soc. Trans.*, vol. 40, pp. 969-974, 2012.
Choy, Meng S., et al., "Structural and Functional Analysis of the GADD34:PP1 eIF2α Phosphatase," *Cell Rep.*, vol. 11, pp. 1885-1891, 2015.
Choy, Meng S. et al., "Understanding the Antagonism of Retinoblastoma Portein Dephosphorylation by PNUTS Provides Insights into the PP1 Regulatory Code," *Proc. Natl. Acad. Sci. USA*, vol. 111, pp. 4097-4102, 2014.
Costa-Mattioli, Mauro et al., "eIF2α Phosphorylation Bidirectionally Regulates the Switch from Short to Long-Term Synaptic Plasticity and Memory," *Cell*, vol. 129, pp. 195-206, 2007.
Das, Indrajit et al., "Preventing Proteostasis Diseases by Selective Inhibition of a Phosphatase Regulatory Subunit," *Science*, vol. 348, pp. 239-242, 2015.
Database Registry No. 849460-24-8, Hydrazinecarboximidamide, 2-[(3,5-dibromophenyl)methylene], Chemical Abstracts Services, Apr. 29, 2005.
Database Registry No. 1563208-37-6, Hydrazinecarboximidamide, 2-[(3,4,5-trifluorophenyl)methylene], Chemical Abstracts Service, Mar. 6, 2014.
Database Registry No. 1704405-00-4, Hydrazinecarboximidamide, 2-[(2,4,5-trifluorophenyl)methylene], Chemical Abstracts Service, May 14, 2015.
Donzé, Oliver et al., "Abrogation of Translation Initiation Factor eIF-2 Phosphorylatioin Causes Malignant Transformation of NIH 3T3 Cells," vol. 14, pp. 3828-3834, 1995.
Duennwald, Martin L. et al., "Impaired ERAD and ER Stress are and Specific Events in Polyglutamine Toxicity," *Genes & Development*, vol. 22, pp. 3308-3319, 2008.
Duffy, Siobain et al., "Site-Specific, Enzymatic Biotinylation of Recombinant Proteins in *Spodoptera frugiperda* Cells Using Biotin Acceptor Peptides," *Anal. Biochem.*, vol. 262, pp. 122-128, 1998.
Frostell-Karlsson, Asa et al., "Biosensor Analysis of the Interaction Between Immobilized Human Serum Albumin and Drug Compounds for Prediction of Human Serum Albumin Binding Levels," *J. Med. Chem.*, vol. 43, pp. 1986-1992, 2000.
Gardner, Thomas S. et al., "The Synthesis of Compounds for the Chemotherapy of Tuberculosis v. Some Transformations of Pyridylaldehyde Thiosemicarbazones," *J. Org. Chem.*, vol. 20, pp. 976-980, 1955.
Gilmartin, Aidan G. et al., "Allosteric Wip1 Phosphatase Inhibition Through Flap-Subdomain Interaction", *Nature Chemical Biology*, vol. 10, pp. 181-190, 2014.
Hall, Alan H. et al., "Guanabenz Overdose," *Annals of Internal Medicine*, vol. 102, pp. 787-788, 1985.
Hamamura Kazurori et al., "Salubrinal Acts as a Dusp2 Inhibitor and Suppresses Inflammation in Anti-Collagen Antibody-Induced Arthritis," *Cellular Signalling*, vol. 27, pp. 828-835, 2015.
Harding, Heather P. et al., "An Integrated Stress Response Regulates Amino Acid Metabolism and Resistance to Oxidative Stress," *Molecular Cell*, vol. 11, pp. 619-633, 2003.
Harding, Heather P. et al., "Perk is Essential for Translational Regulation and Cell Survival During the Unfolded Protein Response," *Molecular Cell*, vol. 5, pp. 897-904, 2000.
Harding, Heather P. et al., "Regulated Translation Initiation Controls Stress-Induced Gene Expression in Mammalian Cells," *Molecular Cell*, vol. 6, pp. 1099-1108, 2000.
Harding, Heather P. et al., "Ppp1r15 Gene Knockout Reveals an Essential Role for Translation Initiation Factor 2 Alpha (eIF2α) Dephosphorylation in Mammalian Development", *Proc. Nat. Acad. Sci. USA*, vol. 106, pp. 1832-1837, 2009.
Henry, Earl Webb et al., "Comparison of Trembler and Trembler-J Mouse Phenotypes: Varying Severity of Peripheral Hypomyelination," *J. Neuropathology and Experimental Neurology*, vol. 42, pp. 688-706, 1983.
Heroes, Ewald et al., "The PP1 Binding Code: A Molecular-Lego Strategy That Governs Specificity," *The FEBS Journal*, vol. 280, pp. 584-595, 2013.
Jazcilevich, S. et al., "Induction of Fatty Liver in the Rat After Cycloheximide Administration," *Laboratory Investigation*, vol. 23, pp. 590-594, 1970.
Jousse, Celine et al., "Inhibition of a Constitutive Translation Initiation Factor 2α Phosphatase, CReP, Promotes Survival of Stressed Cells," *J. Cell Biol.*, vol. 163, pp. 767-775, 2003.
Krzyzosiak et al., "Target-Based Discovery of an Inhibitor of the Regulatory Phosphatase PPP1R15B," *Cell*, vol. 174, pp. 1216-1228 (2018).
Lee, Yun-Young et al., "An Upstream Open Reading Frame Regulates Translation of GADD34 During Cellular Stresses That Induce eLF2α Phosphorylation," vol. 284, pp. 6661-6673, 2009.
Li, Wen-Tai et al., "Synthesis and Biological Activities of 2-Amino-1-Arylidenamino Imidazoles as Orally Active Anticancer Agents," *J. Med. Chem.*, vol. 53, pp. 2409-2417, 2010.
Lin, Wensheng et al., "Endoplasmic Reticulum Stress in Disorders of Myelinating Cells," *Nat Neuroscience*, vol. 12, pp. 379-385, 2009.
Marciniak, Stefan J. et al., "CHOP Induces Death by Promoting Protein Synthesis and Oxidation in the Stressed Endoplasmic Reticulum," *Genes & Development*, vol. 18, pp. 3066-3077, 2004.
Nguyen, Phu Hai et al., "Structure-Activity Relationship Study Around Guanabenz Identifies Two Derivatives Retaining Antiprion

(56) References Cited

OTHER PUBLICATIONS

Activity but Having Lost [alpha]2-Adrenergic Receptor Agonistic Activity," *ACS Chemical Neuroscience*, vol. 5, pp. 1075-1082, 2014.
Nishitoh, Hideki et al., "ASK1 is Essential for Endoplasmic Reticulum Stress-Induced Neuronal Cell Death Triggered by Expanded Polyglutamine Repeats," *Genes and Development*, vol. 16, pp. 1345-1355, 2002.
Novoa, Isabel et al., "Feedback Inhibition of the Unfolded Protein Response by GADD34-Mediated Dephosphorylation of eIF2α," *J. Cell Biol.*, vol. 153, pp. 1011-1021, 2001.
Pavitt, Graham D. et al., "New Insights into Translational Regulation in the Endoplasmic Reticulum Unfolded Protein Response," *Cold Spring Harbor Perspectives in Biology*, vol. 4, pp. 1-13, 2012.
Pervin, Shehla et al., "Increased Susceptibility of Breast Cancer Cells to Stress Mediated Inhibition of Protein Synthesis," *Cancer Research*, vol. 68, pp. 4862-4874, 2008.
Powers, Evan T. et al., "Biological and Chemical Approaches to Diseases of Proteostasis Deficiency," *Annu. Rev. Biochem.*, vol. 78, pp. 959-991, 2009.
Ring, Joshua R. et al., "Improving the Inhibitory Activity of Arylidenaminoguanidine Compounds at the n-methyl-d-aspartate Receptor Complex From a Recursive Computational-Experiment Structure-Activity Relationship Study", *Bioorganic & Medicinal Chemistry*, vol. 21, pp. 1764-1774, 2013.
Robert, Francis et al., "Initiation of Protein Synthesis by Hepatitis C Virus is Refractory to Reduced eIF2 GTP Met-tRNA,$^{Met}$ Ternary Complex Availability," *Molecular Biology of the Cell*, vol. 17, pp. 4632-4644, 2006.
Scheuner, Donalyn et al., "Translational Control is Required for the Unfolded Protein Response and in Vivo Glucose Homeostasis," *Molecular Cell*, vol. 7, pp. 1165-1176, 2001.
Schilling, Gabriele et al., "Intranuclear Inclusions and Neuritic Aggregates in Transgenic Mice Expressing a Mutant N-terminal Fragment of Huntingtin," *Human Molecular Genetics*, vol. 8, pp. 397-407, 1999.
Stenlund, Peter et al., "Studies of Small Molecule Interactions With Protein Phosphatases Using Biosensor Technology," *Analytical Biochemistry*, vol. 353, pp. 217-225, 2006.
Tavernarakis, Nektarios, "Ageing and the Regulation of Protein Synthesis: A Balancing Act?" *Trends in Cell Biology*, vol. 18, pp. 228-235, 2008.
Tribouillard-Tanvier et al., Antihypertensive Drug Guanabenz is Active in Vivo Against Both Yeast and Mammalian Prions, *PLoS One*, vol. 3, Issue 4, pp. 1-7 (2008).
Tsaytler, Pavel et al., "Exploiting The Selectivity of Protein Phosphatase 1 for Pharmacological Intervention," *FEBS Journal*, vol. 280, pp. 766-770, 2013.
Tsaytler, Pavel et al., "Selective Inhibition of a Regulatory Subunit of Protein Phosphatase 1 Restores Proteostasis," *Science*, vol. 332, pp. 91-94, 2011.
Virshup, David M. et al., "From Promiscuity to Precision: Protein Phosphatases Get a Makeover," *Molecular Cell*, vol. 33, pp. 537-545, 2009.
International Search Report in PCT/GB2016/050990, dated Aug. 30, 2016 (6 pages).
International Search Report in PCT/GB2016/050991, dated Jun. 6, 2016 (6 pages).
Way, S.W. et al., "Harnessing the Integrated Stress Response for the Treatment of Multiple Sclerosis," *Lancet Neurol,*, vol. 15, pp. 434-443 (2016); published online Feb. 10, 2016.

\* cited by examiner

Figure 1 A selective R15B inhibitor (compound of Example 1) selectively binds to R15B-PP1
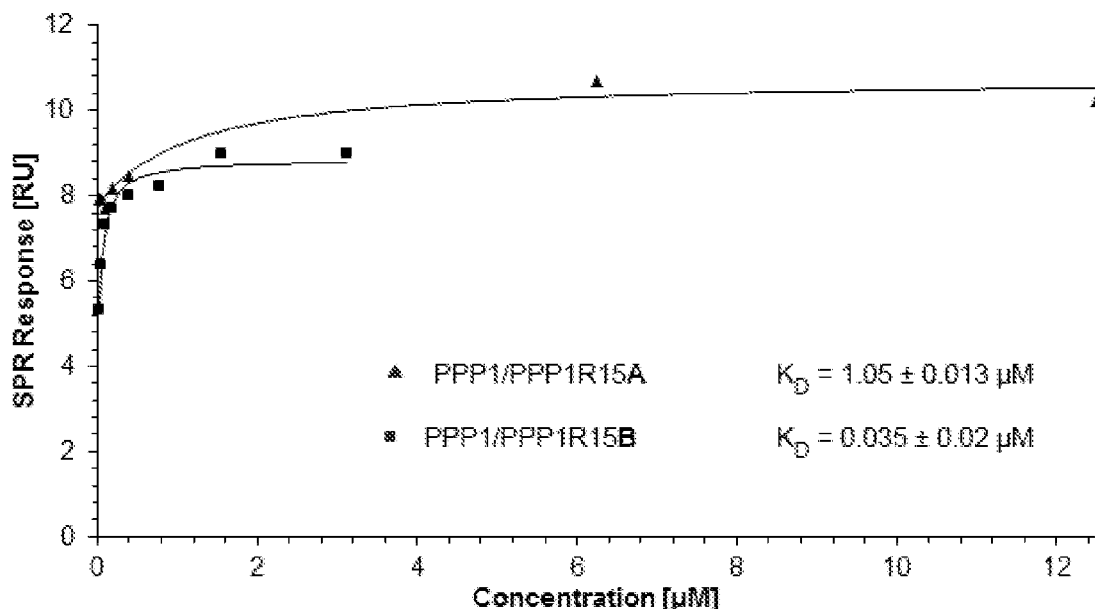
Figure 2 A selective R15B inhibitor (compound of Example 1) induces a transient phosphorylation of eIF2α in cells and expression of R15A in cells, in the absence of stress
A
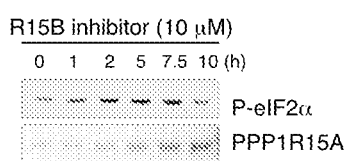
B
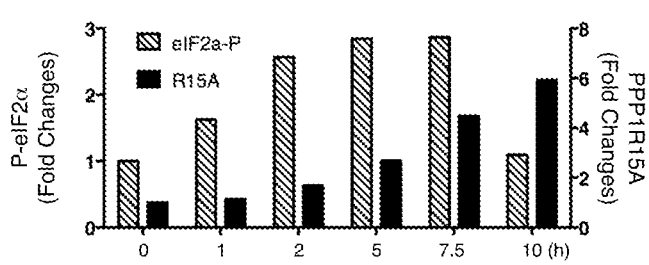

Figure 3 A selective R15B inhibitor (compound of Example 1) protects cells from stress
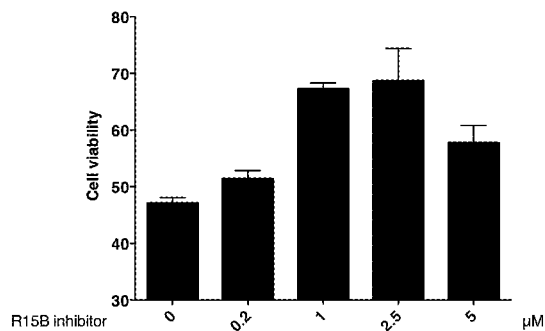
Figure 4 A selective R15B inhibitor prolongs eIF2a phosphorylation during stress-recovery
A
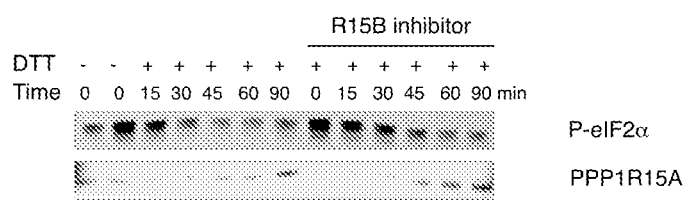
B
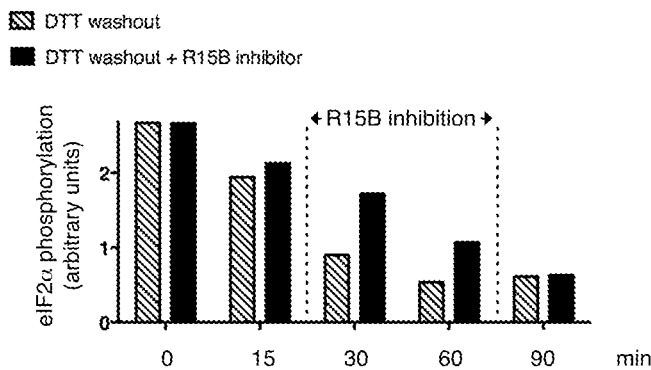

Figure 5 Tissue distribution of Example 1 in mice 1 h after oral administration (2 mg/kg)
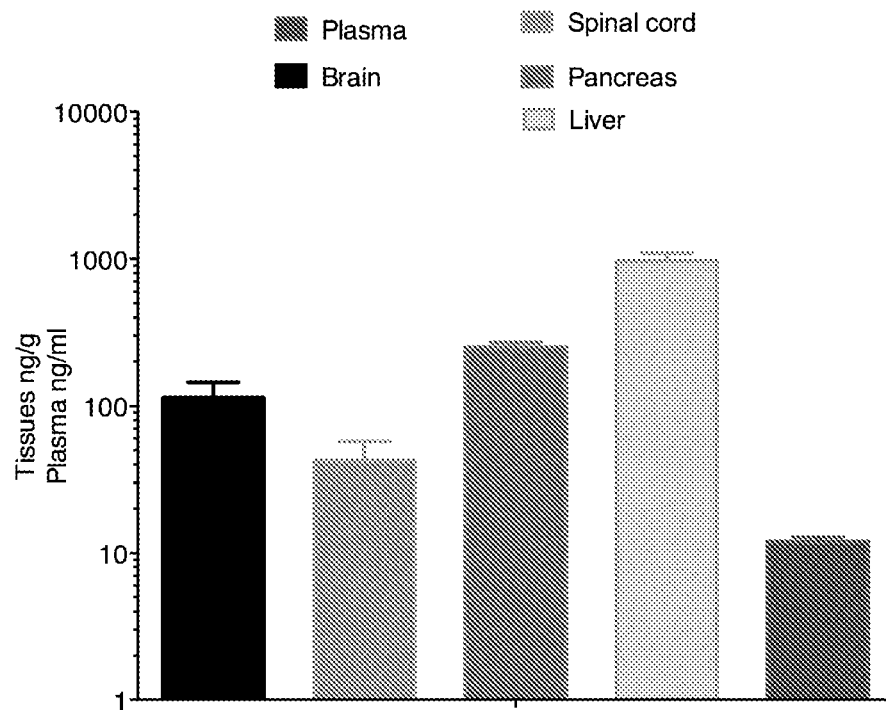
Figure 6 Treatment of mice with a compound of Example 1 (10 mg/kg) is not toxic to mice
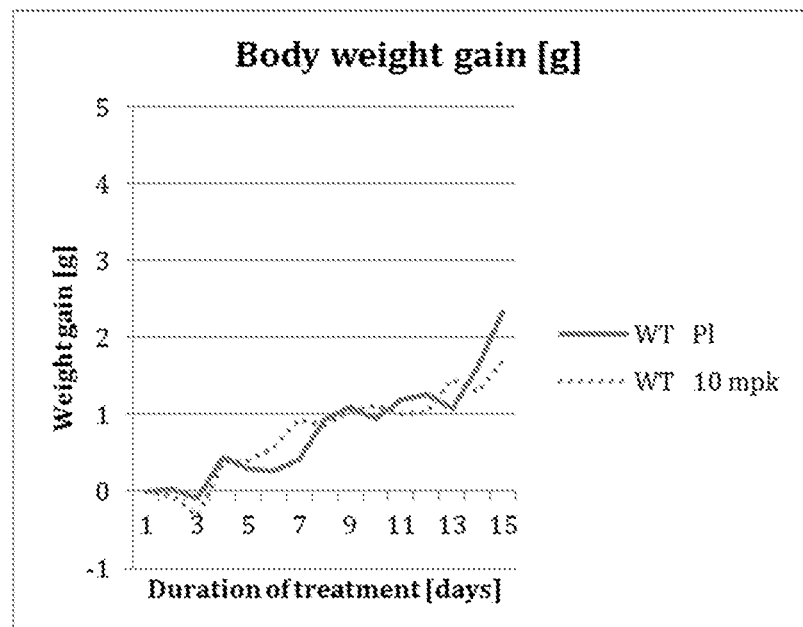

Figure 7 Treatment of mice with a compound of Example 1 does not cause the side effects of Guanabenz
Mice were treated with Guanabenz (10 mg/kg) or compound of Example 1 orally and their activity was scored 30 min after dosing.
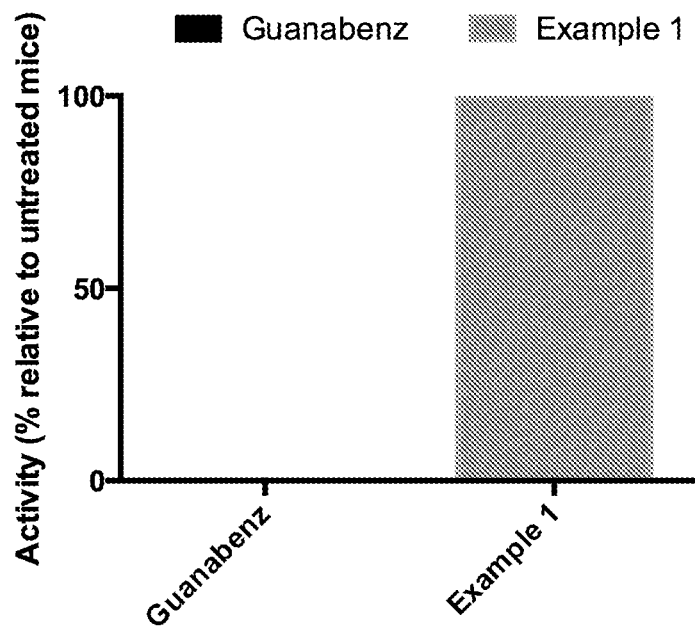
Figure 8 Induction of R15A in a mammal following treatment with a compound of Example 1
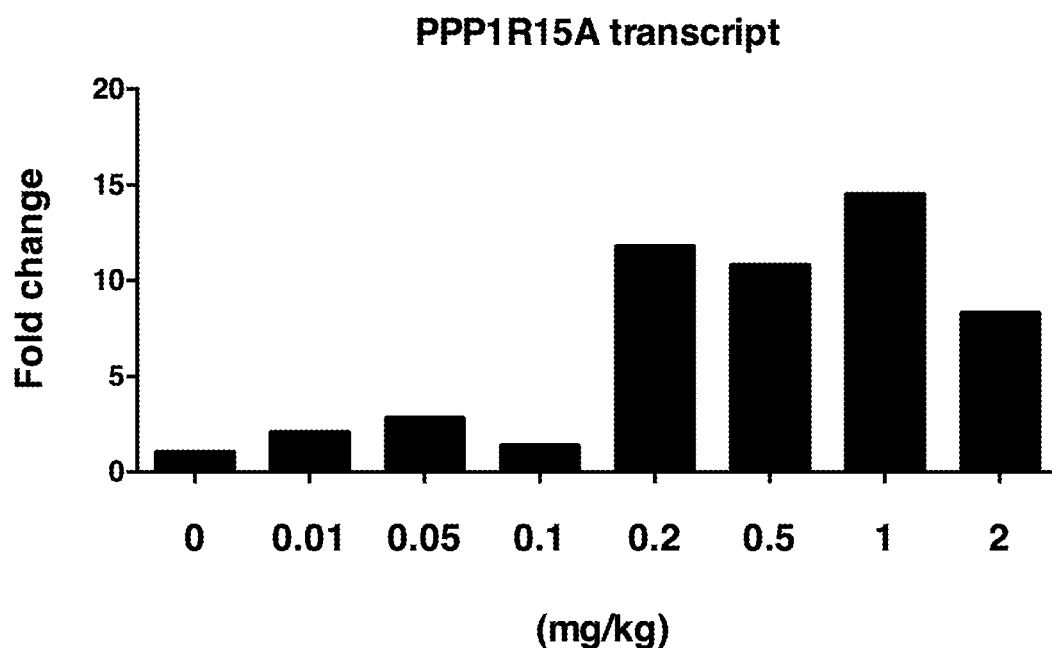

Figure 9 A compound of Example 1 prevents a disease in a mammal
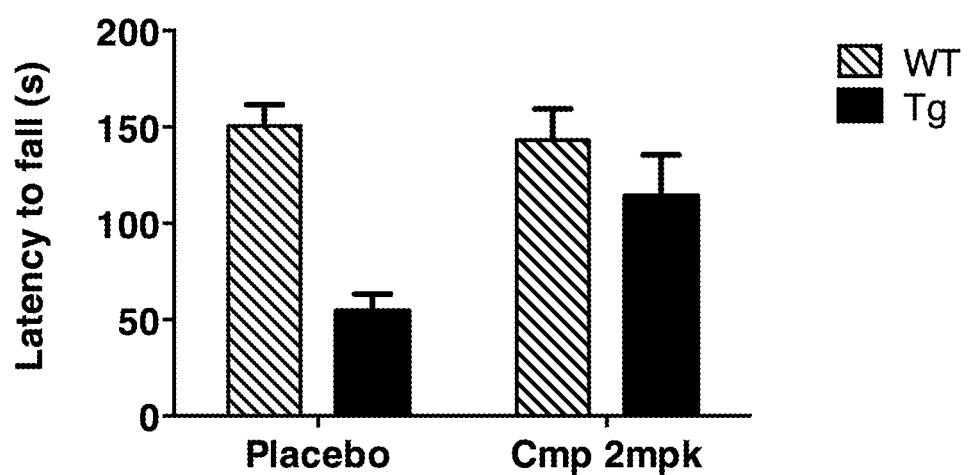
Figure 10 A compound of Example I improves myelination in explant cultures from neuropathic mice
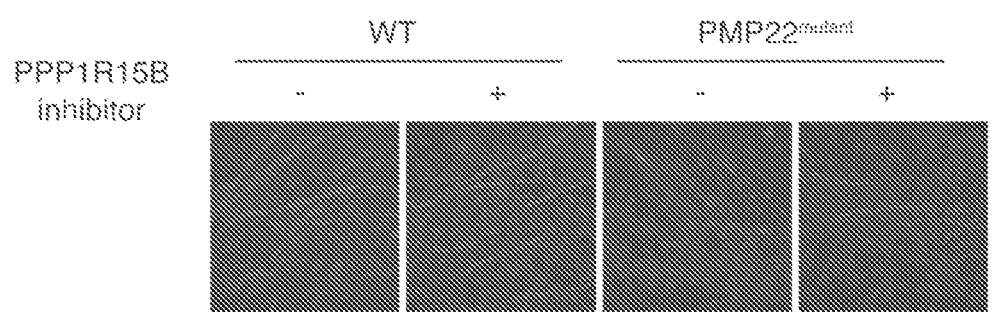

Figure 11 Compound of Example I reduces a metabolic disorder
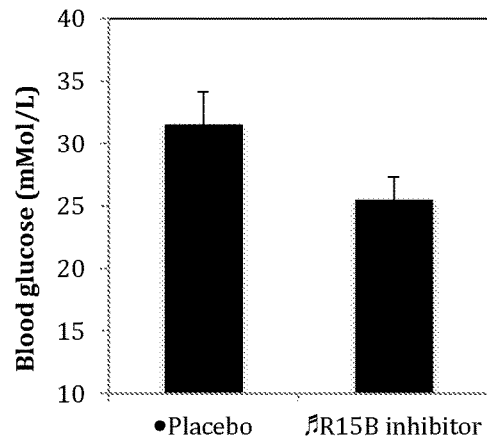
Figure 12 Monitoring protein synthesis rates distinguishes R15A, R15B and R15A/B inhibitor
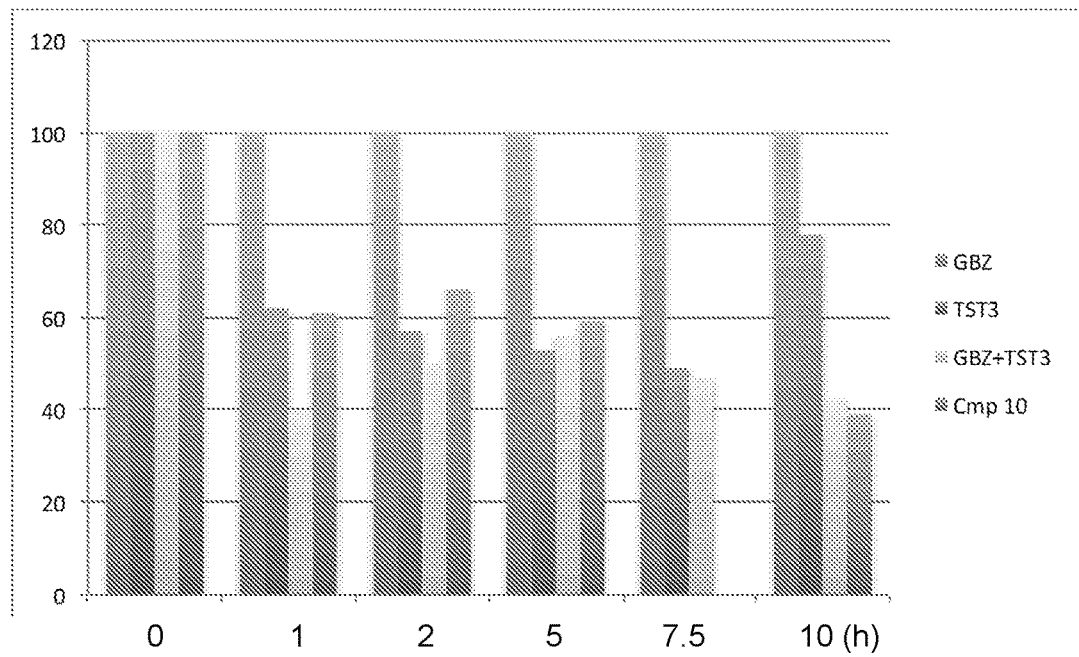
Figure 13 Immunoblot showing that an R15A/B inhibitor (compound 10 at 20 µM) induces expression of ATF4, confirming its on-target effect
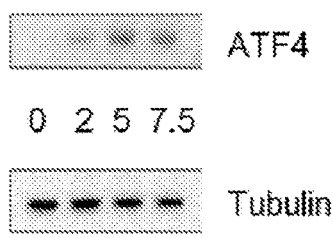

INHIBITORS AND THEIR USES

CROSS-REFERENCE TO RELATED APPLICATIONS

This application is a continuation of U.S. application Ser. No. 15/564,834, filed on Oct. 6, 2017, incorporated by reference in its entirety, which is the U.S. national phase entry under 35 U.S.C. § 371 of International Application No. PCT/GB2016/050991, filed on Apr. 8, 2016, which claims priority to GB Application Nos. 1505975.1 and 1505971.0, both filed on Apr. 8, 2015.

BACKGROUND TO THE INVENTION

The reversible phosphorylation of proteins controls virtually all aspects of cell and organismal function, allowing cells to adapt to sudden changes through the antagonistic action of kinases and phosphatases. Consequently, targeting phosphorylation offers a broad range of therapeutic opportunities and kinases have arisen as the most prevalent drug targets in today's pharmaceutical research with more than 3000 approved and experimental drugs. However, while targeting phosphatases should in principle be as attractive as kinases, the therapeutic potential of phosphatases has been overlooked. The majority of protein phosphorylation occurs on serine and threonine and selective serine/threonine dephosphorylation is achieved by hundreds of different dimeric or trimeric holoenzymes assembled from one of only a few catalytic subunits combined with one amongst hundreds of diverse regulatory subunits (Heroes et al., FEBS Journal, 280, 584-595, 2012). Thus, inhibition of the catalytic component of the holoenzyme such as PP1c results in inhibition of hundreds of phosphatases and is toxic. Since selectivity is an important property for drug development, the promiscuity of catalytic phosphatases has led them to acquire the reputation of being undruggable.

Phosphorylation of the α subunit of eIF2α is the first line of defense against a variety of stresses and is thereby a central component of two partly overlapping signaling pathways: the Unfolded Protein Response (UPR) and the Integrated Stress Response (ISR). To reverse eIF2α phosphorylation, mammalian cells have two eIF2α phosphatases. The eIF2α phosphatases are dimeric holoenzymes that share a catalytic subunit PP1c with about 200 other phosphatases, and are bound to one of two related regulatory subunits: PPP1R15A (Novoa et al., The Journal of Cell Biology, 153, 1345-1355, 2001), a stress inducible protein or PPP1R15B, which is constitutively expressed (Jousse et al., The Journal of Cell Biology, 163, 767-775, 2003).

Recently, the feasibility of inhibiting selectively a serine/threonine phosphatase has been demonstrated. Guanabenz (Tsaytler et al., Science, 332, 91-94, 2011; Tsaytler and Bertolotti, FEBS Journal, 280, 766-770, 2012) and its derivatives, some of which are disclosed in WO2014108520 (Medical Research Council), were found to selectively inhibit PPP1R15A/GADD34, a stress-induced regulatory subunit of the serine/threonine protein phosphatase 1, and was proposed as a treatment for diseases associated with protein misfolding stress.

PPP1R15A inhibition selectively inhibits the stress-induced eIF2α phosphatase composed of PPP1R15A and PP1, while sparing the highly related and constitutive phosphatase PPP1R15B-PP1. PPP1R15A inhibition prolongs eIF2α phosphorylation in stressed cells and this results in prolonging translation attenuation in stressed cells. As a consequence, chaperone availability is increased in stressed cells because the chaperones that are normally engaged in assisting the folding of newly synthetized proteins become available when translation is decreased. This favors protein folding and rescues cells from protein proteostasis defects. Thus, in principle, PPP1R15A inhibitors could treat mammalian diseases involving protein misfolding stress. Inhibition of PPP1R15A in mammals has an attractive therapeutic potential because inhibition of PPP1R15A is predicted to be safe as PPP1R15A/GADD34 knock-out mice are largely indistinguishable from wild-type mice (Marciniak et al., Genes & Development, 18, 3066-3077, 2004). However, the number of therapeutic indications that can be treated with PPP1R15A inhibitors is predicted to be restricted to diseases where PPP1R15A is expressed and where PPP1R15A is in the disease mode of action. Thus, inhibition of PPP1R15A may be powerful and safe but will be restricted to diseases involving PPP1R15A.

Regardless of the limitations associated with PPP1R15A inhibition, the approach of restoring proteostasis by fine tuning translation to increase chaperone availability is in theory powerful, straightforward and applicable to correct a broad range of diseases involving misfolded proteins. As noted above, the use of PPP1R15A inhibitors will be restricted to diseases where PPP1R15A is expressed and where PPP1R15A is in the disease mode of action. This represents a serious limitation. Thus alternative approaches, of broad therapeutic potential, are needed and the present invention seeks to provide these.

SUMMARY OF THE INVENTION

Compounds which inhibit PPP1R15A and PPP1R15B can advantageously be used to treat a wider range of diseases than compounds which selectively inhibit PPP1R15A.

In a first aspect, the present invention provides compounds of formula IA:

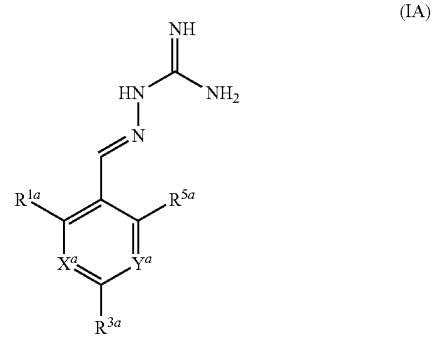

or a pharmaceutically acceptable salt thereof, wherein:
$X^a$ is N or $CR^{2a}$;
$Y^a$ is N or $CR^{4a}$;
$R^{1a}$ is H, F, Cl or Br;
$R^{2a}$, $R^{3a}$, $R^{4a}$, $R^{5a}$ each independently represent H, F or Cl;
with the proviso that:
when $X^a$ and $Y^a$ represent $CR^{2a}$ and $CR^{4a}$ respectively and $R^{2a}$ and $R^{4a}$ are both H:
  $R^{1a}$ is not F, Cl or Br when $R^{3a}$ and $R^{5a}$ both represent H;
  $R^{5a}$ is not F or Cl when $R^{1a}$ is Cl and $R^{2a}$ is H;
  $R^{3a}$ is not F when $R^{1a}$ is Cl and $R^{5a}$ is H;
  $R^{3a}$ is not Cl when $R^{1a}$ and $R^{5a}$ are both H or when $R^{1a}$ is Cl and $R^{5a}$ is H;
  $R^{1a}$, $R^{3a}$ and $R^{5a}$ are not all H;
  $R^{1a}$ is not Cl when $R^{3a}$ is H and $R^{5a}$ is F;

when $X^a$ represents CH and $Y^a$ represents $CR^{4a}$ wherein $R^{4a}$ is Cl:

$R^{1a}$ and $R^{5a}$ are not both Cl;

$R^{3a}$ is not Cl when $R^{1a}$ and $R^{5a}$ are Cl;

when $X^a$ represents $CR^{2a}$ and $Y^a$ represents $CR^{4a}$ and $R^{2a}$ and $R^{4a}$ are both Cl, $R^{1a}$, $R^{3a}$ and $R^{5a}$ are not all H.

In one embodiment, $X^a$ represents $CR^{2a}$ and $Y^a$ represents $CR^{4a}$, wherein $R^{2a}$ and $R^{4a}$ each independently represent H, F or Cl.

In one embodiment, three of $R^{1a}$, $R^{2a}$, $R^{3a}$, $R^{4a}$ and $R^{5a}$ represent Cl or F and two of $R^{1a}$, $R^{2a}$, $R^{3a}$, $R^{4a}$ and $R^{5a}$ represent H, optionally wherein at least one of $R^{1a}$, $R^{2a}$, $R^{3a}$, $R^{4a}$ and $R^{5a}$ is F.

In one embodiment, three of $R^{1a}$, $R^{2a}$, $R^{3a}$, $R^{4a}$ and $R^{5a}$ represent Cl and two of $R^{1a}$, $R^{2a}$, $R^{3a}$, $R^{4a}$ and $R^{5a}$ represent H.

In one embodiment, $R^{3a}$ is Cl or F and $R^{1a}$, $R^{2a}$, $R^{4a}$ and $R^{5a}$ are independently selected from H, F and Cl, wherein two of $R^{1a}$, $R^{2a}$, $R^{4a}$ and $R^{5a}$ are selected from F and Cl and two of $R^{1a}$, $R^{2a}$, $R^{4a}$ and $R^{5a}$ is H.

In one embodiment, $R^{5a}$ is H.

In one embodiment, the compound of formula IA is in the E-isomer form.

A second aspect of the invention relates to compounds of formula IB:

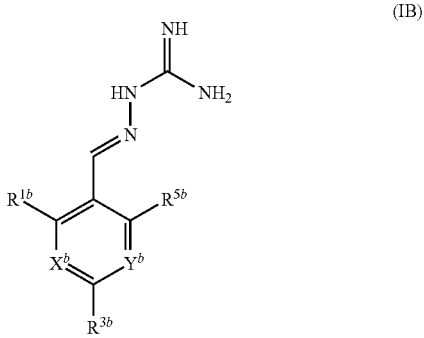

or a pharmaceutically acceptable salt thereof, wherein:

$X^b$ is N or $CR^{2b}$;

$Y^b$ is N or $CR^{4b}$;

$R^{1b}$ is H, F, Cl or Br;

$R^{2b}$, $R^{3b}$, $R^{4b}$, $R^{5b}$ each independently represent H, F or Cl;

with the proviso that:

when $X^b$ and $Y^b$ both represent N, $R^{1b}$ and $R^{3b}$ are not both Cl;

$R^{1b}$ is not Br when $X^b$ is $CR^{2b}$ and $R^{2b}$ is Cl;

when $R^{3b}$ and $R^{4b}$ are both H, $R^{1b}$ and $R^{2b}$ are not both Cl;

when $X^b$ is $CR^{2b}$ and $R^{2b}$ and $R^{3b}$ are both H, $R^{1b}$ is not Cl when $Y^b$ is $CR^{4b}$ and $R^{4b}$ is F;

when $X^b$ is $CR^{2b}$ and $Y^b$ is $CR^{4b}$, $R^{1b}$, $R^{2b}$, $R^{3b}$, $R^{4b}$ and $R^{5b}$ are not all H;

when $X^b$ is $CR^{2b}$ and $Y^b$ is $CR^{4b}$ and $R^{2b}$, $R^{3b}$, $R^{4b}$ and $R^{5b}$ are H, $R^{1b}$ is not Cl;

when $X^b$ is $CR^{2b}$ and $Y^b$ is $CR^{4b}$ and $R^{2b}$, $R^{3b}$ and $R^{4b}$ are H, $R^{1b}$ is not Cl when $R^{5b}$ is F;

for use in the treatment of a disease state alleviated by the inhibition of PPP1R15A and PPP1R15B.

In one embodiment, $X^b$ represents $CR^{2b}$ and $Y^b$ represents $CR^{4b}$, wherein $R^{2b}$ and $R^{4b}$ each independently represent H, F or Cl.

In one embodiment, three of $R^{1b}$, $R^{2b}$, $R^{3b}$, $R^{4b}$ and $R^{5b}$ represent Cl and two of $R^{1b}$, $R^{2b}$, $R^{3b}$, $R^{4b}$ and $R^{5b}$ represent H.

In one embodiment, three of $R^{1b}$, $R^{2b}$, $R^{3b}$, $R^{4b}$ and $R^{5b}$ represent Cl or F and two of $R^{1b}$, $R^{2b}$, $R^{3b}$, $R^{4b}$ and $R^{5b}$ represent H, optionally wherein at least one of $R^{1b}$, $R^{2b}$, $R^{3b}$, $R^{4b}$ and $R^{5b}$ is F.

In one embodiment, $R^{3b}$ is Cl or F and $R^{1b}$, $R^{2b}$, $R^{4b}$ and $R^{5b}$ are independently selected from H, F and Cl, wherein three of $R^{1b}$, $R^{2b}$, $R^{4b}$ and $R^{5b}$ are selected from F and Cl and one of $R^{1b}$, $R^{2b}$, $R^{4b}$ and $R^{5b}$ is H.

In one embodiment, $R^{5a}$ is H.

In one embodiment, the compound of formula IB is in the E-isomer form.

A further aspect of the invention relates to compounds of formula IA for use in therapy.

A further aspect of the invention relates to compounds of formula IA or formula IB for use in the treatment of a disease state alleviated by the inhibition of PPP1R15A and PPP1R15B.

A further aspect of the invention relates to use of a compound of formula IA or formula IB in the preparation of a medicament for treating a disease state alleviated by the inhibition of PPP1R15A and PPP1R15B.

A further aspect of the invention relates to methods of treating a disease state alleviated by the inhibition of PPP1R15A and PPP1R15B in a subject in need thereof, said method comprising administering a therapeutically effective amount of a compound of formula IA or IB.

In one embodiment, the disease state alleviated by the inhibition of PPP1R15A and PPP1R15B is a disorder associated with accumulation of misfolded proteins or proteostatsis disorder.

In a further embodiment, the disease is Huntington's disease, Parkinson's disease, a tauopathy, a protein trafficking disease or a myelin disorder.

In another embodiment, the disease is any polyglutamine disorder.

In a further embodiment, the disease is Distal hereditary motor neuropathy with mutations in the chaperone HSJ1.

A further aspect of the invention relates to pharmaceutical compositions comprising a compound of formula IA or formula IB as described above, admixed with a suitable pharmaceutically acceptable diluent, excipient or carrier.

BRIEF DESCRIPTION OF THE FIGURES

Certain embodiments of the present invention will now be described, by way of example only, with reference to the drawings in which:

FIG. 1 shows the selective binding of a R15B inhibitor of Example 1 to R15B-PP1 over R15A-PP1.

FIG. 2 shows that a selective R15B inhibitor of Example 1 induces a transient phosphorylation of eIF2α in cells in the absence of stress and induces expression of R15A in cells.

FIG. 3 shows that a selective R15B inhibitor of Example 1 protects cells from stress.

FIG. 4 shows the effects of a selective R15B inhibitor on eIF2α phosphorylation following stress. The compound of Example 1 prolongs eIF2☐ phosphorylation following stress at times where R15A is not yet expressed.

FIG. 5 shows the tissue distribution of a compound of Example 1 which exhibits extensive tissue distribution.

FIG. 6 shows that the treatment of mice with a compound of Example 1 (10 mg/kg) is not toxic.

FIG. 7 shows that the treatment of mice with a compound of Example 1 (10 mg/kg) does not cause the side effects of Guanabenz FIG. 8 shows the induction of R15A in a mammal following treatment with a compound of Example 1.

FIG. 9 shows the effectiveness of a R15B inhibitor of Example 1 in preventing disease in a mammal. The example used in FIG. 8 is Huntington's disease using the mouse model HD82Gln (Schilling et al., Hum. Mol. Genet., 8, 387-407, 1999). WT: wild-type mice. Tg: HD82Gln.

FIG. 10 shows myelin internodes in red (rod shaped) from cultured dorsal root ganglia (DRG) and nuclei in blue (spherical 'blob' shaped) in of the indicated genotype treated with vehicle or compound of Example 1. The myelin internodes in the PMP22-mutant mice are shorter. Treatment with a compound of Example 1 increased the length of myelin internodes in mutant DRG revealing that it improved myelination.

FIG. 11 shows blood glucose levels in obese mice db/db animals (n=5 per condition) following treatment with compound of Example 1.

FIG. 12 shows protein synthesis rates for a selective R15A inhibitor (1st column—guanabenz (GBZ)), a selective R15B inhibitor (2nd column—compound 16 (TST3)), a combination of GBZ and TST3 (3rd column), and an R15A/B inhibitor (4th column—compound 10). The figure shows that a selective R15A inhibitor doesn't inhibit protein synthesis in unstressed cell. A selective R15B inhibitor transiently inhibits protein synthesis in unstressed cells. Combining an R15A and an R15B inhibitor results in a persistent inhibition of protein synthesis. Likewise, an R15A/B inhibitor persistently inhibits protein synthesis. Y axis shows the relative rates of protein synthesis. X axis shows time following addition of the compounds (10 μM), in hours (h).

FIG. 13 shows an immunoblot showing that an R15A/B inhibitor (compound 10 at 20 μM) induces expression of ATF4, confirming the compound is on-target effect. Time after the addition of the compound to cells in culture is shown underneath the ATF4 immunoblot (0, 2, 5, 7.5 h).

DETAILED DESCRIPTION OF THE INVENTION

In a first aspect, the present invention provides compounds of formula IA:

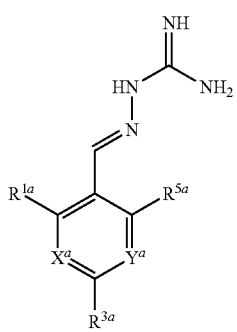

(IA)

or a pharmaceutically acceptable salt thereof, wherein:
$X^a$ is N or $CR^{2a}$;
$Y^a$ is N or $CR^{4a}$;
$R^{1a}$ is H, F, Cl or Br;
$R^{2a}$, $R^{3a}$, $R^{4a}$, $R^{5a}$ each independently represent H, F or Cl;
with the proviso that:
when $X^a$ and $Y^a$ represent $CR^{2a}$ and $CR^{4a}$ respectively and $R^{2a}$ and $R^{4a}$ are both H:
  $R^{1a}$ is not F, Cl or Br when $R^{3a}$ and $R^{5a}$ both represent H;
  $R^{5a}$ is not F or Cl when $R^{1a}$ is Cl and $R^{2a}$ is H;
  $R^{3a}$ is not F when $R^{1a}$ is Cl and $R^{5a}$ is H;
  $R^{3a}$ is not Cl when $R^{1a}$ and $R^{5a}$ are both H or when $R^{1a}$ is Cl and $R^{5a}$ is H;
  $R^{1a}$, $R^{3a}$ and $R^{5a}$ are not all H;
  $R^{1a}$ is not Cl when $R^{3a}$ is H and $R^{5a}$ is F;
when $X^a$ represents CH and $Y^a$ represents $CR^{4a}$ wherein $R^{4a}$ is Cl:
  $R^{1a}$ and $R^{5a}$ are not both Cl;
  $R^{3a}$ is not Cl when $R^{1a}$ and $R^{5a}$ are Cl;
when $X^a$ represents $CR^{2a}$ and $Y^a$ represents $CR^{4a}$ and $R^{2a}$ and $R^{4a}$ are both Cl, $R^{1a}$, $R^{3a}$ and $R^{5a}$ are not all H.

In one embodiment, $R^{1a}$ is F, Cl or Br.
In another embodiment, $R^{3a}$ is F or Cl.
In another embodiment, $R^{5a}$ is H.
In one embodiment, when $X^a$ represents $CR^{2a}$ and $Y^a$ represents $CR^{4a}$, two of $R^{1a}$, $R^{2a}$, $R^{3a}$, $R^{4a}$ and $R^{5a}$ represent Cl.
In one embodiment, when $X^a$ represents $CR^{2a}$ and $Y^a$ represents $CR^{4a}$, one of $R^{1a}$, $R^{2a}$, $R^{3a}$, $R^{4a}$ and $R^{5a}$ represents Cl and one of $R^{1a}$, $R^{2a}$, $R^{3a}$, $R^{4a}$ and $R^{5a}$ represents F.
In one embodiment, when $X^a$ represents $CR^{2a}$ and $Y^a$ represents $CR^{4a}$, one of $R^{1a}$, $R^{2a}$, $R^{3a}$, $R^{4a}$ and $R^{5a}$ represents Cl and one of $R^{1a}$, $R^{2a}$, $R^{3a}$, $R^{4a}$ and $R^{5a}$ represents Br.
In one embodiment, $R^{1a}$ and $R^{3a}$ both represent Cl.
In one embodiment, when $X^a$ represents $CR^{2a}$ and $Y^a$ represents $CR^{4a}$, three of $R^{1a}$, $R^{2a}$, $R^{3a}$, $R^{4a}$ and $R^{5a}$ represent Cl and two of $R^{1a}$, $R^{2a}$, $R^{3a}$, $R^{4a}$ and $R^{5a}$ represent H.
In one embodiment, when $X^a$ represents $CR^{2a}$ and $Y^a$ represents $CR^{4a}$, two of $R^{1a}$, $R^{2a}$, $R^{3a}$, $R^{4a}$ and $R^{5a}$ represent Cl, one of $R^{1a}$, $R^{2a}$, $R^{3a}$, $R^{4a}$ and $R^{5a}$ represents F, and two of $R^{1a}$, $R^{2a}$, $R^{3a}$, $R^{4a}$ and $R^{5a}$ represent H.
In one embodiment, when $X^a$ represents $CR^{2a}$ and $Y^a$ represents $CR^{4a}$, two of $R^{1a}$, $R^{2a}$, $R^{3a}$, $R^{4a}$ and $R^{5a}$ represent F, one of $R^{1a}$, $R^{2a}$, $R^{3a}$, $R^{4a}$ and $R^{5a}$ represents Cl and two of $R^{1a}$, $R^{2a}$, $R^{3a}$, $R^{4a}$ and $R^{5a}$ represent H.
In one embodiment, three of $R^{1a}$, $R^{2a}$, $R^{3a}$, $R^{4a}$ and $R^{5a}$ represent Cl or F and two of $R^{1a}$, $R^{2a}$, $R^{3a}$, $R^{4a}$ and $R^{5a}$ represent H, optionally wherein at least one of $R^{1a}$, $R^{2a}$, $R^{3a}$, $R^{4a}$ and $R^{5a}$ is F.
In one embodiment, when $X^a$ represents $CR^{2a}$ and $Y^a$ represents $CR^{4a}$, $R^{3a}$ is Cl or F, two of $R^{1a}$, $R^{2a}$, $R^{4a}$ and $R^{5a}$ are selected from F and Cl and two of $R^{1a}$, $R^{2a}$, $R^{4a}$ and $R^{5a}$ represent H.
In one embodiment, when $X^a$ represents N, $R^{1a}$ and $R^{3a}$ both represent Cl.
In one embodiment,
$X^a$ is $CR^2a$;
$Y^a$ is $CR^4a$;
$R^{1a}$ is H, F, Cl or Br;
$R^{2a}$, $R^{3a}$ and $R^{4a}$ each independently represent H, F or Cl;
$R^{5a}$ represents H;
with the proviso that:
when $X^a$ and $Y^a$ represent CH:
  $R^{1a}$ is not F, Cl or Br when $R^{3a}$ and $R^{5a}$ both represent H;
  $R^{5a}$ is not F or Cl when $R^{1a}$ is Cl and $R^{2a}$ is H;
  $R^{3a}$ is not F when $R^{1a}$ is Cl and $R^{5a}$ is H;
  $R^{3a}$ is not Cl when $R^{1a}$ and $R^{5a}$ are both H or when $R^{1a}$ is Cl and $R^{5a}$ is H;
  $R^{1a}$, $R^{3a}$ and $R^{5a}$ are not all H;
  $R^{1a}$ is not Cl when $R^{3a}$ is H and $R^{5a}$ is F;

when $X^a$ represents CH and $Y^a$ represents $CR^{4a}$ wherein $R^{4a}$ is Cl:
$R^{1a}$ and $R^{5a}$ are not both Cl;
$R^{3a}$ is not Cl when $R^{1a}$ and $R^{5a}$ are Cl;
when $X^a$ represents $CR^{2a}$ and $Y^a$ represents $CR^{4a}$ and $R^{2a}$ and $R^{4a}$ are both Cl, $R^{1a}$, $R^{3a}$ and $R^{5a}$ are not all H.

In one embodiment, the compound of formula IA is in the E-isomer form.

In a second aspect, the present invention provides compounds of formula IB for use in the treatment of a disease state alleviated by the inhibition of PPP1R15A and PPP1R15B:

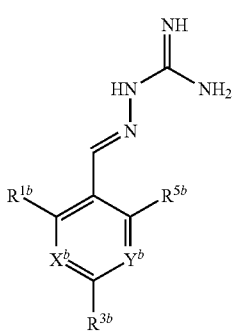

(IB)

or a pharmaceutically acceptable salt thereof, wherein:
$X^b$ is N or $CR^{2b}$;
$Y^b$ is N or $CR^{4b}$;
$R^{1b}$ is H, F, Cl or Br;
$R^{2b}$, $R^{3b}$, $R^{4b}$, $R^{5b}$ each independently represent H, F or Cl;
with the proviso that:
when $X^b$ and $Y^b$ both represent N, $R^{1a}$ and $R^{3b}$ are not both Cl;
$R^{1b}$ is not Br when $X^b$ is $CR^{2b}$ and $R^{2b}$ is Cl;
when $R^{3b}$ and $R^{4b}$ are both H, $R^{1b}$ and $R^{2b}$ are not both Cl;
when $X^b$ is $CR^{2b}$ and $R^{2b}$ and $R^{3b}$ are both H, $R^{1a}$ is not Cl when $Y^b$ is $CR^{4b}$ and $R^{4b}$ is F;
when $X^b$ is $CR^{2b}$ and $Y^b$ is $CR^{4b}$, $R^{1b}$, $R^{2b}$, $R^{3b}$, $R^{4b}$ and $R^{5b}$ are not all H;
when $X^b$ is $CR^{2b}$ and $Y^b$ is $CR^{4b}$ and $R^{2b}$, $R^{3b}$, $R^{4b}$ and $R^{5b}$ are H, $R^{1b}$ is not Cl;
when $X^b$ is $CR^{2b}$ and $Y^b$ is $CR^{4b}$ and $R^{2b}$, $R^{3b}$ and $R^{4b}$ are H, $R^{1b}$ is not Cl when $R^{5b}$ is F;
when $X^b$ is $CR^{2b}$ wherein $R^{2b}$ is Cl and $Y^b$ is $CR^{4b}$ wherein $R^{4b}$ is H, $R^{1b}$ is not Cl when $R^{3b}$, $R^{4b}$ and $R^{5b}$ are H, or when $R^{3b}$ and $R^{4b}$ are H and $R^{5b}$ is Cl.

In one embodiment, $X^b$ represents $CR^{2b}$ and $Y^b$ represents $CR^{4b}$. In an alternative embodiment, $X^b$ and $Y^b$ both represent N. In an alternative embodiment, $X^b$ represents N and $Y^b$ represents $CR^{4b}$.

The compounds of formula IB are R15A and R15B inhibitors.

In one embodiment, $R^{1b}$ represents F, Cl or Br.
In another embodiment, $R^{3b}$ represents F or Cl.
In another embodiment, $R^{5b}$ is H.
In one embodiment, when $X^b$ represents $CR^{2b}$ and $Y^b$ represents $CR^{4b}$, two of $R^{1b}$, $R^{2b}$, $R^{3b}$, $R^{4b}$ and $R^{5b}$ represent Cl.
In one embodiment, when $X^b$ represents $CR^{2b}$ and $Y^b$ represents $CR^{4b}$, one of $R^{1b}$, $R^{2b}$, $R^{3b}$, $R^{4b}$ and $R^{5b}$ represents Cl and one of $R^{1b}$, $R^{2b}$, $R^{3b}$, $R^{4b}$ and $R^{5b}$ represents F.

In one embodiment, $R^{1b}$ and $R^{3b}$ both represent Cl.
In one embodiment, when $X^b$ represents $CR^{2b}$ and $Y^b$ represents $CR^{4b}$, three of $R^{1b}$, $R^{2b}$, $R^{3b}$, $R^{4b}$ and $R^{5b}$ represent Cl.
In one embodiment, when $X^b$ represents $CR^{2b}$ and $Y^b$ represents $CR^{4b}$, two of $R^{1b}$, $R^{2b}$, $R^{3b}$, $R^{4b}$ and $R^{5b}$ represent Cl and one of $R^{1b}$, $R^{2b}$, $R^{3b}$, $R^{4b}$ and $R^{5b}$ represents F.
In one embodiment, when $X^b$ represents $CR^{2b}$ and $Y^b$ represents $CR^{4b}$, two of $R^{1b}$, $R^{2b}$, $R^{3b}$, $R^{4b}$ and $R^{5b}$ represent F and one of $R^{1b}$, $R^{2b}$, $R^{3b}$, $R^{4b}$ and $R^{5b}$ represents Cl.
In one embodiment, three of $R^{1a}$, $R^{2a}$, $R^{3a}$, $R^{4a}$ and $R^{5a}$ represent Cl or F and two of $R^{1a}$, $R^{2a}$, $R^{3a}$, $R^{4a}$ and $R^{5a}$ represent H, optionally wherein at least one of $R^{1a}$, $R^{2a}$, $R^{3a}$, $R^{4a}$ and $R^{5a}$ is F.

In one embodiment, when $X^b$ represents N, $R^{1b}$ and $R^{3b}$ both represent Cl.

In one embodiment,
$X^b$ is $CR^{2b}$;
$Y^b$ is $CR^{4b}$;
$R^{1b}$ is H, F, Cl or Br;
$R^{2b}$, $R^{3b}$ and $R^{4b}$ each independently represent H, F or Cl;
$R^{5b}$ is H;
with the proviso that:
when $X^b$ and $Y^b$ both represent N, $R^{1a}$ and $R^{3b}$ are not both Cl;
$R^{1b}$ is not Br when $X^b$ is $CR^{2b}$ and $R^{2b}$ is Cl;
when $R^{3b}$ and $R^{4b}$ are both H, $R^{1b}$ and $R^{2b}$ are not both Cl;
when $X^b$ is $CR^{2b}$ and $R^{2b}$ and $R^{3b}$ are both H, $R^{1a}$ is not Cl when $Y^b$ is $CR^{4b}$ and $R^{4b}$ is F;
when $X^b$ is $CR^{2b}$ and $Y^b$ is $CR^{4b}$, $R^{1b}$, $R^{2b}$, $R^{3b}$, $R^{4b}$ and $R^{5b}$ are not all H;
when $X^b$ is $CR^{2b}$ and $Y^b$ is $CR^{4b}$ and $R^{2b}$, $R^{3b}$, $R^{4b}$ and $R^{5b}$ are H, $R^{1b}$ is not Cl;
when $X^b$ is $CR^{2b}$ and $Y^b$ is $CR^{4b}$ and $R^{2b}$, $R^{3b}$ and $R^{4b}$ are H, $R^{1b}$ is not Cl when $R^{5b}$ is F;
when $X^b$ is $CR^{2b}$ wherein $R^{2b}$ is Cl and $Y^b$ is $CR^{4b}$ wherein $R^{4b}$ is H, $R^{1b}$ is not Cl when $R^{3b}$, $R^{4b}$ and $R^{5b}$ are H, or when $R^{3b}$ and $R^{4b}$ are H and $R^{5b}$ is Cl.

In one embodiment, the compound of formula IA is in the E-isomer form.

The term "PPP1R15A" is used interchangeable with the term "R15A" and the term "PPP1R15B" is used interchangeably with the term "R15B". An inhibitor of PPP1R15A and PPP1R15B may be referred to as "R15A/B", "R15AB" or "AB" throughout.

Compounds described herein include:

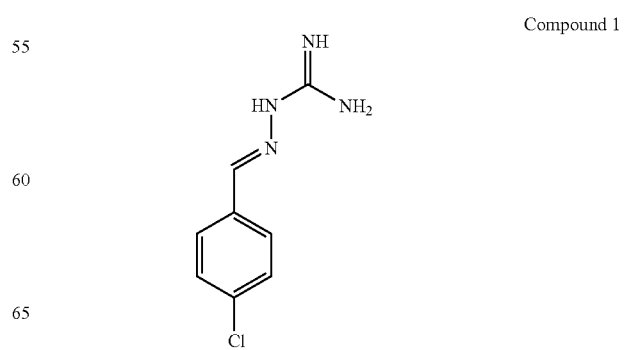

Compound 1

-continued

Compound 2

Compound 3

Compound 4

Compound 5

Compound 6

-continued

Compound 7

Compound 8

Compound 9

Compound 10

Compound 11

Compound 12
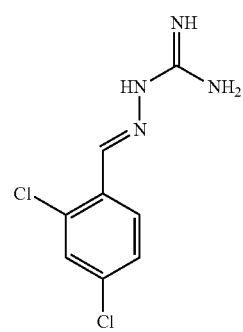
Compound 13
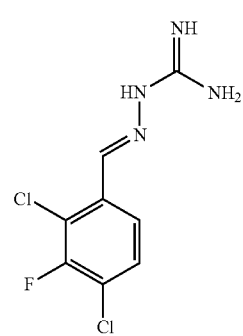
Compound 14
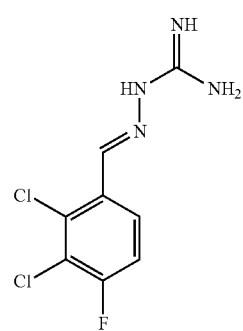
Compound 15
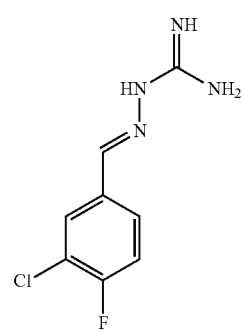
Compound 16
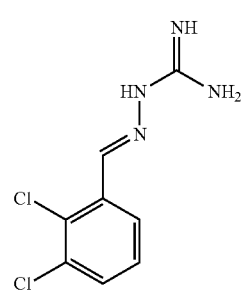
Compound 17
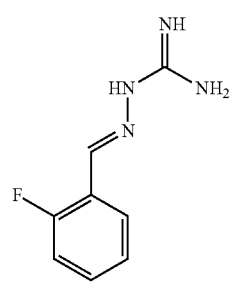
Compound 18
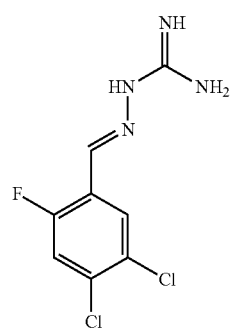
Compound 20
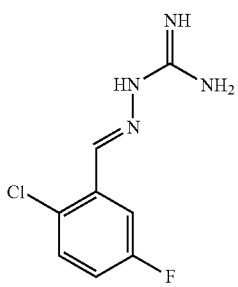
Compound 21
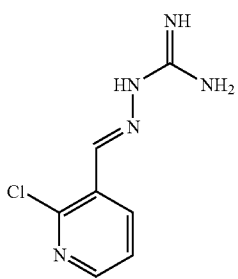
Compound 22
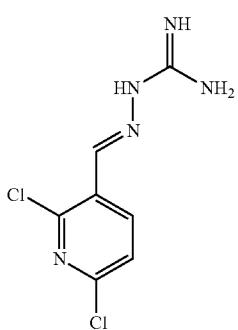

Compound 23
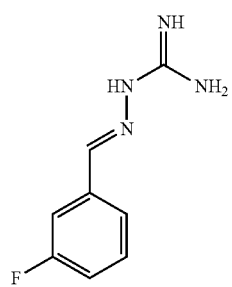
Compound 24
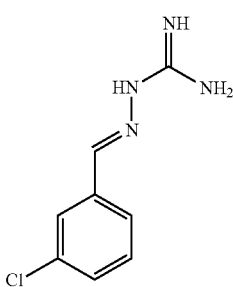
Compound 25
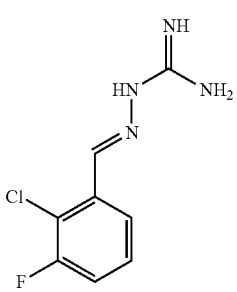
Compound 26
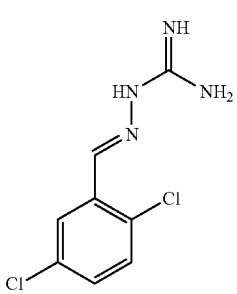
Compound 27
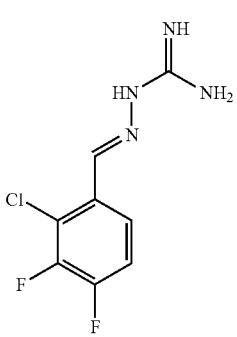
Compound 29
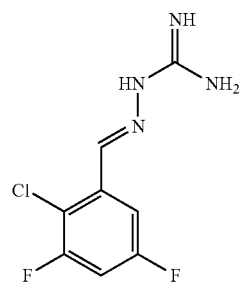
Compound 30
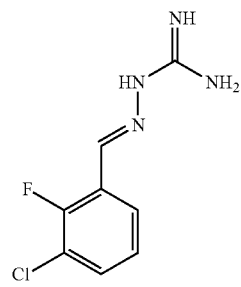
Compound 31
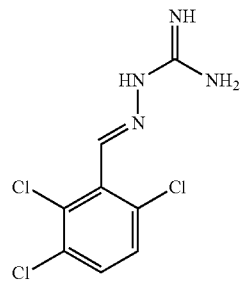
Compound 32
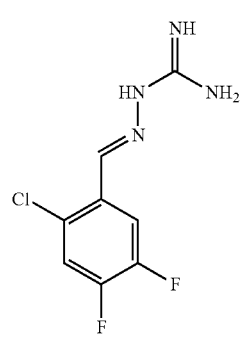
Compound 33
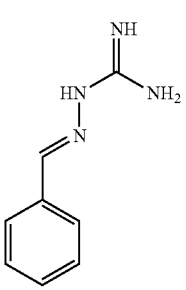

-continued

Compound 34

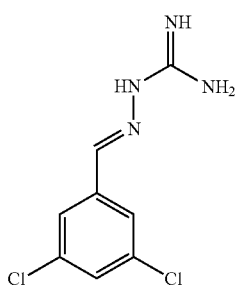

The E isomer forms of the compounds listed above are particularly preferred:

Compound 1(E)

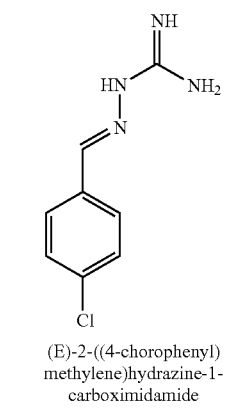

(E)-2-((4-chorophenyl)methylene)hydrazine-1-carboximidamide

Compound 2 (E)

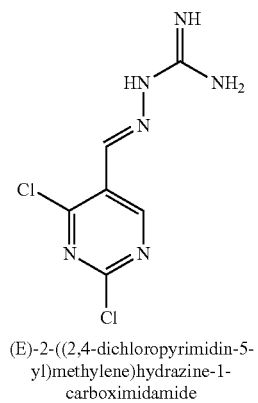

(E)-2-((2,4-dichloropyrimidin-5-yl)methylene)hydrazine-1-carboximidamide

Compound 3 (E)

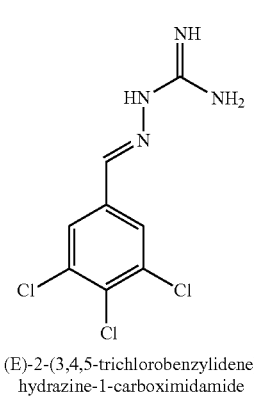

(E)-2-(3,4,5-trichlorobenzylidene)hydrazine-1-carboximidamide

Compound 4 (E)

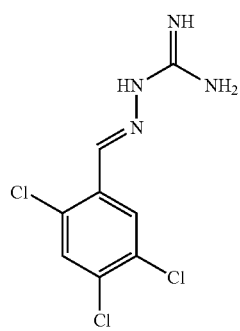

(E)-2-(2,4,5-trichlorobenzylidene)hydrazine-1-carboximidamide

Compound 5 (E)

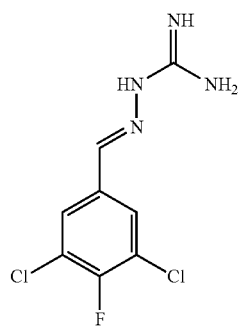

(E)-2-(3,5-dichloro-4-fluorobenzylidene)hydrazine-1-carboximidamide

Compound 6 (E)

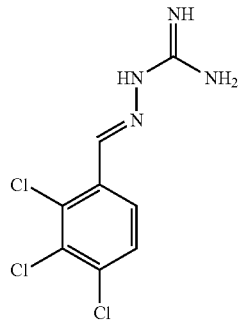

(E)-2-(2,3,4-trichlorobenzylidene)hydrazine-1-carboximidamide

Compound 7 (E)

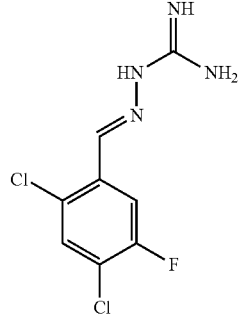

(E)-2-(2,4-dichloro-5-fluorobenzylidene)hydrazine-1-carboximidamide

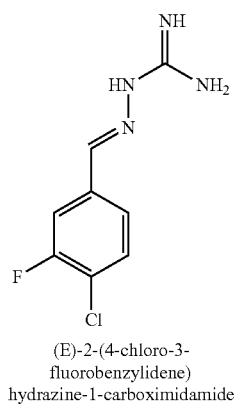

(E)-2-(4-chloro-3-fluorobenzylidene)hydrazine-1-carboximidamide

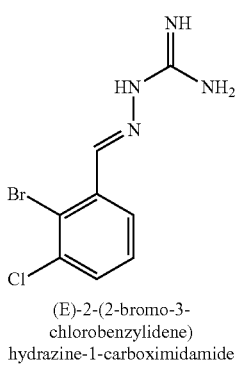

(E)-2-(2-bromo-3-chlorobenzylidene)hydrazine-1-carboximidamide

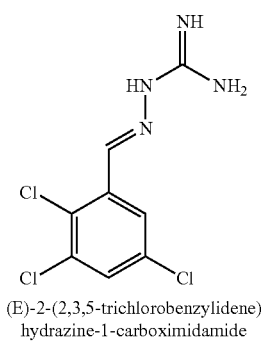

(E)-2-(2,3,5-trichlorobenzylidene)hydrazine-1-carboximidamide

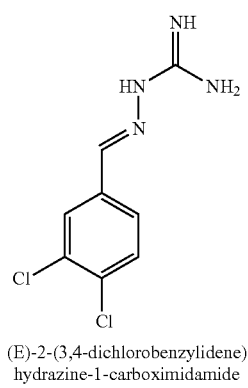

(E)-2-(3,4-dichlorobenzylidene)hydrazine-1-carboximidamide

Compound 8 (E)

Compound 9 (E)

Compound 10 (E)

Compound 11 (E)

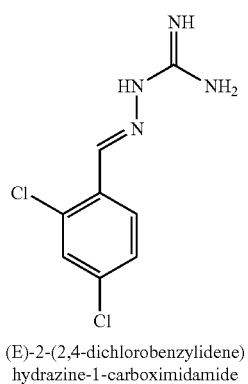

(E)-2-(2,4-dichlorobenzylidene)hydrazine-1-carboximidamide

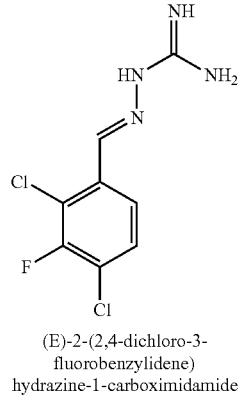

(E)-2-(2,4-dichloro-3-fluorobenzylidene)hydrazine-1-carboximidamide

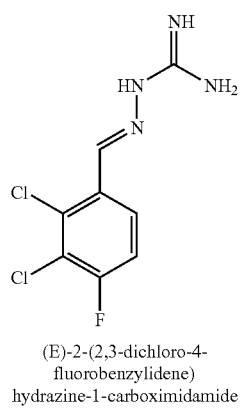

(E)-2-(2,3-dichloro-4-fluorobenzylidene)hydrazine-1-carboximidamide

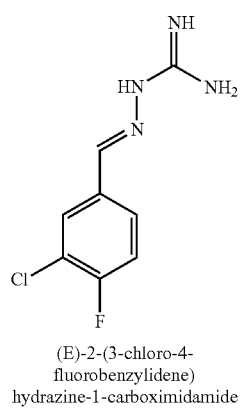

(E)-2-(3-chloro-4-fluorobenzylidene)hydrazine-1-carboximidamide

Compound 12 (E)

Compound 13 (E)

Compound 14 (E)

Compound 15 (E)

Compound 16 (E)

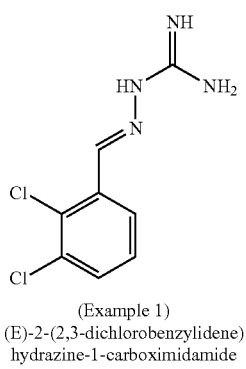

(Example 1)
(E)-2-(2,3-dichlorobenzylidene)
hydrazine-1-carboximidamide

Compound 17 (E)

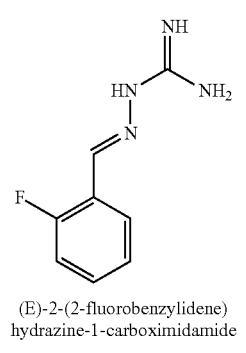

(E)-2-(2-fluorobenzylidene)
hydrazine-1-carboximidamide

Compound 18 (E)

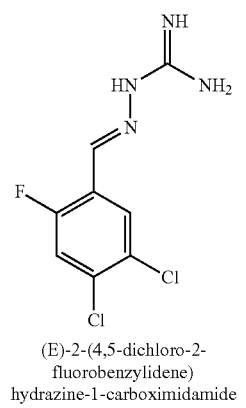

(E)-2-(4,5-dichloro-2-
fluorobenzylidene)
hydrazine-1-carboximidamide

Compound 20 (E)

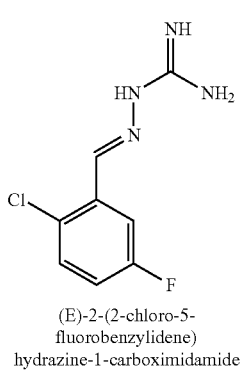

(E)-2-(2-chloro-5-
fluorobenzylidene)
hydrazine-1-carboximidamide

Compound 21 (E)

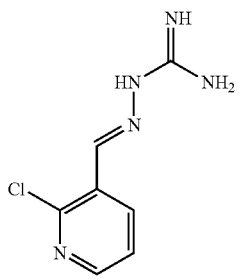

(E)-2-((2-chloropyridin-3-yl)
methylene)hydrazine-1-
carboximidamide

Compound 22 (E)

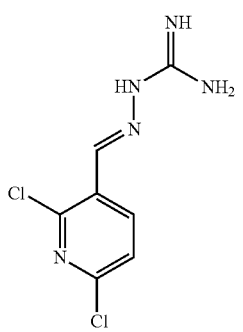

(E)-2-((2,6-dichloropyridin-3-yl)
methylene)
hydrazine-1-carboximidamide

Compound 23 (E)

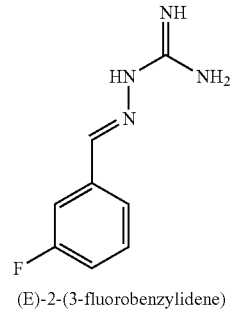

(E)-2-(3-fluorobenzylidene)
hydrazine-1-carboximidamide

Compound 24 (E)

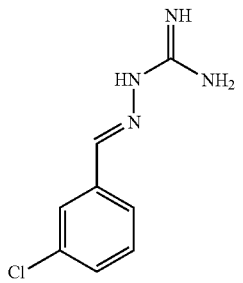

(E)-2-(3-chlorobenzylidene)
hydrazine-1-carboximidamide

Compound 25 (E)

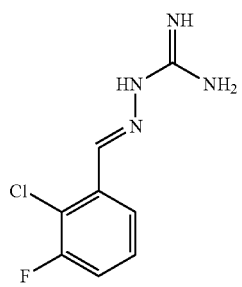

(E)-2-(2-chloro-3-
fluorobenzylidene)
hydrazine-1-carboximidamide

Compound 26 (E)

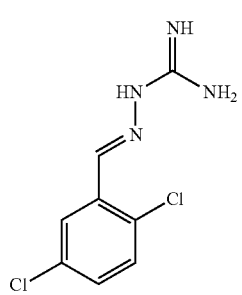

(E)-2-(2,5-dichlorobenzylidene)
hydrazine-1-carboximidamide

Compound 27 (E)

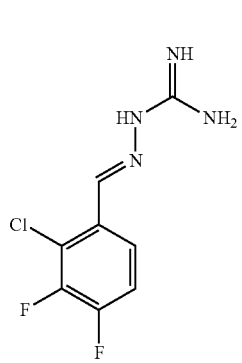

(E)-2-(2-chloro-3,4-
difluorobenzylidene)
hydrazine-1-carboximidamide

Compound 29 (E)

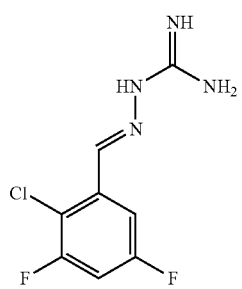

(E)-2-(2-chloro-3,5-
difluorobenzylidene)
hydrazine-1-carboximidamide

Compound 30 (E)

(E)-2-(3-chloro-2-
fluorobenzylidene)
hydrazine-1-carboximidamide

Compound 31 (E)

(E)-2-(2,3,6-trichlorobenzylidene)
hydrazine-1-carboximidamide

Compound 32 (E)

(E)-2-(2-chloro-4,5-
difluorobenzylidene)
hydrazine-1-carboximidamide

Compound 33 (E)

(E)-2-benzylidenehydrazine-
1-carboximidamide

-continued

Compound 34 (E)

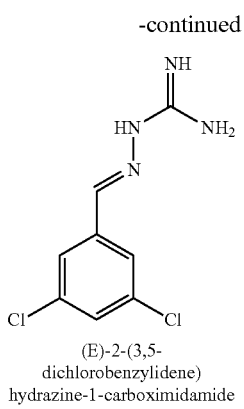

(E)-2-(3,5-dichlorobenzylidene)hydrazine-1-carboximidamide

Novel compounds of formula IA include:
Compound 2: 2-((2,4-dichloropyrimidin-5-yl)methylene)hydrazine-1-carboximidamide
Compound 3: 2-(3,4,5-trichlorobenzylidene)hydrazine-1-carboximidamide
Compound 4: 2-(2,4,5-trichlorobenzylidene)hydrazine-1-carboximidamide
Compound 5: 2-(3,5-dichloro-4-fluorobenzylidene)hydrazine-1-carboximidamide
Compound 6: 2-(2,3,4-trichlorobenzylidene)hydrazine-1-carboximidamide
Compound 7: 2-(2,4-dichloro-5-fluorobenzylidene)hydrazine-1-carboximidamide
Compound 9: 2-(2-bromo-3-chlorobenzylidene)hydrazine-1-carboximidamide
Compound 13: 2-(2,4-dichloro-3-fluorobenzylidene)hydrazine-1-carboximidamide
Compound 14: 2-(2,3-dichloro-4-fluorobenzylidene)hydrazine-1-carboximidamide
Compound 18: 2-(4,5-dichloro-2-fluorobenzylidene)hydrazine-1-carboximidamide
Compound 20: 2-(2-chloro-5-fluorobenzylidene)hydrazine-1-carboximidamide
Compound 22: 2-((2,6-dichloropyridin-3-yl)methylene)hydrazine-1-carboximidamide
Compound 25: 2-(2-chloro-3-fluorobenzylidene)hydrazine-1-carboximidamide
Compound 27: 2-(2-chloro-3,4-difluorobenzylidene)hydrazine-1-carboximidamide
Compound 29: 2-(2-chloro-3,5-difluorobenzylidene)hydrazine-1-carboximidamide
Compound 32: 2-(2-chloro-4,5-difluorobenzylidene)hydrazine-1-carboximidamide Novel compounds of formula IA may be selected from the following E isomer forms:
Compound 2(E): (E)-2-((2,4-dichloropyrimidin-5-yl)methylene)hydrazine-1-carboximidamide
Compound 3(E): (E)-2-(3,4,5-trichlorobenzylidene)hydrazine-1-carboximidamide
Compound 4(E): (E)-2-(2,4,5-trichlorobenzylidene)hydrazine-1-carboximidamide
Compound 5(E): (E)-2-(3,5-dichloro-4-fluorobenzylidene)hydrazine-1-carboximidamide
Compound 6(E): (E)-2-(2,3,4-trichlorobenzylidene)hydrazine-1-carboximidamide
Compound 7(E): (E)-2-(2,4-dichloro-5-fluorobenzylidene)hydrazine-1-carboximidamide
Compound 8(E): (E)-2-(4-chloro-3-fluorobenzylidene)hydrazine-1-carboximidamide
Compound 9(E): (E)-2-(2-bromo-3-chlorobenzylidene)hydrazine-1-carboximidamide
Compound 10(E): (E)-2-(2,3,5-trichlorobenzylidene)hydrazine-1-carboximidamide
Compound 11(E): (E)-2-(3,4-dichlorobenzylidene)hydrazine-1-carboximidamide
Compound 13(E): (E)-2-(2,4-dichloro-3-fluorobenzylidene)hydrazine-1-carboximidamide
Compound 14(E): (E)-2-(2,3-dichloro-4-fluorobenzylidene)hydrazine-1-carboximidamide
Compound 15(E): (E)-2-(3-chloro-4-fluorobenzylidene)hydrazine-1-carboximidamide
Compound 16(E): (E)-2-(2,3-dichlorobenzylidene)hydrazine-1-carboximidamide
Compound 18(E): (E)-2-(4,5-dichloro-2-fluorobenzylidene)hydrazine-1-carboximidamide
Compound 20(E): (E)-2-(2-chloro-5-fluorobenzylidene)hydrazine-1-carboximidamide
Compound 21(E): (E)-2-((2-chloropyridin-3-yl)methylene)hydrazine-1-carboximidamide
Compound 22(E): (E)-2-((2,6-dichloropyridin-3-yl)methylene)hydrazine-1-carboximidamide
Compound 23(E): (E)-2-(3-fluorobenzylidene)hydrazine-1-carboximidamide
Compound 24(E): (E)-2-(3-chlorobenzylidene)hydrazine-1-carboximidamide
Compound 25(E): (E)-2-(2-chloro-3-fluorobenzylidene)hydrazine-1-carboximidamide
Compound 26(E): (E)-2-(2,5-dichlorobenzylidene)hydrazine-1-carboximidamide
Compound 27(E): (E)-2-(2-chloro-3,4-difluorobenzylidene)hydrazine-1-carboximidamide
Compound 29(E): (E)-2-(2-chloro-3,5-difluorobenzylidene)hydrazine-1-carboximidamide
Compound 30(E): (E)-2-(3-chloro-2-fluorobenzylidene)hydrazine-1-carboximidamide
Compound 31(E): (E)-2-(2,3,6-trichlorobenzylidene)hydrazine-1-carboximidamide
Compound 32(E): (E)-2-(2-chloro-4,5-difluorobenzylidene)hydrazine-1-carboximidamide
Compound 34(E): (E)-2-(3,5-dichlorobenzylidene)hydrazine-1-carboximidamide In a preferred embodiment, the compound of formula IA is selected from compound 3, i.e. 2-(3,4,5-trichlorobenzylidene)hydrazine-1-carboximidamide, and compound 4, i.e. 2-(2,4,5-trichlorobenzylidene)hydrazine-1-carboximidamide, in particular the compound of formula IA is selected from (E)-2-(3,4,5-trichlorobenzylidene)hydrazine-1-carboximidamide and (E)-2-(2,4,5-trichlorobenzylidene)hydrazine-1-carboximidamide.

In one embodiment, the compound of formula IA is (E)-2-(3,4,5-trichlorobenzylidene)hydrazine-1-carboximidamide.

In another embodiment, the compound of formula IA is (E)-2-(2,4,5-trichlorobenzylidene)hydrazine-1-carboximidamide.

Compounds of formula IB may be selected from the following:
Compound 1(E): (E)-2-((4-chlorophenyl)methylene)hydrazine-1-carboximidamide
Compound 3(E): (E)-2-(3,4,5-trichlorobenzylidene)hydrazine-1-carboximidamide
Compound 4(E): (E)-2-(2,4,5-trichlorobenzylidene)hydrazine-1-carboximidamide
Compound 5(E): (E)-2-(3,5-dichloro-4-fluorobenzylidene)hydrazine-1-carboximidamide Compound 6(E): (E)-2-(2,3,4-trichlorobenzylidene)hydrazine-1-carboximidamide
Compound 7(E): (E)-2-(2,4-dichloro-5-fluorobenzylidene)hydrazine-1-carboximidamide
Compound 8(E): (E)-2-(4-chloro-3-fluorobenzylidene)hydrazine-1-carboximidamide
Compound 10(E): (E)-2-(2,3,5-trichlorobenzylidene)hydrazine-1-carboximidamide
Compound 11(E): (E)-2-(3,4-dichlorobenzylidene)hydrazine-1-carboximidamide
Compound 12(E): (E)-2-(2,4-dichlorobenzylidene)hydrazine-1-carboximidamide
Compound 13(E): (E)-2-(2,4-dichloro-3-fluorobenzylidene)hydrazine-1-carboximidamide
Compound 14(E): (E)-2-(2,3-dichloro-4-fluorobenzylidene)hydrazine-1-carboximidamide
Compound 15(E): (E)-2-(3-chloro-4-fluorobenzylidene)hydrazine-1-carboximidamide
Compound 17(E): (E)-2-(2-fluorobenzylidene)hydrazine-1-carboximidamide
Compound 18(E): (E)-2-(4,5-dichloro-2-fluorobenzylidene)hydrazine-1-carboximidamide
Compound 21(E): (E)-2-((2-chloropyridin-3-yl)methylene)hydrazine-1-carboximidamide
Compound 22(E): (E)-2-((2,6-dichloropyridin-3-yl)methylene)hydrazine-1-carboximidamide
Compound 23(E): (E)-2-(3-fluorobenzylidene)hydrazine-1-carboximidamide
Compound 24(E): (E)-2-(3-chlorobenzylidene)hydrazine-1-carboximidamide
Compound 25(E): (E)-2-(2-chloro-3-fluorobenzylidene)hydrazine-1-carboximidamide
Compound 26(E): (E)-2-(2,5-dichlorobenzylidene)hydrazine-1-carboximidamide
Compound 27(E): (E)-2-(2-chloro-3,4-difluorobenzylidene)hydrazine-1-carboximidamide
Compound 29(E): (E)-2-(2-chloro-3,5-difluorobenzylidene)hydrazine-1-carboximidamide
Compound 30(E): (E)-2-(3-chloro-2-fluorobenzylidene)hydrazine-1-carboximidamide
Compound 32(E): (E)-2-(2-chloro-4,5-difluorobenzylidene)hydrazine-1-carboximidamide In a preferred embodiment, the compound of formula IB is selected from compound 3, i.e. (E)-2-(3,4,5-trichlorobenzylidene)hydrazine-1-carboximidamide, and compound 4, i.e. (E)-2-(2,4,5-trichlorobenzylidene)hydrazine-1-carboximidamide.

In one embodiment, the compound of formula IB is (E)-2-(3,4,5-trichlorobenzylidene)hydrazine-1-carboximidamide.

In another embodiment, the compound of formula IB is (E)-2-(2,4,5-trichlorobenzylidene)hydrazine-1-carboximidamide.

In one embodiment, the compounds of formula IB inhibit PPP1R15A and PPP1R15B. Inhibition of PPP1R15A and PPP1R15B can be determined from binding analysis. For example, binding can be analysed using SPR (surface plasmon resonance) to obtain $K_D$ values. A PPP1R15A and PPP1R15B inhibitor may be defined as a compound where the difference in $K_D$ values between R15A and R15B is no more than about 3 fold. In particular, the difference in $K_D$ values between R15A and R15B is no more than about 2 fold. For example, the affinity for one target over the other is less than about 3 fold, in particular, less than about 2 fold. A "selective inhibitor" may be defined as a compound where the difference in $K_D$ values between R15A and R15B is greater than 3 fold, or even more preferably 10 or 20 fold.

In cells, the compounds of formula IB inhibit protein synthesis. Unlike Guanabenz, an R15A inhibitor which doesn't inhibit protein synthesis in untressed cells (Tsaytler et al., Science, 332, 91-94, 2011), or an R15B inhibitor which transiently inhibits protein synthesis, the combination of an R15A and R15B inhibitor leads to a persistent inhibition of protein synthesis (FIG. 12). Likewise, an inhibitor of R15A and R15B (compound 10) persistently inhibits protein synthesis (FIG. 12). ATF4 is induced by the inhibitor of R15A and R15B, confirming that the compounds are on-target (FIG. 13).

Described herein is the use of compounds of formula (I), or pharmaceutically acceptable salts thereof, as PPP1R15B selective inhibitors:

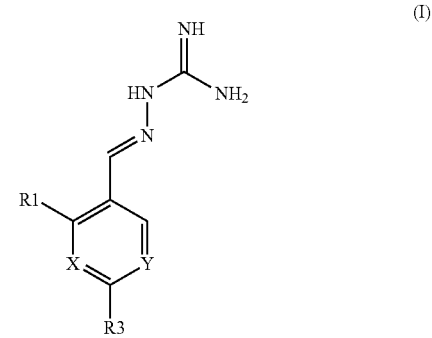

wherein
X is N or $CR^2$;
Y is N or $CR^4$;
$R^1$, $R^2$, $R^3$ and $R^4$ are independently selected from H, Cl or F;
with the proviso that:
when X is $CR^2$ and Y is $CR^4$ the compound of formula I is at least mono-substituted;
when $R^3$ is Cl, $R^2$ is not Cl;
when both $R^1$ and $R^4$ are Cl, $R^2$ is not Cl;
when the compound of formula I is di-substituted, X is $CR^2$, Y is $CR^4$ and $R^1$ is Cl, $R^3$ is not Cl;
when $R^4$ is Cl and the compound of formula I is di-substituted, $R^2$ is not Cl;
when $R^1$ is F, $R^2$ is not Cl;
when X or Y is N and the compound of formula I is mono-substituted, $R^1$ is not Cl;
when X is $CR^2$, Y is $CR^4$ and the compound of formula I is mono-substituted, $R^1$ is not F or Cl.

The PPP1R15B selective inhibitor, or a pharmaceutically acceptable salt thereof, may be selected from:

(Compound 16 (E))

Example 1

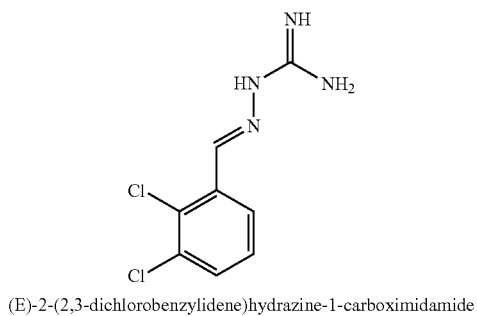

(E)-2-(2,3-dichlorobenzylidene)hydrazine-1-carboximidamide

Example 2

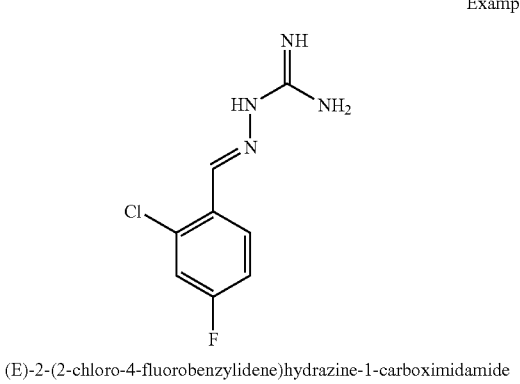

(E)-2-(2-chloro-4-fluorobenzylidene)hydrazine-1-carboximidamide

Salts and Esters

The compounds described herein can be present as salts or esters, in particular pharmaceutically acceptable salts or esters.

Pharmaceutically acceptable salts of the compounds described herein include suitable acid addition or base salts thereof. A review of suitable pharmaceutical salts may be found in Berge et al., J Pharm Sci, 66, 1-19 (1977). Salts which are not pharmaceutically or veterinarily acceptable may still be valuable as intermediates.

Esters are formed either using organic acids or alcohols/hydroxides, depending on the functional group being esterified.

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art. Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3rd edition, ed. March, J., John Wiley and Sons, New York, 1985).

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulfur, fluorine and chlorine such as $^{2}$H, $^{3}$H, $^{13}$C, $^{14}$C $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically acceptable salts thereof, for example, those in which a radioactive isotope such as $^{3}$H or $^{14}$C is incorporated, are useful in drug and/or substrate tissue distribution studies. Tritiated, i.e., $^{3}$H, and carbon-14, i.e., $^{14}$C, isotopes are particularly preferred for their ease of preparation and detectability. Further, substitution with isotopes such as deuterium, i.e., $^{2}$H, may afford certain therapeutic advantages resulting from greater metabolic stability, for example, increased in vivo half-life or reduced dosage requirements and hence may be preferred in some circumstances. For example, the invention includes compounds of formula I where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to any of the exemplified compounds in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Therapeutic Applications

The compounds described herein have potential therapeutic applications in treating and preventing various diseases and disorders.

One aspect of the invention relates to compounds of formula IA for use in therapy.

Another aspect of the invention relates to a method of treating a subject having a disorder associated with accumulation of misfolded proteins or perturbation of protein homeostasis, wherein the method comprises administering to the subject a therapeutically effective amount of a compound the invention.

Another aspect of the invention relates to a method of treating a subject having a disease state alleviated by the inhibition of PPP1R15A and PPP1R15B, wherein the method comprises administering to the subject a therapeutically effective amount of a compound the invention.

A further aspect of the invention relates a method of preventing a disorder associated with accumulation of misfolded proteins or perturbation of protein homeostasis in a subject, wherein the method comprises administering to the subject a therapeutically effective amount of a compound of the invention.

A further aspect of the invention relates a method of preventing a disease state alleviated by the inhibition of PPP1R15A and PPP1R15B in a subject, wherein the method comprises administering to the subject a therapeutically effective amount of a compound of the invention.

Another aspect of the invention relates to compounds of formula IA and formula IB for use in the treatment or prevention of a disorder associated with accumulation of misfolded proteins or perturbation of protein homeostasis.

Another aspect of the invention relates to compounds of formula IA and formula IB for use in the treatment or prevention of a disease state alleviated by the inhibition of PPP1R15A and PPP1R15B.

Yet another aspect of the invention relates to use of a compound of formula IA and IB in the manufacture of a medicament for the treatment or prevention of a disorder associated with accumulation of misfolded proteins or perturbation of protein homeostasis.

Yet another aspect of the invention relates to use of a compound of formula IA and IB in the manufacture of a medicament for the treatment or prevention of a disease state alleviated by the inhibition of PPP1R15A and PPP1R15B.

PPP1R15A and PPP1R15B related diseases are diseases that can be ameliorated by inhibiting PPP1R15A and PPP1R15B. These include disorders associated with accumulation of misfolded proteins or perturbation of protein homeostasis (proteostasis) such as Huntington's disease, Parkinson's disease, Alzheimer's disease, ataxias and other polyglutamine disorders as well as retinal degeneration, glaucoma, amyotrophic lateral sclerosis (ALS) and prion diseases; disorders associated with aggregation of the microtubule-associated protein tau and include Alzheimer's disease, amyotrophic lateral sclerosis and parkinsonism-dementia complex, argyrophilic grain disease, chronic traumatic encephalopathy, corticobasal degeneration, diffuse neurofibrillary tangles with calcification (DNTC), Down's syndrome, familial British dementia (FBD), familial Danish dementia (FDD), frontotemporal dementia and parkinsonism linked to chromosome 17 (FTDP-17), frontotemporal lobar degeneration (FTLD), Gerstmann-Sträussler-Scheinker disease, Gaudeloupean parkinsonism, myotonic dystrophy, neurodegeneration with brain iron accumulation, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, SLC9A6-related mental retardation, subacute sclerosing panencephalitis, tangle-only dementia, and white matter tauopathy with globular glial incluıdsions; myelin disorders, such as multiple sclerosis, Pelizaeus-Merzbacher disease, vanishing white matter disease, acute disseminated encephalomyelitis, periventricular leukomalacia, periventricular white matter injury, Tabes Dorsalis, Devic's disease, optic neuritis, progressive multifocal leukoencephalopathy, transverse myelitis, chronic inflammatory demyelinating polyneuropathyl, anti-MAG peripheral neuropathy, adrenoleukodystrophy, adrenomyeloneuropathy, diffuse white matter injury, Guillain-Barre Syndrome, central pontine myelinolysis, inherited demyelinating diseases such as leukodystrophy, and Charcot Marie Tooth disease; diseases caused by the misfolding or trafficking defects of any protein made in the endoplasmic reticulum (ER), such as cystic fibrosis, congenital hypothyroid goieter, familial neurohypophyseal diabetes, procollagen biosynthesis disorders including osteogenesis imperfect, hypercholesterolemia, alpha-1 antitrypsin deficiencies, lysomal disorder, retinis pigmentosa (RP), and inflammatory bowel disease; metabolic diseases, such as diabetes, Wolcott-Rallison syndrome, obesity, insulin resistance, hyperlipidemia, fatty liver disease and atherosclerosis; cancer; aging; inflammation; and other disorders including rheumatoid arthritis, type-1 diabetes and vitiligo.

In one preferred embodiment, the compounds described herein are for use in treating disorders associated with pathological UPR or ISR and/or defects in protein homeostasis.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "therapeutically effective amount" refers to that amount of the compound being administered which will relieve to some extent one or more of the symptoms of the disease of disorder being treated.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

The phrase "manufacture of a medicament" includes the above described compound directly as the medicament in addition to its use in a screening programme for further active agents or in any stage of the manufacture of such a medicament.

Diseases with Potential Protein or Peptide Misfolding and/or Aggregation in their Mode of Action Disease-causing proteins are expressed throughout life but degenerative diseases are mostly late-onset. This suggests that the different disease-causing proteins gradually become detrimental over time. While it is now well established that misfolded proteins cause distinct degenerative diseases, why they accumulate remains largely unclear. Cells normally strive to ensure that proteins are correctly folded and indeed all cells have powerful and sophisticated protein quality control systems that very efficiently handle potentially harmful proteins for decades. However, the protein quality control mechanisms seem to gradually fail with age, leading to the accumulation of misfolded proteins with the resulting catastrophic consequences for cells and organisms. These misfolded/aggregated proteins or peptides can be present inside or outside the cell and can be found at any location. In principle, boosting the natural cellular defences against misfolded proteins should represent a generic approach to reduce the pathology in diverse protein misfolding diseases where misfolded/aggregation prone proteins are present in the pathology. The present invention describes such an approach and demonstrates both its safety and efficacy in a mammal.

Neurodegenerative diseases such as Alzheimer's disease (AD), Parkinson's disease (PD), Huntington's disease (HD), ataxias and other polyglutamine disorders, tauopathies as well as, retinal degeneration, glaucoma, amyotrophic lateral sclerosis (ALS) and prion diseases are devastating and affect an increasing number of individuals in the ageing population. These diseases are clinically diverse but share a common mechanism. They are caused by the progressive dysfunction and death of specific nerve cells in selective regions of the brain due to the accumulation of specific proteins of aberrant shape. The misfolded and aggregation prone proteins include, but are not restricted to: AJ342, α-synuclein, TAU, TDP-43, TLS/FUS, SOD1, Huntingtin and other proteins with polyglutamine expansion, prions and the translation product(s) of C90RF72.

The Applicant has demonstrated that the compound of Example 1 selectively inhibits PPP1R15B-PP1, correcting a protein misfolding disease in mice. Inhibitors of PPP1R15B described herein therefore have therapeutic applications in the treatment of a variety of diseases where a misfolded protein is involved and in particular with an accumulation of misfolded proteins. Inhibitors of PPP1R15A and PPP1R15B, such as the compounds of formula IB, are also expected to have application in the treatment of diseases where a misfolded protein is involved.

The present invention provides for the therapy of polyglutamine disorders. Huntington's disease belongs to a broader group of disorders, "polyglutamine disorders", characterized by expansion of CAG codons translated in glutamine in unrelated proteins. Huntington's disease is caused by an expansion in the gene encoding Huntingtin; Spinal and bulbar muscular atrophy, Dentalorubral-pallidoluysian atrophy, and Spinocerebellar ataxias are caused by expansion in genes encoding Androgen Receptor, Atrophin 1, Ataxin 1, 2, 3, α-voltage dependent calcium channel subunit and TBP respectively. CAG expansion is translated in polyglutamine and causes aggregation of the affected protein. Accordingly, prevention and/or treatment of polyglutamine disorders such as these are within the scope of the invention.

As an example, the Applicant has shown that the compound of Example 1 ameliorates Huntington's disease in a mammal. Thus, without wishing to be bound by theory, it is believed that an inhibitor of PPP1R15B has a protective effect against diverse diseases caused by misfolded/aggregated proteins such as but not restricted to Alzheimer's disease (AD), Parkinson's disease (PD), Huntington's disease (HD), ataxias and other polyglutamine disorders as well as, retinal degeneration, glaucoma, Amyotrophic Lateral Sclerosis (ALS), tauopathies and prion diseases. Inhibitors of PPP1R15A and PPP1R15B, such as the compounds of formula IB, are expected to have the same effect.

The diseases include any diseases where misfolding/aggregation is involved with the proteins known today and described above but will also apply to new proteins and perhaps new diseases in the future.

In a preferred embodiment, the invention provides for the therapy of proteostasis diseases.

In another embodiment, the compounds described herein are for use in treating a disease where accumulation of misfolded proteins is involved in the mode of action.

In a further embodiment, the disease or disorder is Alzheimer's disease (AD), Parkinson's disease (PD), Huntington's disease (HD), ataxias or other polyglutamine disorder, retinal degeneration, glaucoma, Amyotrophic Lateral Sclerosis (ALS), tauopathies or a prion disease.

In a particular embodiment, the compounds described herein are for use in the treatment of Huntington's disease.

In another particular embodiment, the compounds described herein are for use in the treatment of Parkinson's disease.

In one embodiment, the disease or disorder is associated with aggregation of the microtubule-associated protein tau.

The Applicant has demonstrated that the compound of Example 1 selectively inhibits PPP1R15B-PP1, correcting a protein misfolding disease in mice. PPP1R15B inhibitors can also be useful to prevent or stop the progression of diseases that are caused by the same mechanism: accumulation of misfolded proteins. Inhibitors of PPP1R15A and PPP1R15B, such as the compounds of formula IB, are also expected to have this application.

Examples of such diseases include, Alzheimer's disease, amyotrophic lateral sclerosis and, parkinsonism and dementia, argyrophilic grain disease, chronic traumatic encephalopathy, corticobasal degeneration, diffuse neurofibrillary tangles with calcification (DNTC), Down's syndrome, familial British dementia (FBD), familial Danish dementia (FDD), frontotemporal dementia and parkinsonism linked to chromosome 17 (FTDP-17) (caused by MAPT mutations), frontotemporal lobar degeneration (FTLD) (some cases caused by C90RF72 mutations), Gerstmann-Sträussler-Scheinker disease, Gaudeloupean parkinsonism, myotonic dystrophy, neurodegeneration with brain iron accumulation, Niemann-Pick disease, type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, SLC9A6-related mental retardation, subacute sclerosing panencephalitis, tangle-only dementia, white matter tauopathy with globular glial inclusions.

In one embodiment, the disease is a myelin disorder.

Myelin is an abundant protein of both the central and peripheral nervous system. It is produced by two cell types: oligodendrocytes in the central nervous system and Schwann cells in the peripheral nervous system. Myelin forms a sheath around axons to insure the speed of conduction of electrical impulses along an axon, and to prevent electrical current from dissipating from the axon. Myelin function is essential for the nervous system.

Myelin disorders affect more than 2.5 million people worldwide and are defined as any disease associated with damage in myelin. Myelin disorders are manifested by diverse symptoms including but not restricted to motor impairments, sensory impairments, cognitive dysfunction, emotional disturbances, and impaired coordination.

There are many demyelinating disorders, the most common of which is multiple sclerosis (MS). Multiple sclerosis is an autoimmune disease affecting the brain and spinal cord resulting in demyelination in the brain. In addition to MS, other demyelinating disorders include but are not limited to Pelizaeus-Merzbacher disease and vanishing white matter disease, acute disseminated encephalomyelitis, periventricular leukomalacia, periventricular white matter injury, Tabes Dorsalis, Devic's disease, optic neuritis, progressive multifocal leukoencephalopathy, transverse myelitis, chronic inflammatory demyelinating polyneuropathy, anti-MAG peripheral neuropathy, adrenoleukodystrophy, adrenomyeloneuropathy, diffuse white matter injury, Guillain-Barre Syndrome, central pontine myelinolysis, inherited demyelinating diseases such as leukodystrophy, and Charcot Marie Tooth (CMT) disease.

CMT disease is a group of myelin neuropathies caused by mutations in a number of genes. Mutations in the peripheral myelin protein PMP22 are the most common causes of CMT. A mutation in PMP22 (Trembler-J) causes the misfolding of PMP22 and results in a disease in mice that resembles CMT in human due to defects in myelin in the peripheral nervous system. The Applicants have demonstrated that the compound of Example 1 can improve myelination in explants from neuropathic mice. The Applicants have demonstrated that improving myelination in explants from neuropathic mice predicts efficacy in a mammal (Das et al. Science, 2015). Therefore the compound of Example 1 will be useful in treating CMT in mammals and other myelin disorders where it is known that the mechanisms are similar and involve the elF2α pathway (Lin and Popko, Nat. Neurosci., 12, 379-385, 2009) and is anticipated that inhibitors of PPP1R15A and PPP1R15B, such as the compounds of formula (I), will also be useful in treating CMT.

In one embodiment, the compounds described herein are for use in treating a myelin disorder.

In another embodiment, the compounds described herein are for use in treating Charcot Marie Tooth disease.

In a further embodiment, the compounds described herein are for use in treating myelin disorders of the central nervous system, for example, multiple sclerosis. It is known that the mechanisms of CMT and MS are similar with an exhaustion of myelin producing cells (Schwann cells in CMT and oligodendrecytes in MS) and involve pathological signalling of the elF2α-RRR1R15A pathway (Lin and Popko, Nat. Neurosci., 12, 379-385, 2009). Since the Applicants have demonstrated that Example 1 is effective in a myelinopathy and have also demonstrated the bioavailability of a compound of Example 1 in both the central and peripheral nervous system (FIG. 5), it is anticipated that PPP1R15B inhibitors, and inhibitors of PPP1R15A and PPP1R15B such as the compounds of formula IB, will be useful in treating multiple sclerosis.

In one embodiment, the disease is a disease arising as a consequence of a mutation in a protein resulting in its misfolding and mislocalisation or trafficking defects.

The Applicants have demonstrated that the compound of Example 1 can rescue defects caused by one misfolded protein, PMP22, synthetized in the endoplasmic reticulum (ER). Due to the mechanism of action (decreasing translation to increase folding) an inhibitor of PPP1R15B, and an inhibitor of PPP1R15A and PPP1R15B, will also be useful for the treatment of diseases due to the misfolding or trafficking defects of any protein made in the ER, including transmembrane or secreted proteins.

Examples of such diseases include: cystic fibrosis caused by mutations impairing folding of the transmembrane protein (CFTR); congenital hypothyroid goitre with thyroglobulin deficiency due to the misfolding and/or trafficking defect of the hormone thyroglobulin; familial neurohypophyseal diabetes insipidus caused by misfolding and absence of circulating arginine vasopressin (this may also include certain forms of genetically inherited nephrogenic diabetes insipidus); procollagen biosynthesis disorders where the disease is caused by a failure to fold, assemble and synthetize collagen, such as, but not restricted to, osteogenesis imperfect; more generally, any genetic diseases of connective tissues where protein misfolding/lack of synthesis or mislocalization is in the mode of action such as growth plate dysplasia associated with defects of proteins from extracellular matrix; hypercholesterolemia, with molecular defects caused by mutations in the LDL receptor causing lack of synthesis, altered intracellular transport, or abnormal function; Alpha-1 antitrypsin deficiencies due to the misfolding of alpha 1 antitrypsin; lysomal disorder due to misfolding of proteins associated for lysosomal function such as Gaucher disease and Niemann-Pick disease and Anderson-Fabry disease; retinis pigmentosa (RP), which is the most common form of hereditary retinal degeneration caused by the misfolding of rhodopsin proteins, their ER retention and the resulting ER stress and cell death; and inflammatory bowel disease which is associated with ER stress.

For the same reasons, an inhibitor of PPP1R15B or an inhibitor of PPP1R15A and PPP1R15B, such as the compounds of formula IB, can be used to treat the following disorders, associated with pathological UPR and/or defects in a transmembrane protein (Lin and Popko, Nat. Neurosci., 12, 379-385, 2009). These disorders include, but are not restricted to Pelizaeus-Merzbacher disease associated with mutations in the membrane proteolipid protein (PLP) gene, and vanishing white matter (VWM) disease as well as multiple sclerosis, a common myelin disorder.

In one embodiment, the compounds described herein are for use in the treatment of diseases arising from a mutation in a protein resulting in the protein's misfolding and mislocalisation or trafficking defects.

In a another embodiment, the disease arising from a mutation in a protein resulting in the protein's misfolding and mislocalisation or trafficking defects is selected from cystic fibrosis, congenital hypothyroid goitre, familial neurohypophyseal diabetes insipidus, procollagen biosynthesis disorders such as osteogenesis, hypercholesterolemia, alpha-1 antitrypsin deficiencies, lysomal disorders such as Gaucher disease, Niemann-Pick disease and Anderson-Fabry disease, retinis pigmentosa and inflammatory bowel disease.

In one embodiment, the disease is a metabolic disease.

It is known that metabolic diseases such as diabetes, obesity, insulin resistance, hyperlipidemia, fatty liver disease, and atherosclerosis are associated with pathological ER stress and it is believed that pharmacological modulators of the UPR may have therapeutic benefit (Cao and Kaufman, 2012, Curr Biol, vol. 22 (16)). However, as no PPP1R15B inhibitors were previously available and PPP1R15B inhibition was predicted to be deleterious, and furthermore, since it is challenging to inhibit phosphatases, it was unclear whether PPP1R15B could be a therapeutic target in metabolic diseases.

The inventors have demonstrated that the compound of Example 1 can ameliorate a metabolic disorder in a mammal (FIG. 11). Therefore, PPP1R15B inhibitors will be useful to treat metabolic disorders such as, but not restricted to diabetes, obesity, fatty liver disease, and atherosclerosis. It is also expected that inhibitors of PPP1R15A and PPP1R15B, such as the compounds of formula (I), will also be useful in treating metabolic disorders.

In one embodiment, the compounds described herein are for use in the treatment of metabolic disorders.

In a preferred embodiment, the metabolic disorder is selected from diabetes, obesity, fatty liver disease, and atherosclerosis.

PPP1R15B selective inhibitors are also useful in the treatment of other disorders including rheumatoid arthritis, diabetes, Wolkott Rallison syndrome, inflammatory bowel disease and vitiligo, which involve UPR in their mechanism of action (Cao and Kaufman, 2012, Curr Biol, vol. 22 (16)). PPP1R15A and PPP1R15B inhibitors, such as the compounds of formula (I) are also expected to be useful in treatment of these disorders.

Cancer

In one embodiment, a compound described herein is for use in treating cancer.

Cancer cells have high metabolic requirement and their proliferation relies on efficient protein synthesis. Translation initiation plays a crucial role in controlling protein homeostasis, differentiation, proliferation and malignant transformation. Increasing translation initiation contributes to cancer initiation and conversely, decreasing translation initiation could reduce tumor growth (Donze et al., 1995, EMBO J, 14, 3828-34; Pervin et al., 2008, Cancer Res, 68, 4862-74; Chen et al., 2011, Nat Chem Biol, 7, 610-6). Without wishing to be bound by theory, it is believed that inhibiting PPP1R15A and PPP1R15B could reduce translation in tumor cells and thus reduce tumor growth.

Aging

There is abundant literature showing that reducing protein synthesis increases life span (Tavernarakis, 2008, Trends Cell Biol, 18(5), 228-235. Therefore it is reasonable to predict that reducing protein synthesis by inhibiting PPP1R15A and PPP1R15B will increase life-span.

Inflammation

Salubrinal is an inducer of eIF2α phosphorylation and is thought to inhibit R15A and R15B phosphatases by an unknown mechanism. Salubrinal was found to suppress inflammation (Hamamura et al., 2015, Cellular Signalling, 27(4), 828-835). However, Salubrinal cannot be used in human due to toxicity issues. It is reasonable to anticipate that the R15A/B inhibitors disclosed here will be a potential therapy for diseases involving inflammation.

A non exhaustive set of examples of diseases associated with inflammation are: arthritis, ulcerative colitis and inflammatory bowel disease, infections associated with inflammation, fibrosis, neurodegenerative diseases associated with inflammation or broadly any human diseases associated with inflammation.

In particular, diseases associated with inflammation include: rheumatoid arthritis; multiple sclerosis; inflammatory bowel disease (IBD), which is a term mainly used to describe two conditions, ulcerative colitis and Crohn's disease; diabetes; lupus nephritis; autoimmune inner ear disease (AIED); cystic fibrosis; Graves disease; myocarditis; autoimmune hepatitis; Alzheimer's disease; Parkinson's disease; scleroderma; Gall Bladder Disease; Hashimoto's Thyroiditis; autoimmune reaction originating in the gut triggered by antibodies against thyroid enzymes and proteins; Guillain-Barre autoimmune attack of the nervous system often triggered by autoimmune response to external stressors such as vaccinations; Polymyalgia Rheumatica; leukemia; and asthma.

Anti-Viral Agents

The compounds described herein may be used as antiviral agents. Protein synthesis is required for viral replication. Having shown that AB inhibitors inhibit protein synthesis, it is reasonable to anticipate that they will block viral replication and be useful to prevent infectious disease in human. Indeed, by way of example, it has been previously shown that salubrinal, an inducer of eIF2α phosphorylation blocks the replication of Herpex simplex virus (Boyce, M., et al. (2005) Science 307(5711), 935-939). However, Salubrinal cannot be used in human due to toxicity issues. Therefore, the R15A/B inhibitors disclosed herein may have a therapeutic advantage over other translation inhibitors.

The Applicants have shown that a PPP1R15B inhibitor can prevent Huntington's disease. PPP1R15B is constitutively expressed and is therefore a more broadly applicable disease target. It is reasonable to anticipate that AB inhibitors administered at a dose such that targets are only inhibited by short pulses will prevent most (if not all) protein misfolding diseases.

Pharmaceutical Compositions

According to a further aspect of the invention there is provided a pharmaceutical composition comprising a compound described herein for use in therapy combined with any pharmaceutically acceptable carrier, adjuvant or vehicle.

The term "pharmaceutical composition" in the context of this invention means a composition comprising an active agent and additionally one or more pharmaceutically acceptable excipients.

Suitable pharmaceutically acceptable excipients are known to those skilled in the art and generally include an acceptable composition, material, carrier, diluent or vehicle suitable for administering a compound of the invention to an animal.

In one embodiment the animal is a mammal. In another embodiment the mammal is human.

Pharmaceutical formulations include those suitable for oral, topical (including dermal, buccal, ocular and sublingual) rectal or parenteral (including subcutaneous, intradermal, intramuscular and intravenous), nasal, intra-ocularly and pulmonary administration e.g., by inhalation. The formulation may, where appropriate, be conveniently presented in discrete dosage units and may be prepared by any of the methods well known in the art of pharmacy.

Dosages may be varied depending on the requirements of the patient, the severity of the condition being treated and the characteristics of the active ingredient being employed. Determination of the effective dose is within the remit of the skilled person, without undue burden. Suitable dosage forms for administration to mammals, including humans are typically in the range of up to 100 mg/kg body weight, or may be 0.1 mg/kg, 10 mg/kg, 20 mg/kg, 30 mg/kg for example.

According to a further aspect of the invention, there is provided a process for the preparation of a pharmaceutical composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound disclosed herein in conjunction or association with a pharmaceutically acceptable carrier or vehicle. All methods include the step of bringing into association an active compound with liquid carriers or finely divided solid carriers or both and then, if necessary, shaping the product into the desired formulation.

Combinations

In a particularly preferred embodiment, the one or more compounds of the invention are administered in combination with one or more other active agents, for example, existing drugs available on the market. In such cases, the inhibitors of the invention may be administered consecutively, simultaneously or sequentially with the one or more other active agents.

Combining a compound which is a R15A inhibitor with a compound which is a R15B inhibitor results in the same advantageous properties as a compound which inhibitors both R15A and R15B. Therefore, one aspect of the present invention provides a combination of a R15A inhibitor compound and a R15B inhibitor compound. The combination is useful in the treatment of a disease state alleviated by the inhibition of PPP1R15A and PPP1R15B, for example, a disorder associated with accumulation of misfolded proteins or proteostatsis disorder. The combination may be guanabenz, a known R15A inhibitor, and (E)-2-(2,3-dichlorobenzylidene)hydrazine-1-carboximidamide (compound 16), a R15B inhibitor.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of resistance.

Beneficial combinations may be suggested by studying the inhibitory activity of the test inhibitors with agents known or suspected of being valuable in the treatment of a particular disorder. This procedure can also be used to determine the order of administration of the agents, i.e. before, simultaneously, or after delivery. Such scheduling may be a feature of all the active agents identified herein.

EXAMPLES

Preparation of the Compounds According to the Present Invention

The compounds according to the present invention can be prepared according to the following procedures, which are shown in respect of the E isomeric forms. From these methods it will be known to the skilled person how other isomeric forms, or the racemate, could be obtained.

Compound 1—(E)-2-((4-chlorophenyl)methylene)hydrazine-1-carboximidamide

Synthetic Scheme:

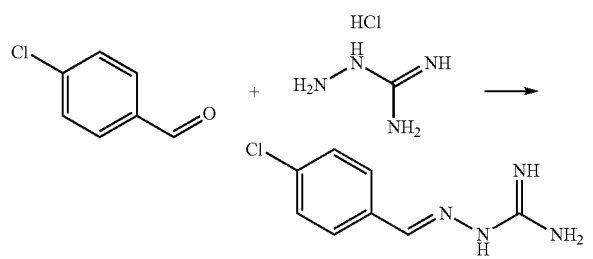

Experimental Details

Calculation:

| | Chemicals | Quantity | M.W. | Mole | Mole ratio |
|---|---|---|---|---|---|
| 1 | 4-chlorobenzaldehyde | 0.060 g | 140.57 | 0.00042 | 1.00 |
| 2 | Aminoguanidine hydrochloride | 0.047 g | 110.55 | 0.00042 | 1.00 |

-continued

| | Chemicals | Quantity | M.W. | Mole | Mole ratio |
|---|---|---|---|---|---|
| 3 | Sodium acetate | 0.034 g | 82.03 | 0.00042 | 1.00 |
| 4 | Ethanol | 1 ml | | | |

Procedure:

To a solution of 4-chlorobenzaldehyde (0.060 g, 0.00042 mol) in ethanol (1 ml) was sequentially added Aminoguanidine hydrochloride (0.047 g, 0.00042 mol) and Sodium acetate (0.034 g, 0.00042 mol) at 25° C. The resulting reaction mixture was heated at 80° C. for next 6 hours. Reaction completion was monitored on TLC using dichloromethane/methanol (8/2) as mobile phase. After completion of reaction, the reaction mixture was allowed to cool down to 25° C. and dumped in a saturated solution of NaHCO$_3$ (10 ml). The resulting precipitates were filtered off under vacuum and washed with water (5 ml). The resulting solid material was triturated with diethyl ether (2×2 ml) and dried under vacuum to provide the titled compound (0.040 g, 47.8% yield).

Compound 2—(E)-2-((2,4-dichloropyrimidin-5-yl)methylene)hydrazine-1-carboximidamide Reaction Scheme:

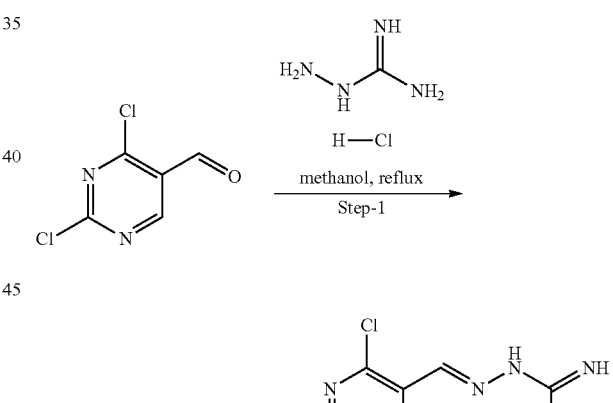

Experimental Details

To a solution of Compound-14 (0.1 g, 0.56 mmol) in methanol (2 mL) was added amino guanidine hydrochloride (0.50 g, 0.45 mmol). The reaction mixture was stirred for 2 h at 65-70° C. The reaction showed 80% conversion on TLC. Reaction mixture was concentrated under reduced pressure to provide crude product which was stirred with ethyl acetate (30 mL) to give solid material which was filtered out and then dried under vacuum. Obtained solid material was further purified by Prep HPLC purification to afford the title compound as yellow solid (0.028 g, 27.12%).

Compound 3—(E)-2-(3,4,5-trichlorobenzylidene)hydrazine-1-carboximidamide

Synthetic Scheme:

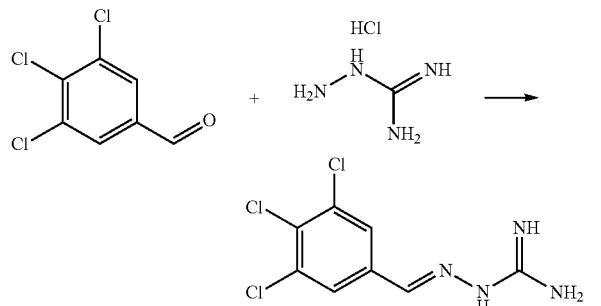

Experimental Details

Calculation:

| | Chemicals | Quantity | M.W. | Mole | Mole ratio |
|---|---|---|---|---|---|
| 1 | 3,4,5-trichlorobenzaldehyde | 0.040 g | 207.92 | 0.00019 | 1.00 |
| 2 | Aminoguanidine hydrochloride | 0.021 g | 110.55 | 0.00019 | 1.00 |
| 3 | Sodium acetate | 0.015 g | 82.03 | 0.00019 | 1.00 |
| 4 | Ethanol | 1 ml | | | |

Procedure:

To a solution of 3,4,5-trichlorobenzaldehyde (0.040 g, 0.00019 mol) in ethanol (1 ml) was sequentially added amino guanidine hydrochloride (0.021 g, 0.00019 mol) and sodium acetate (0.015 g, 0.00019 mol) at 25° C. The resulting reaction mixture was heated at 80° C. for next 6 hours. Reaction completion was monitored on TLC using dichloromethane/methanol (8/2) as mobile phase. After completion of reaction, the reaction mixture was allowed to cool down to 25° C. and dumped in a saturated solution of $NaHCO_3$ (10 ml). The resulting precipitates were filtered off under vacuum and washed with water (5 ml). The resulting solid material was triturated with diethyl ether (2×2 ml) and dried under vacuum to provide the title compound (0.036 g, 70.88% yield). 1H-NMR (DMSO-d6): □ (ppm) 7.96 (s, 2H); 7.89 (s, 1H); 6.20 (brs, 2H); 5.69 (brs, 2H); MS (ESI+): m/z=265.1 $[M+H]^+$

Compound 4—(E)-2-(2,4,5-trichlorobenzylidene)hydrazine-1-carboximidamide

Synthetic Scheme:

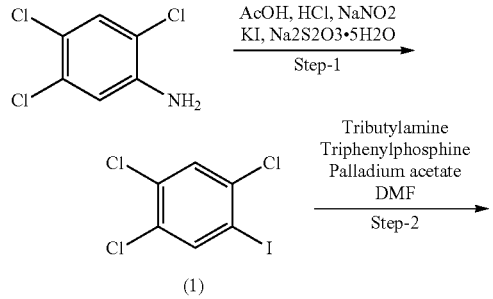

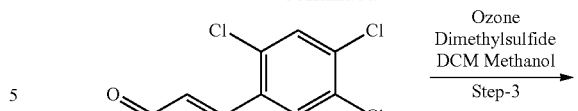

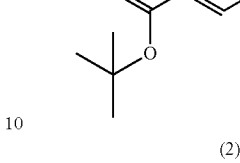

(2)

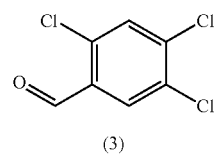

(3)

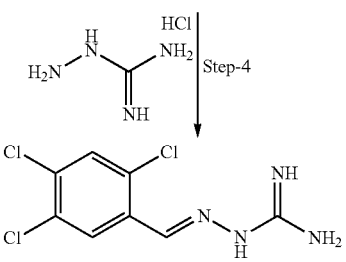

Experimental Details

Synthesis of 1,2,4-trichloro-5-iodobenzene [Intermediate-1]

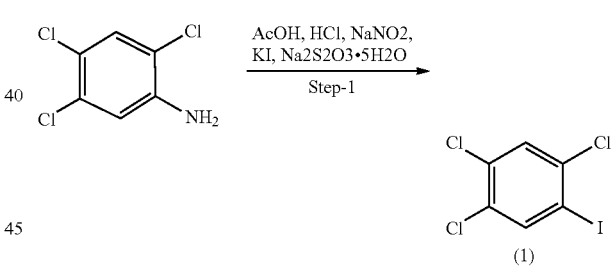

Calculation:

| | Chemicals | Quantity | M.W. | Mole | Mole ratio |
|---|---|---|---|---|---|
| 1 | 2,4,5-trichloroaniline | 4.00 g | 194.94 | 0.02051 | 1.00 |
| 2 | $NaNO_2$ | 1.41 g | 69 | 0.02051 | 1.00 |
| 3 | KI | 3.74 g | 166 | 0.02251 | 1.10 |
| 4 | $Na_2S_2O_3 \cdot 5H_2O$ | 1.50 g | 248.1 | 0.00610 | 0.30 |
| 5 | Acetic acid | 80 ml | | | |
| 6 | Conc. HCl | 4 ml | | | |
| 7 | D.M.Water | 4.8 ml | | | |

Procedure:

A suspension of 2,4,5-trichloroaniline (4.00 g, 0.02051 mol) in acetic acid (80 ml) was heated at 35° C. till the mixture became clear. After that the resulting reaction mixture was allowed to cool down to 25° C. Concentrated HCl (4 ml) was added in to the reaction mixture at 25° C. and the reaction mixture was stirred for next 30 minutes at the same temperature. There after a solution of NaNO₂ (1.41 g, 0.02051 mol) in D.M. water (4.8 ml) was added in to the reaction mixture at 25° C. and the resulting reaction mixture was stirred for 30 minutes at the same temperature. The insoluble material was removed by filtration and washed with acetic acid (3×15 ml). KI (3.74 g, 0.02251 mol) was added in to the combined clear filtrate at 25° C. The resulting mixture was stirred at 25° C. for 30 minutes, thereafter Na₂S₂O₃.5H₂O (1.50 g, 0.00610) was added in to the reaction mixture which was further stirred at 25° C. for 30 minutes. The final insoluble solids in the reaction mixture material were removed by filtration and was washed with acetic acid (3×10 ml). The combined clear filtrate was evaporated to dryness to get Intermediate-1 (5 g, 79.6% yield) which was used for the next step without any further processing.

Synthesis of tert-butyl (E)-3-(2,4,5-trichlorophenyl)acrylate [Intermediate-2]

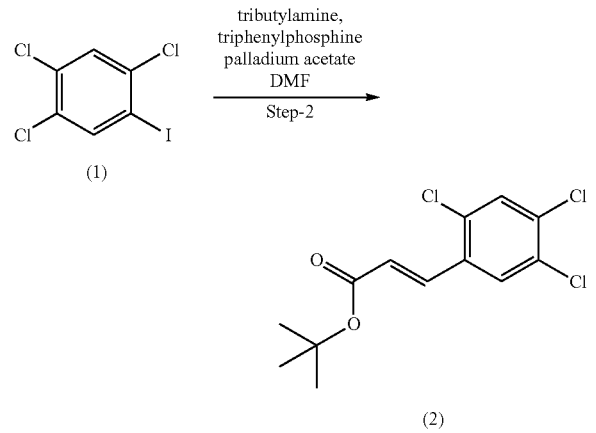

Calculation:

| | Chemicals | Quantity | M.W. | Mole | Mole ratio |
|---|---|---|---|---|---|
| 1 | Intermediate-1 | 5.00 g | 305.82 | 0.01634 | 1.00 |
| 2 | Tert butyl acrylate | 8.30 g | 128.1 | 0.06539 | 4.00 |
| 3 | Tri butylamine | 9.00 g | 185.3 | 0.04904 | 3.00 |
| 4 | Triphenylphosphine | 0.42 g | 262.2 | 0.00162 | 0.10 |
| 5 | Palladium (II)Acetate | 0.73 g | 224.0 | 0.00325 | 0.20 |
| 6 | DMF | 30 ml | | | |

Procedure:

To a solution of Intermediate-1 (5.00 g, 0.01634 mol) in DMF (30 ml) were sequentially added Tert butyl acrylate (8.30 g, 0.06539 mol), Tri butylamine (9.00 g, 0.04904 mol), Triphenylphosphine (0.42 g, 0.00162 mol) and Palladium (11) Acetate (0.73 g, 0.00325 mol) at 25° C. The resulting reaction mixture was heated at 80° C. for next 3 hours. Reaction completion was monitored on TLC using n-hexane/ethyl acetate (9/1) as mobile phase. After completion of reaction, the reaction mixture was allowed to cool down to 25° C. The resulting reaction mixture was evaporated to dryness. The resulting residue was suspended in to D.M. water (200 ml) and extracted by ethyl acetate (3×250 ml). The resulting combined organic layer was washed with brine (100 ml), dried over Na₂SO₄ and concentrated under vacuum to get desired Intermediate-2 (3.3 g, 65.96% yield) which was used for the next step without any further processing.

Synthesis of 2,4,5-trichlorobenzaldehyde [Intermediate-3]

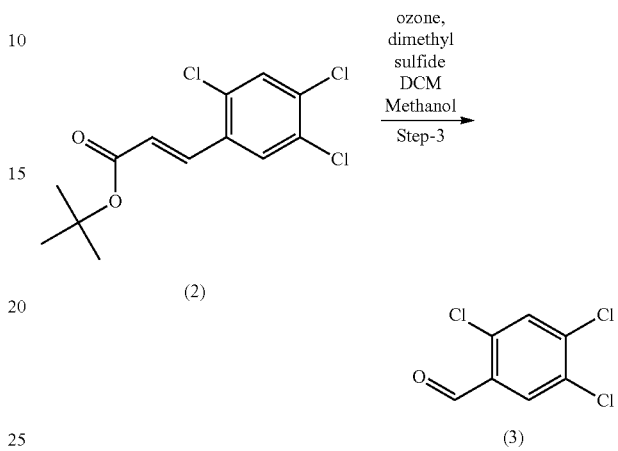

Calculation:

| | Chemicals | Quantity | M.W. | Mole | Mole ratio |
|---|---|---|---|---|---|
| 1 | Intermediate-2 | 0.25 g | 306 | 0.00081 | 1.00 |
| 2 | Dimethyl sulfide | 0.32 ml | | | |
| 3 | DCM | 30 ml | | | |
| 4 | Methanol | 20 ml | | | |

Procedure:

Intermediate-2 (0.25 g, 0.00081 mol) was taken up in a mixture of methanol:dichloromethane (2:3) (50 ml) and the reaction mixture was cooled to −78° C. with the help of a dry ice/acetone bath. Ozone gas was purged in to the reaction mixture at −78° C. till the reaction became blue. After that Oxygen gas was purged in to the reaction mixture for 10 minutes at −78° C. followed by addition of Dimethyl sulfide (0.32 ml) at −78° C. The resulting reaction mixture was then allowed to warm to room temperature and allowed to stir for 10 minutes. Reaction completion was monitored on TLC using n-hexane/ethyl acetate (9/1) as mobile phase. After completion of reaction, the reaction mixture was evaporated to dryness. The resulting residue was suspended in to the D.M. water (50 ml) and extracted by diethyl ether (3×20 ml). The resulting combined organic layer was dried over Na₂SO₄ and concentrated under vacuum to get desired Intermediate-3 (0.25 g, quantitative) which was used for the next step without any further processing.

Synthesis of (E)-2-(2,4,5-trichlorobenzylidene)hydrazine-1-carboximidamide

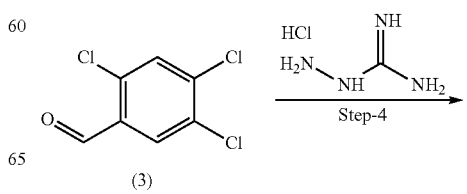

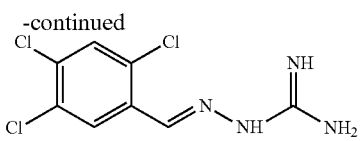

Calculation:

| | Chemicals | Quantity | M.W. | Mole | Mole ratio |
|---|---|---|---|---|---|
| 1 | Intermediate-3 | 0.040 g | 207.92 | 0.00019 | 1.00 |
| 2 | Aminoguanidine hydrochloride | 0.021 g | 110.55 | 0.00019 | 1.00 |
| 3 | Sodium acetate | 0.015 g | 82.03 | 0.00019 | 1.00 |
| 4 | Ethanol | 1 ml | | | |

Procedure:

To a solution of Intermediate-3 (0.040 g, 0.00019 mol) in ethanol (1 ml) was sequentially added amino guanidine hydrochloride (0.021 g, 0.00019 mol) and sodium acetate (0.015 g, 0.00019 mol) at 25° C. The resulting reaction mixture was heated at 80° C. for next 6 hours. Reaction completion was monitored on TLC using dichloromethane/methanol (8/2) as mobile phase. After completion of reaction, the reaction mixture was allowed to cool down to 25° C. and dumped in a saturated solution of $NaHCO_3$ (10 ml). The resulting precipitates were filtered off under vacuum and washed with water (5 ml). The resulting solid material was triturated with diethyl ether (2×2 ml) and dried under vacuum to provide the title compound (0.04 g, 78.76% yield). $^1$H-NMR (DMSO-$d_6$): δ (ppm) 8.43 (s, 1H); 8.12 (s, 1H); 7.77 (s, 1H); 6.33 (brs, 2H); 5.83 (brs, 2H); MS (ESI+): m/z=265.17 $[M+H]^+$

Compound 5—(E)-2-(3,5-dichloro-4-fluorobenzylidene)hydrazine-1-carboximidamide Synthetic Scheme:

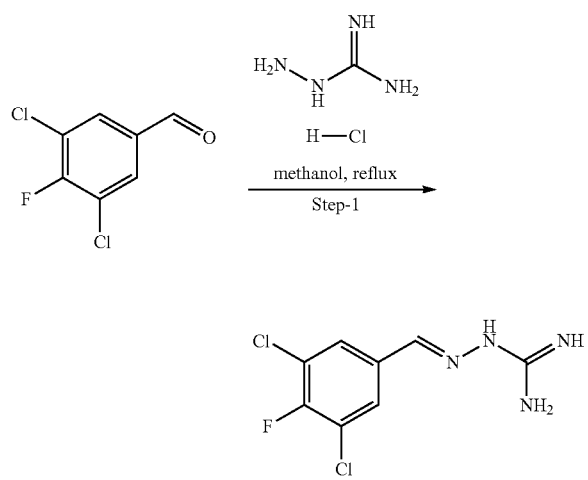

Experimental Details:

To a solution of 3,5-chloro-4-fluorobenzaldehyde (0.1 g, 0.52 mmol) in methanol (2 mL) was added amino guanidine hydrochloride (0.048 g, 0.43 mmol). The reaction was stirred for 2 h at 65-70° C. The reaction showed 80% conversion on TLC. Reaction mixture was cooled and concentrated under reduced pressure to provide crude product which was stirred with ethyl acetate (30 mL) to give solid material which was filtered and dried under vacuum. The solid material obtained was further purified by Prep HPLC purification to afford the title compound as white solid (0.056 g, 54.24%).

Compound 6—(E)-2-(2,3,4-trichlorobenzylidene)hydrazine-1-carboximidamide

Synthetic Scheme:

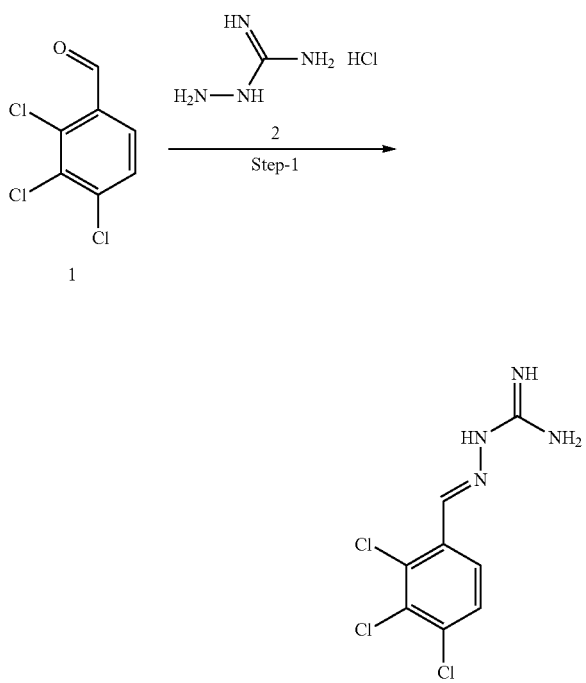

Experimental Details

Calculation:

| Chemicals | Quantity | Mol. Wt | Mole | Mole ratio |
|---|---|---|---|---|
| Intermediate 1 | 0.1 g | 209.5 | 0.00047 | 1 |
| Intermediate 2 | 0.052 g | 110.5 | 0.00047 | 1 |
| NaOAc | 0.039 g | 82.03 | 0.00047 | 1 |
| Ethanol | 1 mL | — | — | 10 V |

Procedure

To the solution of Intermediate 1 (0.1 g, 0.00047 mol) and Intermediate 2 (0.052 g, 0.00047 mol) in ethanol (1 mL) was added NaOAc (0.039 g, 0.00047 mol) and heated to 80° C. for 4 h. The progress of reaction was monitored by TLC using 20% MeOH in DCM as mobile phase. The cold solution of $NaHCO_3$ (5 mL) was added in to the reaction mixture and stirred for 10 min. The precipitate were filtered, washed thoroughly with water (2×10 mL) and dried under reduced pressure to obtain pure product which was subjected for analysis (0.097 g, 76.98% yield).

Compound 7—(E)-2-(2,4-dichloro-5-fluorobenzylidene)hydrazine-1-carboximidamide

Synthetic Scheme:

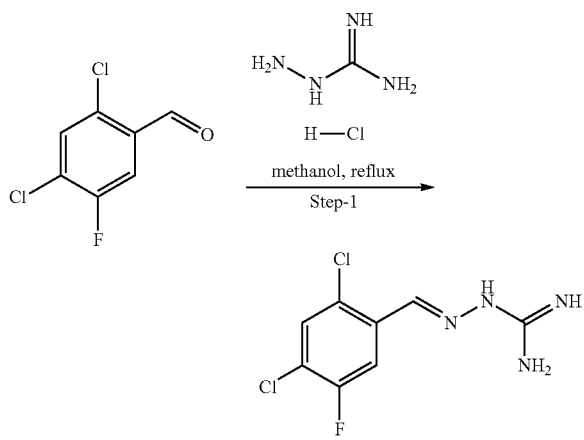

Experimental Details

To a solution of 2,4-Dichloro-5-fluorobenzaldehyde (0.1 g, 0.52 mmol) in methanol (2 mL) was added amino guanidine hydrochloride (0.046 g, 0.42 mmol). The reaction mixture was stirred for 2 h at 65-70° C. Reaction mixture was cooled and methanol was removed under reduced pressure to provide crude product which was crystallized with ethyl acetate (30 mL) to give solid material. The obtained solid material was further purified by Prep HPLC purification to afford the title compound as off white solid (0.1 g, 96.86%).

Compound 8—(E)-2-(4-chloro-3-fluorobenzylidene)hydrazine-1-carboximidamide

Synthetic Scheme:

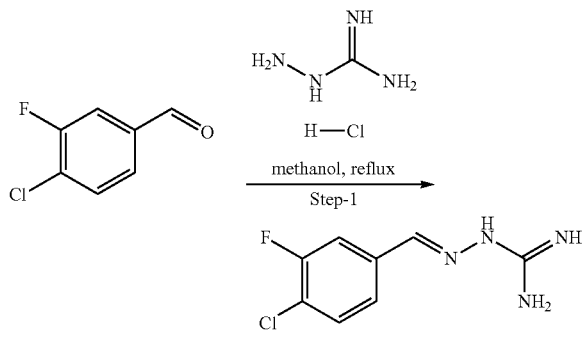

Experimental Details

To a solution of 4-chloro-3-fluorobenzaldehyde (0.1 g, 0.63 mmol) in methanol (2 mL) was added amino guanidine hydrochloride (0.056 g, 0.51 mmol). The reaction was stirred for 2 h at 65-70° C. The reaction showed 90% conversion on TLC. Reaction mixture was concentrated under reduced pressure to provide crude product which was stirred with ethyl acetate (30 mL) to give solid material which was filtered and dried under vacuum. Further purification of the solid material obtained was carried out with column chromatography using silica gel (100-200) and 8% MeOH/DCM as eluent to afford the title compound as off white solid (0.059 g, 54.48%).

Compound 9—(E)-2-(2-bromo-3-chlorobenzylidene)hydrazine-1-carboximidamide

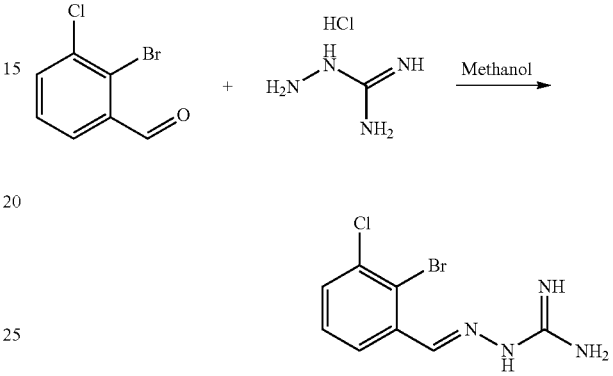

Experimental Details

To a solution of 2-bromo-3-chlorobenzaldehyde (0.63 mmol) in methanol (2 mL) was added amino guanidine hydrochloride (0.79 mmol). The reaction was stirred for 2 h at 65-70° C. The reaction showed 90% conversion on TLC. Reaction mixture was concentrated under reduced pressure to provide crude product which was stirred with ethyl acetate (30 mL) to give solid material which was filtered and dried under vacuum. Purification of the solid material was carried out with column chromatography using silica gel (100-200) and 8.5% MeOH/DCM as eluent to afford the title compound.

Compound 10—(E)-2-(2,3,5-trichlorobenzylidene)hydrazine-1-carboximidamide

Synthetic Scheme:

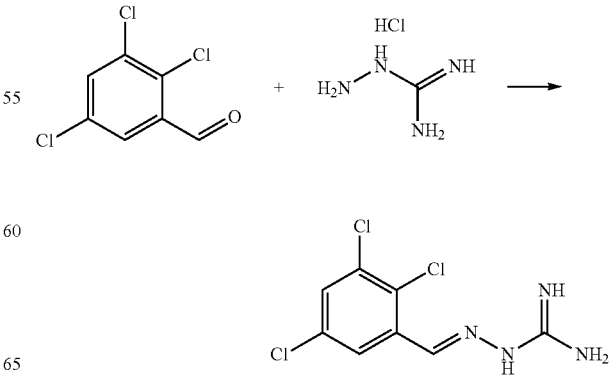

Experimental Details

Calculation:

| | Chemicals | Quantity | M.W. | Mole | Mole ratio |
|---|---|---|---|---|---|
| 1 | 2,3,5-trichlorobenzaldehyde | 0.040 g | 207.92 | 0.00019 | 1.00 |
| 2 | Aminoguanidine hydrochloride | 0.021 g | 110.55 | 0.00019 | 1.00 |
| 3 | Sodium acetate | 0.015 g | 82.03 | 0.00019 | 1.00 |
| 4 | Ethanol | 1 ml | | | |

Procedure:

To a solution of 2,3,5-trichlorobenzaldehyde (0.040 g, 0.00019 mol) in ethanol (1 ml) was sequentially added amino guanidine hydrochloride (0.021 g, 0.00019 mol) and sodium acetate (0.015 g, 0.00019 mol) at 25° C. The resulting reaction mixture was heated at 80° C. for next 6 hours. Reaction completion was monitored on TLC using dichloromethane/methanol (8/2) as mobile phase. After completion of reaction, the reaction mixture was allowed to cool down to 25° C. and dumped in a saturated solution of $NaHCO_3$ (10 ml). The resulting precipitates were filtered off under vacuum and washed with water (5 ml). The resulting solid material was triturated with diethyl ether (2×2 ml) and dried under vacuum to provide the title compound (0.036 g, 70.88% yield).

Compound 11—(E)-2-(3,4-dichlorobenzylidene)hydrazine-1-carboximidamide

Synthetic Scheme:

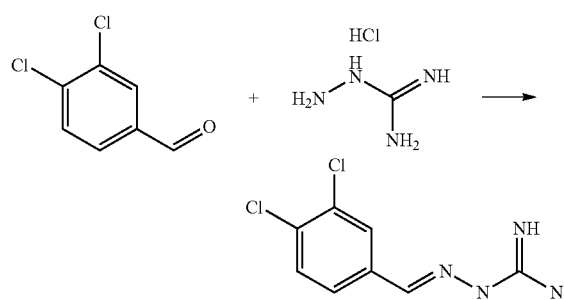

Experimental Details

Calculation:

| | Chemicals | Quantity | M.W. | Mole | Mole ratio |
|---|---|---|---|---|---|
| 1 | 3,4-dichlorobenzaldehyde | 0.030 g | 173.96 | 0.00017 | 1.00 |
| 2 | Aminoguanidine hydrochloride | 0.019 g | 110.55 | 0.00017 | 1.00 |
| 3 | Sodium acetate | 0.014 g | 82.03 | 0.00017 | 1.00 |
| 4 | Ethanol | 1 ml | | | |

Procedure:

To a solution of 3,4-dichlorobenzaldehyde (0.030 g, 0.00017 mol) in ethanol (1 ml) was sequentially added amino guanidine hydrochloride (0.019 g, 0.00017 mol) and sodium acetate (0.014 g, 0.00017 mol) at 25° C. The resulting reaction mixture was heated at 80° C. for next 6 hours. Reaction completion was monitored on TLC using dichloromethane/methanol (8/2) as mobile phase. After completion of reaction, the reaction mixture was allowed to cool down to 25° C. and dumped in a saturated solution of $NaHCO_3$ (10 ml). The resulting precipitates were filtered off under vacuum and washed with water (5 ml). The resulting solid material was triturated with diethyl ether (2×2 ml) and dried under vacuum to provide the titled compound (0.035 g, 88.2% yield).

Compound 12—(E)-2-(2,4-dichlorobenzylidene)hydrazine-1-carboximidamide

The following synthesis of compound 12 is described in Nguyen et al., 2014, 5 (10), 1075-1082

Synthetic Scheme:

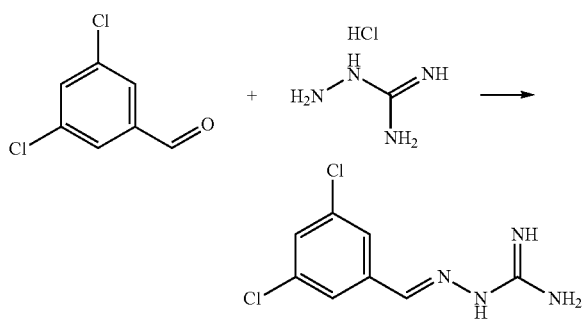

Protocol:

3,5-dichlorobenzaldehyde (1.0 mmol, 175 mg) and salt aminoguanidine hydrochloride (1.0 mmol, 110 mg) in EtOH (2 ml) were shaken at reflux for 12 hours. After cooling at room temperature, the final compound was recovered as a precipitate after filtration. The title compound was recovered as a white powder (210 mg, 79%).

Compound 13—(E)-2-(2,4-dichloro-3-fluorobenzylidene)hydrazine-1-carboximidamide

Synthetic Scheme:

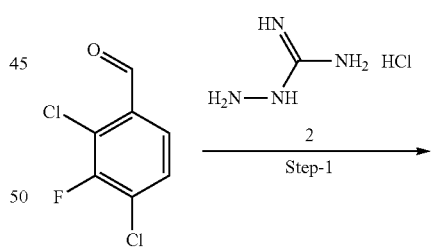

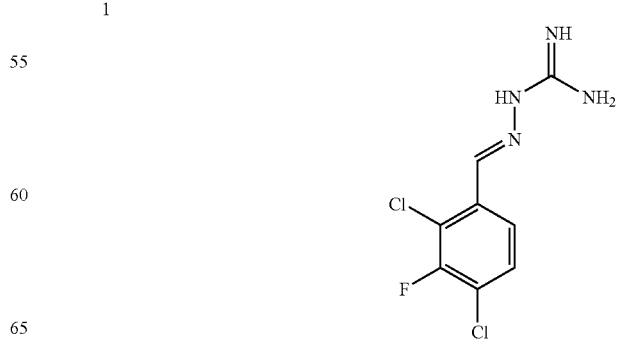

Experimental Details

Calculation:

| Chemicals | Quantity | Mol. Wt | Mole | Mole ratio |
|---|---|---|---|---|
| Intermediate 1 | 0.1 g | 193.03 | 0.00051 | 1 |
| Intermediate 2 | 0.057 g | 110.5 | 0.00051 | 1 |
| NaOAc | 0.042 g | 82.03 | 0.00051 | 1 |
| Ethanol | 1 mL | — | — | 10 V |

Procedure:

To the solution of Intermediate 1 (0.1 g, 0.00051 mol) and Intermediate 2 (0.057 g, 0.00051 mol) in ethanol (1 mL) was added NaOAc (0.042 g, 0.00051 mol) and heated to 80° C. for 4 h. The progress of reaction was monitored by TLC using 20% MeOH in DCM as mobile phase. The cold solution of NaHCO$_3$ (5 mL) was added in to the reaction mixture and stirred for 10 min. The precipitate were filtered, washed thoroughly with water (2×10 mL) and dried under reduced pressure to obtain pure product which was subjected for analysis (0.05 g; 38.75% yield).

Compound 14—(E)-2-(2,3-dichloro-4-fluorobenzylidene)hydrazine-1-carboximidamide Synthetic Scheme:

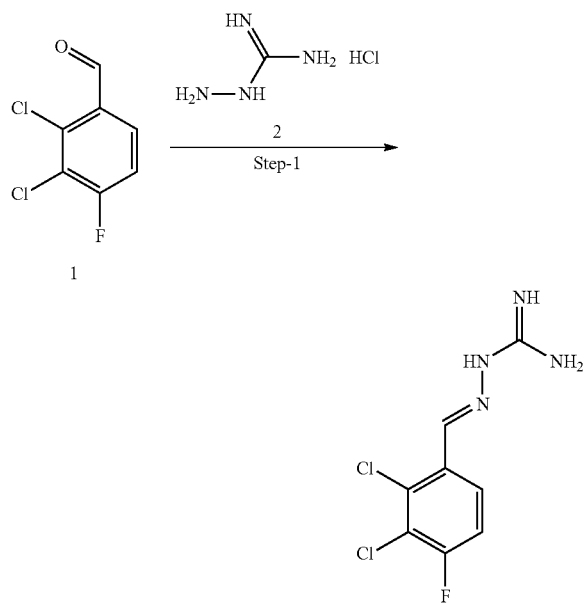

Experimental Details

Calculation:

| Chemicals | Quantity | Mol. Wt | Mole | Mole ratio |
|---|---|---|---|---|
| Intermediate 1 | 0.05 g | 193 | 0.00025 | 1 |
| Intermediate 2 | 0.028 g | 110.5 | 0.00025 | 1 |
| NaOAc | 0.021 g | 82.03 | 0.00025 | 1 |
| Ethanol | 0.5 mL | — | — | 10 V |

Procedure:

To the solution of Intermediate 1 (0.05 g, 0.00025 mol) and Intermediate 2 (0.028 g, 0.00025 mol) in ethanol (0.5 mL) was added NaOAc (0.021 g, 0.00025 mol) and heated to 80° C. for 4 h. The progress of reaction was monitored by TLC using 20% MeOH in DCM as mobile phase. The cold solution of NaHCO$_3$ (2.5 mL) was added in to the reaction mixture and stirred for 10 min. The precipitate were filtered, washed thoroughly with water (2×5 mL) and dried under reduced pressure to obtain pure product which was subjected for analysis (0.043 g, 67.18% yield).

Compound 15—(E)-2-(3-chloro-4-fluorobenzylidene)hydrazine-1-carboximidamide

Synthetic Scheme:

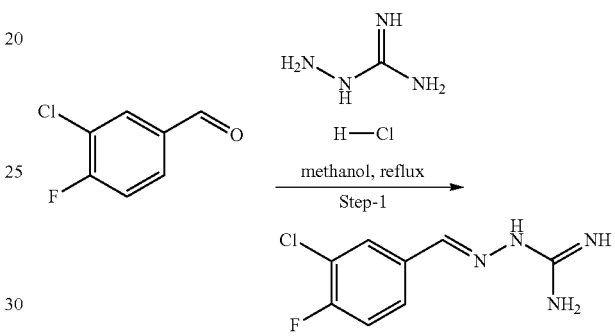

Experimental Details

To a solution of 3-chloro-4-fluorobenzaldehyde (0.1 g, 0.63 mmol) in methanol (2 mL) was added amino guanidine hydrochloride (0.087 g, 0.79 mmol). The reaction was stirred for 2 h at 65-70° C. The reaction showed 80% conversion on TLC. Reaction mixture was concentrated under reduced pressure to provide crude product which was stirred with ethyl acetate (30 mL) to give solid material which was filtered and dried under vacuum. Further purification of the solid material obtained was carried out with column chromatography using silica gel (100-200) and 8% MeOH/DCM as eluent to afford the title compound as off white solid (0.053 g, 39.15%).

Compound 16—(E)-2-(2,3-dichlorobenzylidene)hydrazine-1-carboximidamide

Synthetic Scheme:
Procedure:

To a solution of 2,3-dichlorobenzaldehyde (1 e.) in ethanol (300 ml) was sequentially added amino guanidine hydrochloride (1 eq.) and sodium acetate (1 eq.) at 25° C. The resulting reaction mixture was heated at 80° C. for next ~6 hours. Reaction completion was monitored on TLC using dichloromethane/methanol (8/2) as mobile phase. After completion of reaction, the reaction mixture was allowed to cool down to 25° C. and dumped in a saturated solution of NaHCO$_3$ (700 ml). The resulting precipitates were filtered off under vacuum and washed with water (100 ml). The resulting solid material was triturated with diethyl ether (2×25 ml) and dried under vacuum to provide the title compound (85% yield), considering mono acetate salt) LC-MS: m/z=231.23 (M+H). $^1$H-NMR (DMSO-d$_6$): δ

(ppm) 11.85 (brs, 1H); 8.35 (s, 1H); 8.19-8.21 (dd, 1H); 7.56-7.59 (dd, 1H); 7.32-7.36 (t, 1H); 7.04 (brs, 4H); 1.84 (s, 3H); MS (ESI+): m/z=231.23 [M+H]

Compound 17—(E)-2-(2-fluorobenzylidene)hydrazine-1-carboximidamide

Synthetic Scheme:

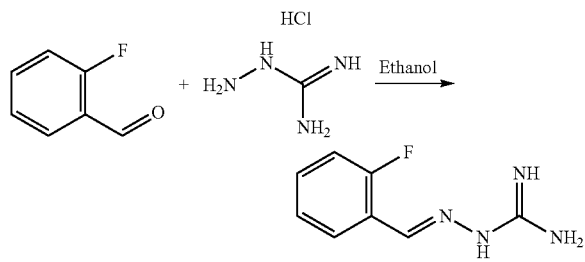

Procedure:

To a solution of 2-fluorobenzaldehyde (1 eq.) in ethanol (300 ml) was sequentially added aminoguanidine hydrochloride (1 eq.) and sodium acetate (1 eq.) at 25° C. The resulting reaction mixture was heated at 80° C. for next ~6 hours. Reaction completion was monitored on TLC using dichloromethane/methanol (8/2) as mobile phase. After completion of reaction, the reaction mixture was allowed to cool down to 25° C. and dumped in the saturated solution of $NaHCO_3$ (700 ml). The resulting precipitate were filtered off under vacuum and washed with water (100 ml). The resulting solid material was titurated with diethylether (2×25 ml) and dried under vacuum to provide the title compound.

Compound 18—(E)-2-(4,5-dichloro-2-fluorobenzylidene)hydrazine-1-carboximidamide Synthetic Scheme:

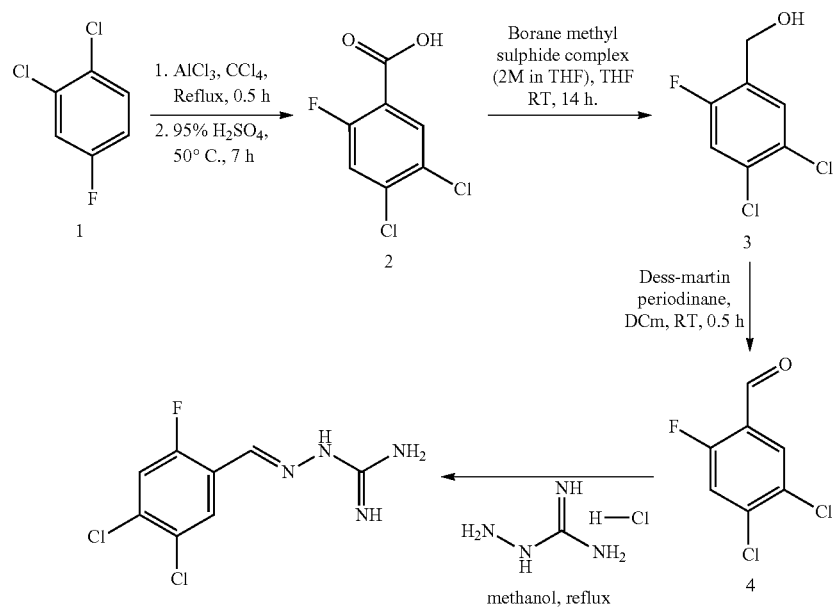

Experimental Details

Step-1:

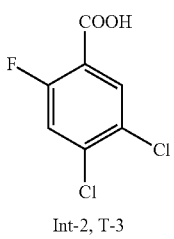 [SMILES: O=C(O)c1cc(Cl)c(Cl)cc1F]

Int-2, T-3

Aluminum chloride (3.22 g, 24.24 mmol) was suspended in carbon tetrachloride (20 mL) at 0° C. and the suspension was gradually heated. 1,2-dichloro-4-fluorobenzene (2.0 g, 12.12 mmol) was added drop wise over 2 h under reflux and the mixture was heated under reflux further for 0.5 h. After solution was allowed to cool to room temperature, mixture was carefully poured into iced water. The organic layer was washed with water, 5% $NaHCO_3$ solution and then by water. Organic layer was dried over $MgSO_4$ and concentrated under reduced pressure to give crude intermediate. The crude intermediate was suspended in 95% sulfuric acid and the suspension was stirred at 50° C. for 7 h. The solution was poured into iced water and the resulting crude crystals were collected by filtration. The crystals were dissolved in 1N NaOH solution and the solution was washed with ethyl acetate. The aqueous layer was neutralized with 6N HCl solution and was extracted with ethyl acetate. The extracts was washed with brine, dried over anhydrous $MgSO_4$, and concentrated under reduced pressure. The crude crystals thus obtained were collected by filtration (0.35 g).

Step-2:

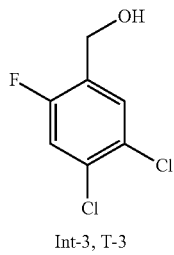

Int-3, T-3

To a solution of Int-2 of T-3 (0.35 g, 1.67 mmol) in THF (10 mL) was treated with borane methylsulfide complex (2.51 mmol) at 0-5° C. The mixture was allowed to come to rt, stirred for 14 h at rt and quenched with sat. NaHCO$_3$ solution and methanol (2 mL). The mixture was extracted with ethyl acetate. Organic layer was washed with 10% HCl and saturated NaHCO$_3$ solutions, dried over MgSO$_4$ and concentrated to give 0.275 g of the product as a white solid.

Step-3:

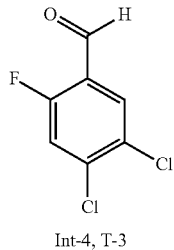

Int-4, T-3

To an ice-cold solution of Int-3 of T-3 (0.275 g, 1.41 mmol) in DCM was added Dess Martin periodinane (0.896 g, 2.11 mmol) and then stirred for 30 min. Reaction mixture was quenched with sat. NaHCO$_3$ solution and stirring was quenched for 30 min. Organic layer was separated, washed with water, dried over MgSO$_4$ and concentrated to provide Int-4 of T-3 (0.17 g)

Step-4:

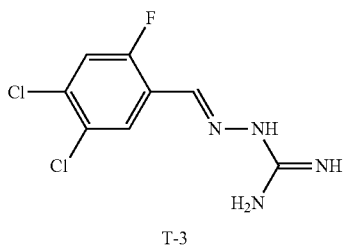

T-3

To a solution of Compound-3 (0.15 g, 0.77 mmol) in methanol (3 mL) was added amino guanidine hydrochloride (0.069 g, 0.62 mmol). The reaction was stirred for 2 h at 65-70° C. The reaction showed 100% conversion on TLC.
Reaction mixture was concentrated under reduced pressure to provide crude product which was stirred with ethyl acetate (30 mL) to give solid material which was filtered and dried under vacuum. The crude solid material was further purified by Prep HPLC purification to afford the title compound as white solid (0.085 g, 82.33%).

Compound 20—(E)-2-(2-chloro-5-fluorobenzylidene)hydrazine-1-carboximidamide

Synthetic Scheme:

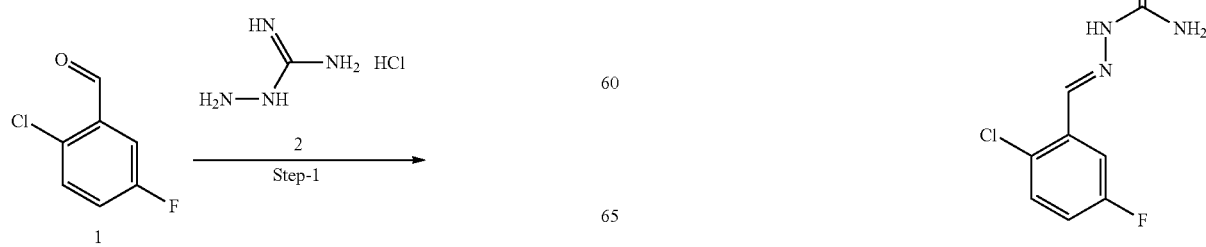

Experimental Details

Calculation:

| Chemicals | Quantity | Mol. Wt | Mole | Mole ratio |
|---|---|---|---|---|
| Intermediate 1 | 0.1 g | 158.6 | 0.00063 | 1 |
| Intermediate 2 | 0.069 g | 110.5 | 0.00063 | 1 |
| NaOAc | 0.051 g | 82.03 | 0.00063 | 1 |
| Ethanol | 1 mL | — | — | 10 V |

Procedure:

To the solution of Intermediate 1 (0.1 g, 0.00063 mol) and Intermediate 2 (0.069 g, 0.00063 mol) in ethanol (1 mL) was added NaOAc (0.051 g, 0.00063 mol) and heated to 80° C. for 4 h. The progress of reaction was monitored by TLC using 20% MeOH in DCM as mobile phase. The cold solution of $NaHCO_3$ (5 mL) was added in to the reaction mixture and stirred for 10 min. The precipitate were filtered, washed thoroughly with water (2×10 mL) and dried under reduced pressure to obtain pure product (0.086 g, 63.07% yield).

Compound 22—(E)-2-((2,6-dichloropyridin-3-yl)methylene)hydrazine-1-carboximidamide Reaction Scheme:

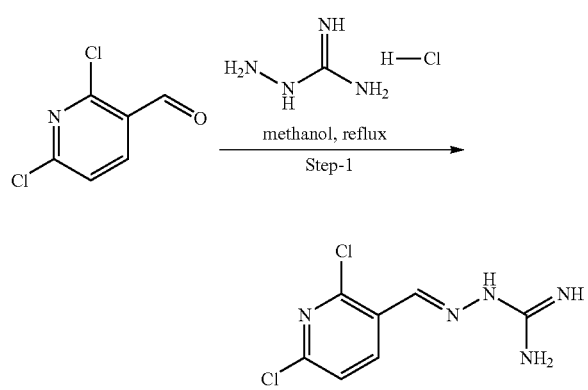

Experimental Details

To a solution of 2,6-Dichloronicotinaldehyde (0.1 g, 0.57 mmol) in methanol (2 mL) was added amino guanidine hydrochloride (0.079 g, 0.71 mmol). The reaction mixture was stirred for 2 h at 65-70° C. The reaction showed 80% conversion on TLC. Reaction mixture was concentrated under reduced pressure to provide crude residue which was stirred with ethyl acetate (30 mL) to give solid material which was filtered and dried under vacuum. Further purification of the solid material was carried out with column chromatography using silica gel (100-200) and 5% MeOH/DCM as eluent to afford the desired compound as yellow solid (0.040 g, 30.99%).

Compound 23—(E)-2-(3-fluorobenzylidene)hydrazine-1-carboximidamide

Synthetic Scheme:

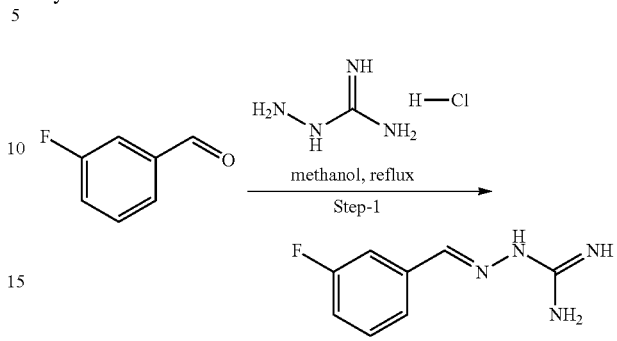

Experimental Details

To a solution of 3-fluorobenzaldehyde (0.1 g, 0.81 mmol) in methanol (2 mL) was added amino guanidine hydrochloride (0.047 g, 0.43 mmol). The reaction mixture was stirred for 2 h at 65-70° C. The reaction showed 90% conversion on TLC. Reaction mixture was concentrated under reduced pressure to provide crude residue which was stirred with ethyl acetate (30 mL) to give solid material which was filtered and dried under vacuum. Further purification of the solid material was carried with column chromatography using silica gel (100-200) and 6.5% MeOH/DCM as eluent to afford the desired compound as off white solid (0.069 g, 66.83%).

Compound 24—(E)-2-(3-chlorobenzylidene)hydrazine-1-carboximidamide

Synthetic Scheme:

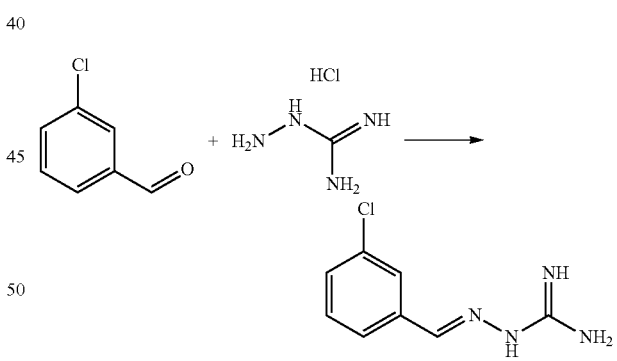

Experimental Details

Calculation:

| | Chemicals | Quantity | M.W. | Mole | Mole ratio |
|---|---|---|---|---|---|
| 1 | 3-chlorobenzaldehyde | 0.050 g | 140.57 | 0.00035 | 1.00 |
| 2 | Aminoguanidine hydrochloride | 0.039 g | 110.55 | 0.00035 | 1.00 |
| 3 | Sodium acetate | 0.028 g | 82.03 | 0.00035 | 1.00 |
| 4 | Ethanol | 1 ml | | | |

Procedure:

To a solution of 3-chlorobenzaldehyde (0.050 g, 0.00035 mol) in ethanol (1 ml) was sequentially added aminoguanidine hydrochloride (0.039 g, 0.00035 mol) and sodium acetate (0.028 g, 0.00035 mol) at 25° C. The resulting reaction mixture was heated at 80° C. for next 6 hours. Reaction completion was monitored on TLC using dichloromethane/methanol (8/2) as mobile phase. After completion of reaction, the reaction mixture was allowed to cool down to 25° C. and dumped in a saturated solution of NaHCO₃ (10 ml). The resulting precipitates were filtered off under vacuum and washed with water (5 ml). The resulting solid material was triturated with diethyl ether (2×2 ml) and dried under vacuum to provide the titled compound (0.035 g, 50.19% yield).

Compound 25—(E)-2-(3-chloro-2-fluorobenzylidene)hydrazine-1-carboximidamide

Synthetic Scheme:

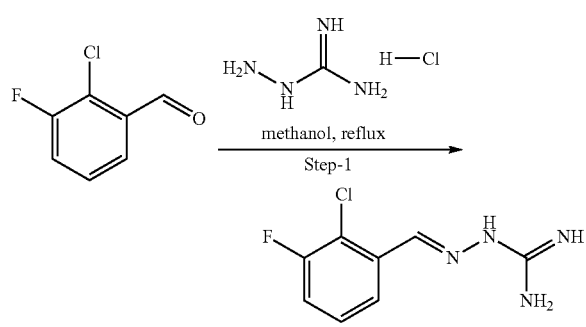

Experimental Details:

To a solution of 2-Chloro-3-fluorobenzaldehyde (0.1 g, 0.63 mmol) in methanol (2 mL) was added amino guanidine hydrochloride (0.087 g, 0.79 mmol). The reaction was stirred for 2 h at 65-70° C. The reaction showed 90% conversion on TLC. Reaction mixture was concentrated under reduced pressure to provide crude product which was stirred with ethyl acetate (30 mL) to give solid material which was filtered and dried under vacuum. Purification of the solid material was carried out with column chromatography using silica gel (100-200) and 8.5% MeOH/DCM as eluent to afford the titled compound as off white solid (0.088 g, 68.19%).

Compound 26—(E)-2-(2,5-dichlorobenzylidene)hydrazine-1-carboximidamide

Synthetic Scheme:

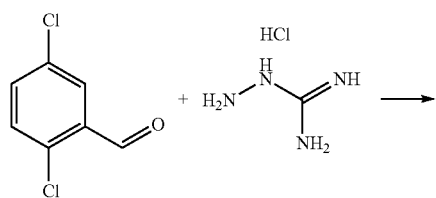

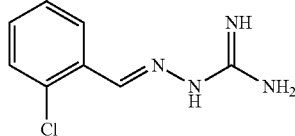

Experimental Details

Calculation:

| | Chemicals | Quantity | M.W. | Mole | Mole ratio |
|---|---|---|---|---|---|
| 1 | 2,5-dichlorobenzaldehyde | 0.045 g | 173.96 | 0.00025 | 1.00 |
| 2 | Aminoguanidine hydrochloride | 0.028 g | 110.55 | 0.00025 | 1.00 |
| 3 | Sodium acetate | 0.020 g | 82.03 | 0.00025 | 1.00 |
| 4 | Ethanol | 1 ml | | | |

Procedure:

To a solution of 2,5-dichlorobenzaldehyde (0.045 g, 0.00025 mol) in ethanol (1 ml) was sequentially added amino guanidine hydrochloride (0.028 g, 0.00025 mol) and sodium acetate (0.020 g, 0.00025 mol) at 25° C. The resulting reaction mixture was heated at 80° C. for next 6 hours. Reaction completion was monitored on TLC using dichloromethane/methanol (8/2) as mobile phase. After completion of reaction, the reaction mixture was allowed to cool down to 25° C. and dumped in a saturated solution of NaHCO₃ (10 ml). The resulting precipitates were filtered off under vacuum and washed with water (5 ml). The resulting solid material was triturated with diethyl ether (2×2 ml) and dried under vacuum to provide the title compound (0.039 g, 65.55% yield).

Compound 27—(E)-2-(2-chloro-3,4-difluorobenzylidene)hydrazine-1-carboximidamide

Synthetic Scheme:

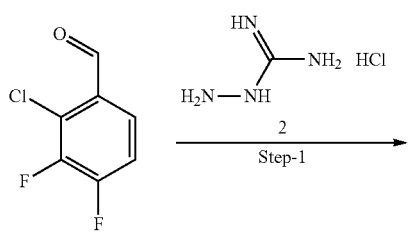

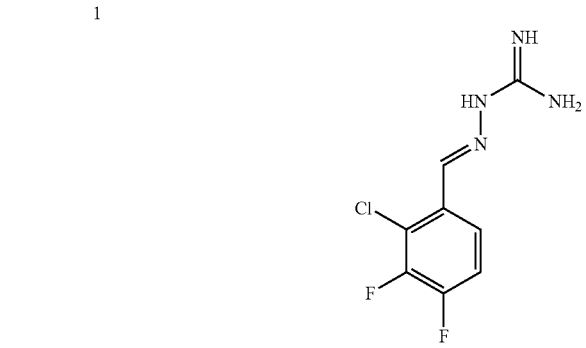

Experimental Details

Calculation:

| Chemicals | Quantity | Mol. Wt | Mole | Mole ratio |
| --- | --- | --- | --- | --- |
| Intermediate 1 | 0.04 g | 176.55 | 0.00022 | 1 |
| Intermediate 2 | 0.025 g | 110.5 | 0.00022 | 1 |
| NaOAc | 0.018 g | 82.03 | 0.00022 | 1 |
| Ethanol | 0.4 mL | — | — | 10 V |

Procedure:

To the solution of Intermediate 1 (0.04 g, 0.00022 mol) and Intermediate 2 (0.025 g, 0.00022 mol) in ethanol (0.4 mL) was added NaOAc (0.018 g, 0.00022 mol) and heated to 80° C. for 4 h. The progress of reaction was monitored by TLC using 20% MeOH in DCM as mobile phase. The cold solution of NaHCO$_3$ (2.5 mL) was added in to the reaction mixture and stirred for 10 min. The precipitate were filtered, washed thoroughly with water (2×5 mL) and dried under reduced pressure to obtain pure product which was subjected for analysis (0.063 g, 95.43% yield).

Compound 29—(E)-2-(2-chloro-3,5-difluorobenzylidene)hydrazine-1-carboximidamide

Synthetic Scheme:

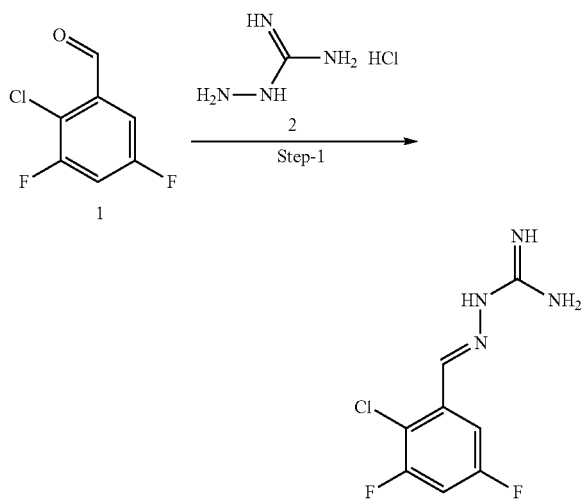

Experimental Details

Calculation:

| Chemicals | Quantity | Mol. Wt | Mole | Mole ratio |
| --- | --- | --- | --- | --- |
| Intermediate 1 | 0.06 g | 176.55 | 0.00033 | 1 |
| Intermediate 2 | 0.037 g | 110.5 | 0.00033 | 1 |
| NaOAc | 0.027 g | 82.03 | 0.00033 | 1 |
| Ethanol | 0.6 mL | — | — | 10 V |

Procedure: To the solution of Intermediate 1 (0.06 g, 0.00033 mol) and Intermediate 2 (0.037 g, 0.00033 mol) in ethanol (0.6 mL) was added NaOAc (0.027 g, 0.00033 mol) and heated to 80° C. for 4 h. The progress of reaction was monitored by TLC using 20% MeOH in DCM as mobile phase. The cold solution of NaHCO$_3$ (2.7 mL) was added in to the reaction mixture and stirred for 10 min. The precipitate were filtered, washed thoroughly with water (2×2.7 mL) and dried under reduced pressure to obtain pure product which was subjected for analysis (0.04 g, 50.63% yield).

Compound 30—(E)-2-(3-chloro-2-fluorobenzylidene)hydrazine-1-carboximidamide

Synthetic Scheme:

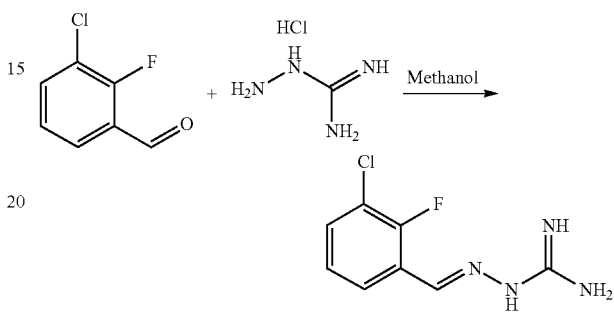

Experimental Details

To a solution of 3-Chloro-2-fluorobenzaldehyde (0.1 g, 0.63 mmol) in methanol (2 mL) was added amino guanidine hydrochloride (0.087 g, 0.79 mmol). The reaction was stirred for 2 h at 65-70° C. The reaction showed 90% conversion on TLC. Reaction mixture was concentrated under reduced pressure to provide crude product which was stirred with ethyl acetate (30 mL) to give solid material which was filtered and dried under vacuum. Purification of the solid material was carried out with column chromatography using silica gel (100-200) and 8.5% MeOH/DCM as eluent to afford title compound.

Compound 31—(E)-2-(2,3,6-trichlorobenzylidene)hydrazine-1-carboximidamide

Synthetic Scheme:

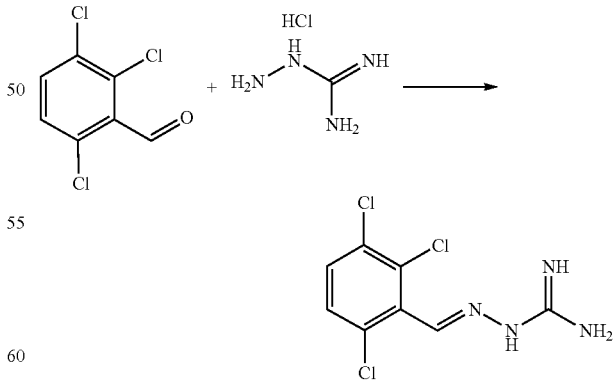

Experimental Details

To a solution of 2,3,6-trichlorobenzaldehyde (0.040 g, 0.00019 mol) in ethanol (1 ml) was sequentially added amino guanidine hydrochloride (0.021 g, 0.00019 mol) and sodium acetate (0.015 g, 0.00019 mol) at 25° C. The resulting reaction mixture was heated at 80° C. for next 6 hours. Reaction completion was monitored on TLC using dichloromethane/methanol (8/2) as mobile phase. After completion of reaction, the reaction mixture was allowed to cool down to 25° C. and dumped in a saturated solution of NaHCO₃ (10 ml). The resulting precipitates were filtered off under vacuum and washed with water (5 ml). The resulting solid material was triturated with diethyl ether (2×2 ml) and dried under vacuum to provide the title compound.

Compound 32—(E)-2-(2-chloro-4,5-difluorobenzylidene)hydrazine-1-carboximidamide

Synthetic Scheme:

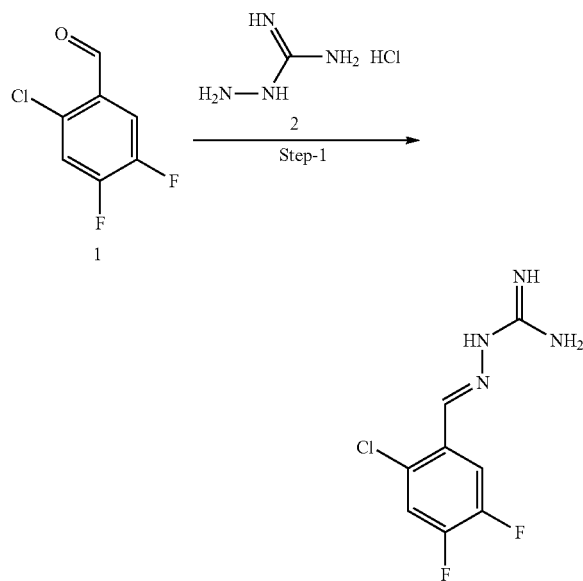

Experimental Details

Calculation:

| Chemicals | Quantity | Mol. Wt | Mole | Mole ratio |
| --- | --- | --- | --- | --- |
| Intermediate 1 | 0.1 g | 176.55 | 0.00056 | 1 |
| Intermediate 2 | 0.062 g | 110.5 | 0.00056 | 1 |
| NaOAc | 0.046 g | 82.03 | 0.00056 | 1 |
| Ethanol | 1 mL | — | — | 10 V |

Procedure:

To the solution of Intermediate 1 (0.1 g, 0.00056 mol) and Intermediate 2 (0.062 g, 0.00056 mol) in ethanol (1 mL) was added NaOAc (0.046 g, 0.00056 mol) and heated to 80° C. for 4 h. The progress of reaction was monitored by TLC using 20% MeOH in DCM as mobile phase. The cold solution of NaHCO₃ (5 mL) was added in to the reaction mixture and stirred for 10 min. The precipitate were filtered, washed thoroughly with water (2×10 mL) and dried under reduced pressure to obtain pure product which was subjected for analysis (0.117 g, 89.31% yield).

Compound 34—(E)-2-(3,5-dichlorobenzylidene)hydrazine-1-carboximidamide

Synthetic Scheme:

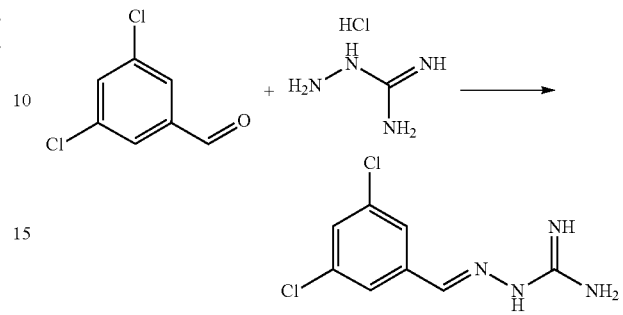

Experimental Details

Calculation:

| | Chemicals | Quantity | M.W. | Mole | Mole ratio |
| --- | --- | --- | --- | --- | --- |
| 1 | 3,5-dichlorobenzaldehyde | 0.030 g | 173.96 | 0.00017 | 1.00 |
| 2 | Aminoguanidine hydrochloride | 0.019 g | 110.55 | 0.00017 | 1.00 |
| 3 | Sodium acetate | 0.013 g | 82.03 | 0.00017 | 1.00 |
| 4 | Ethanol | 1 ml | | | |

Procedure:

To a solution of 3,5-dichlorobenzaldehyde (0.030 g, 0.00017 mol) in ethanol (1 ml) was sequentially added amino guanidine hydrochloride (0.019 g, 0.00017 mol) and sodium acetate (0.013 g, 0.00017 mol) at 25° C. The resulting reaction mixture was heated at 80° C. for next 6 hours. Reaction completion was monitored on TLC using dichloromethane/methanol (8/2) as mobile phase. After completion of reaction, the reaction mixture was allowed to cool down to 25° C. and dumped in a saturated solution of NaHCO₃ (10 ml). The resulting precipitates were filtered off under vacuum and washed with water (5 ml). The resulting solid material was triturated with diethyl ether (2×2 ml) and dried under vacuum to provide the title compound (0.038 g, 95.8% yield).

General procedure A:

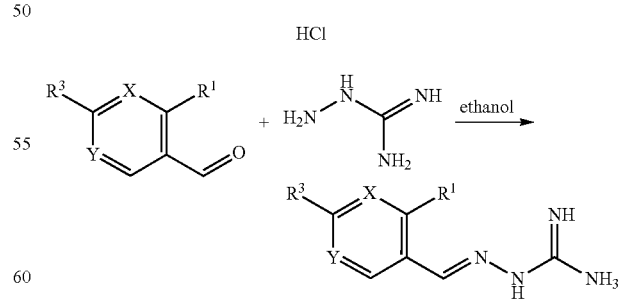

To a solution of benzaldehyde (1 eq.) in ethanol (300 ml) was sequentially added aminoguanidine hydrochloride (1 eq.) and sodium acetate (1 eq.) at 25° C. The resulting reaction mixture was heated at 80° C. for next ~6 hours. Reaction completion was monitored on TLC using dichloromethane/methanol (8/2) as mobile phase. After completion of reaction, the reaction mixture was allowed to cool down to 25° C. and dumped in the saturated solution of NaHCO$_3$ (700 ml). The resulting precipitate were filtered off under vacuum and washed with water (100 ml). The resulting solid material was titurated with diethylether (2×25 ml) and dried under vacuum to provide the desired substituted aminoguanidine derivative.

The following compounds were prepared according to general procedure A:

Example 1 (Compound 16(E)): (E)-2-(2,3-dichlorobenzylidene)hydrazine-1-carboximidamide Prepared following general procedure A from 2,3-dichlorobenzaldehyde in 85% yield (considering mono acetate salt) LC-MS: m/z=231.23 (M+H). $^1$H-NMR (DMSO-d$_6$): δ (ppm) 11.85 (brs, 1H); 8.35 (s, 1H); 8.19-8.21 (dd, 1H); 7.56-7.59 (dd, 1H); 7.32-7.36 (t, 1H); 7.04 (brs, 4H); 1.84 (s, 3H); MS (ESI+): m/z=231.23 [M+H]$^+$ Example 2: (E)-2-(2-chloro-4-fluorobenzylidene)hydrazine-1-carboximidamide Prepared following general procedure A from 2-chloro-4-fluorobenzaldehyde in 67% yield. $^1$H-NMR (DMSO-d$_6$): δ (ppm) 5.80 (brs, 2H); 5.84 (brs, 2H); 7.19-7.34 (m, 4H); 8.16 (s, 1H); MS (ESI+): m/z=215.1 [M+H]$^+$ The protocols and assays of Example A were carried out in relation to PPP1R15B inhibition. However, it will be appreciated that the methods described herein are equally applicable to identifying/analysing PPP1R15A and PPP1R15B inhibitors.

Example A

Protein Expression, Purification and Analysis by Surface Plasmon Resonance
Protein Expression and Purification
PPP1R15A$^{325-636}$ and PPP1R15B$^{340-698}$ were expressed and purified as follows: the cDNAs encoding amino acids 325-636 of PPP1R15A and 340-698 of PPP1R15B were His-tagged and cloned into pMAL-c5x. Recombinant PPP1R15A/B were expressed in BL21-Gold cells and purified by affinity chromatography on a HisTrap HP column (GE Healthcare), followed by a MBPTrap HP column (GE Healthcare). The proteins were analyzed on BOLT SDS-PAGE 4-12% Bis-Tris gels (Life Technologies) stained with SimplyBlue SafeStain (Life Technologies). cDNA encoding for human PP1γ was cloned into the baculovirus transfer vector pDW464 to add a biotin acceptor peptide (BAP). The vector also encodes for the *E. coli* biotin holoenzyme synthetase (BirA), so that BAP-tagged proteins can be biotinylated in vivo in *Spodoptere frugiperda* (Sf9) insect cells (Duffy et al., Anal. Biochem., 262, 122-128, 1998). The Bac-to-Bac baculovirus expression system (Life Technologies) was used to generate the recombinant bacmid DNA and Sf9 insect cells were used to amplify the viral stocks Cultures were harvested by centrifuging at 1,200 g for 15 minutes, cell pellets were resuspended in lysis buffer (50 mM Tris pH 7.4, 150 mM NaCl, 0.2% Triton, 5% Glycerol, 1 PiC tablet (Roche) per 50 ml and 0.2 mM PMSF) and followed by gentle sonication. The protein was first purified on a 5 ml HiTrap Q HP column (GE Healthcare) followed by a HiLoad 16/600 Superdex 200 column (GE Healthcare). The positive fractions confirmed by SDS-PAGE and western blot were pooled, concentrate to ~1 μM and stored at −80° C.

Capture of Biotin-PP1 on the SA Sensor Chip
A Biacore T200 (GE Healthcare) system was used for all experiments and biotinylated PP1 was captured using a Sensor Chip SA (GE Healthcare, catalog no BR-1005-31). The streptavidin coated surface was activated by 1 min injection with a solution of 50 mM NaOH and 1 M NaCl. Biotin-PP1 was diluted in the running buffer (50 mM Tris pH 7.5, 100 mM NaCl, 0.1 mM EGTA, 1 mM MnCl2, 0.05% Tween 20) and injected at approximately 300 nM concentration directly to streptavidin coated surface for 100 sec or to reach immobilization level of biotin-PP1 corresponding to ~7000 RU. A blank immobilization was performed for one of the SA sensor chip surface to use as a reference.

Determining Steady-State Binding Constants of Small Molecules to elF2α Holophosphatase Complexes Using the Biotin-PP1 Surface
With minor deviations, the same procedure and conditions were used in all binding experiments. Small molecules were stored as 50 mM stock solutions in 100% DMSO. Prior to determining binding constants, serial dilutions of either 12 or 8 concentrations of the compounds were prepared in the running buffer in a 96-well plate. Prior to each compound dilution series the regulatory subunit, R15A or R15B, was diluted to 15 μM in the running buffer and captured on the biotin-PP1 surface, to form the holophosphatase complex on the sensor chip surface. Then, without regenerating the surface, the compound dilution series was injected onto the surface of the chip Sensorgrams were analyzed using the Biacore T200 evaluation software and the binding constants determined based on a steady-state model. Kinetic experiments are carried out using different concentrations of the compound and their respective equilibrium binding levels determined. These equilibrium response levels (Req) are plotted against concentration and fitted using a global fit, which is able to determine steady-state affinity constants, i.e. the concentration at 50% saturation is KD (Frostell-Karlsson et al., J. Med. Chem., 43, 1986-1992, 2000).

Mammalian Cell Culture
HeLa cells were cultured in Dulbecco's Modified Eagle's Media (DMEM) supplemented with penicillin, streptomycin, containing 5% and 10% fetal bovine serum (FBS), respectively. MEF cells were cultured in DMEM supplemented with penicillin, streptomycin, glutamine, 55 μM P-mercaptoethanol, 1× non-essential amino acids (Sigma-Adrich) and 10% FBS. Where indicated, cells were treated with 2.5 μg/ml tunicamycin, 1 mM DTT (Sigma-Adrich) and or the indicated compounds at the indicated concentrations.

Protein Analyses by Immunoblots
For immunoblots, HeLa cells (80,000 cells/ml) were plated in 12-well plates 24 hours before each experiment. Immediately after the indicated treatments, cells were lysed in 75 μl Laemmli Buffer, boiled at 95° C. for 5 minutes and sonicated. Proteins were separated and analysed as described (Tsaytler et al., Science, 332, 91-94, 2011) with the following antibodies: phospho-elf2α [pS52] and PPP1R15A/GADD34 (10449-1-AP; ProteinTech Group, 1/1000 dilution) and ATF4 (Sc-200 Santa Cruz).

Assessment of Cell Viability
Cells were plated in 24-well plates at a density of 15,000 (HeLa) or 12,000 cells/ml (MEFs) 24 hours prior to treatment. ER stress was elicited by addition of fresh media containing 2.5 μg/ml tunicamycin (Sigma-Aldrich). Compounds of Example 1 were dissolved in DMSO and added as indicated. DMSO was used as a mock treatment. Cell viability was assessed by measuring the reduction of WST-8 [2-(2-methoxy-4-nitrophenyl)-3-(4-nitrophenyl)-5-(2,4-disulfophenyl)-2H-tetrazolium] into formazan using Cell viability Counting Kit-8 (Dojindo) according to the supplier's recommendation, 48 hours after tunicamycin treatment.

Toxicity of the compounds is assessed using Cell viability Counting Kit-8 (Dojindo) or in a Incucyte (Essenbioscience) using both phase contrast and IncuCyte™ Cytotox Green Reagent.

Animal Studies

All animal care and procedures were performed in compliance with the regulation on the use of Animals in Research (UK Animals Scientific Procedures Act of 1986) with local ethical approval.

For studying the effect of a compound of Example 1 on weight, C3H/B6 mice were gavaged orally once a day with compounds of Example 1 and mice weight was recorded daily for 2 weeks.

To assess the efficacy of a compound of Example 1 in ameliorating a disease phenotype, 28-day old transgenic mice or littermate control were orally administered daily with a compound of Example 1 (2 mg/kg) or vehicle for a duration of 4 weeks. Disease progression was evaluated by weighting the mice during the treatment and by assessing their motor performances after 4 weeks of treatment.

To assess whether of a compound of Example 1 had the side effects of Guanabenz, mice (n>3) were gavaged orally with 10 mg/kg of compound or Guanabenz. Their activity was monitored 30 minutes following dosing. Guanabenz treated mice did not move 30 minutes after dosing, due to the hypotensive activity of Guanabenz, in contrast to mice treated with compound of Example 1 which were as active as untreated mice.

Eight weeks old HD-N171-82Q mice and their wild-type littermates were first habituated for 1 min on a static rotor and 1 min at constant speed (4 rpm). Habituation was repeated. The test session consisted of four trials with 15 min intervals in between. For each trial 5 mice were placed on an accelerating rotor (4 to 40 rpm) and the latency to fall was recorded, with a maximum limit for individual animal set at 300 s.

For treatment of a metabolic disorder, Db/db animals (n=5 per condition) were treated once a day with 1 mg/kg of compound of Example 1 for three weeks. Blood glucose levels were measured with a blood glucose meter (DSI) between 9 and 10 am. Data are mean+/−S.e.m.

Quantitative RT-PCR

RNA from brain was extracted in trizol (Life Technologies). RNA concentration was measured using a NANODROP1000 spectrophotometer (Thermo Fisher Scientific), and 1 µg was reverse transcribed to cDNA using a SuperScript reverse transcriptase (Life Technologies). Quantitative PCR with primers GAPDH (f): ACCACAGTCCATGCCATCAC, GAPDH (r): TCCACCACCCTGTTGCTGTA, PPP1R15A (f): CCTCCTGAAACTTGGGGACT; and PPP1R15A (r): GCTGTGATGTGGGATAAGCG was performed using SYBR® Select Master Mix (Ref 4472908, applied biosystems) on a Corbett Rotor-Gene version 6000. Expression of each gene was normalized to the housekeeping gene GAPDH and expressed as fold change calculated using Paffl equation.

DRG Cultures

Dorsal root ganglia (DRG) dissected from wild-type or Pmp22Tr-J (PMP22mutant) (Henry et al., Neuropathol. Exp. Neurol., 42, 688-706, 1983) embryo at 13.5 or development (E13.5) were cultured on collagen coated coverslips in neurobasal media supplemented with 4 g/l glucose, 2 mM L-glutamine, 2% B27 supplement and 50 ng/ml neuronal growth factor (NGF) for 7 days. To differentiate Schwann cells and induce myelination, the cultured DRGs were then maintained in C-media (MEM media supplemented with 4 g/l glucose, 2 mM L-glutamine, 10% FCS, 50 ng/ml NGF). The C-media was replaced every other day with freshly added 50 µg/ml ascorbic acid ±5 nM of compound of Example I and cultured for 14 days for myelination by the Schwann cells. The cultured DRGs were then fixed in 4% paraformaldehyde and immunostained with MBP (Rat Myelin basic protein, 1/250 dilution, ab73498).

The reference for the mice is Pubmed ID: 631386.

Biochemical Assay

Assay 1: A Selective PPP1R15B Inhibitor Selectively Binds to PPP1R15B-PP1 (FIG. 1)

Surface Plasmon Resonance (SPR) was used to measure the binding affinity of compounds to the PPP1R15A/B-PP1 phosphatase complex. Biotin acceptor peptide (BAP) was fused to the N-terminus of PP1γ, which enables the biotinylation of the BAP-tagged protein in Sf9 insect cells. After purification the BAP-PP1γ protein was captured on a streptavidin sensor chip (SA-chip, GE healthcare) to a response level of ~5.000 RU. Using controlled biotinylation enables orientated and uniform immobilization on the sensor chip surface. The PP1γ was then used to capture PPP1R15A/B and form a holophosphatase complex on the surface of the streptavidin chip. This complex can then be used to test binding of compounds. 10 µM PPP1R15A/B protein concentration was used to form the holophosphatase complex during a 80 s injection. After PPP1R15A/B has been captured a concentration series of a compound is injected over the surface of the chip, measuring the binding of the compound to the holophosphatase. After the concentration series (8 or 12 concentrations) is completed the surface is regenerated with 3 M NaCl and we can capture R15A/B again to form a fresh holophosphatase complex to measure a binding of another compound concentration series. Analysing the level of equilibrium binding as a function of concentration gives interaction affinities or steady-state binding affinity ($K_D$).

FIG. 1 shows the $K_D$ values for the compound of Example 1. A $K_D$ of 0.035 µM for PPP1R15B-PP1 and 1 µM for PPP1R15A-PP1 demonstrates that the compound of Example 1 selectively binds to the PP1R15B-PP1 complex but that binding is significantly less to the PPP1R15A-PP1 complex.

Assay 2: A Selective PPP1R15B Inhibitor Induces a Transient Phosphorylation of eIF2α in Cells, in the Absence of Stress (FIGS. 2A and B)

The selectivity of a compound of Example 1 was revealed using an in vitro binding assay with recombinant proteins. However, whilst a binding assay can be used to screen for selective compounds binding to PPP1R15B, the properties of a compound are not necessarily predicted by a binding assay. Thus, other assays are needed to assess whether the compound inhibits PPP1R15B function or not.

Human cells were treated with a PPP1R15B inhibitor and eIF2α phosphorylation was monitored over time. The inventors found that, in the absence of stress (under conditions where cells do not express PPP1R15A) treatment of cells with a compound of Example 1 induced eIF2α phosphorylation. This was manifested between 1 and 7.5 hours after addition of the compound of Example 1. However, at 10 hours following the addition of the compound of Example 1, eIF2α phosphorylation returned to basal levels. This suggested that there was an active eIF2α phosphatase at this time point. Indeed, the inventors noticed that PPP1R15A was induced at the late time points following addition of the compound of Example 1 (see Assay 3). The transient induction of eIF2α phosphorylation demonstrates that the compound is a selective inhibitor of PPP1R15B in cells. Furthermore, this establishes that the compound of Example 1 spares PPP1R15A. This assay can serve to identify other selective PPP1R15B inhibitors.

Assay 3: A Selective PPP1R15B Inhibitor Induces Expression of PPP1R15A in Cells (FIGS. 2A and B)

Cells and organisms usually have mechanisms to compensate for deficiencies. The inventors therefore considered whether cells might compensate for PPP1R15B inhibition by inducing PPP1R15A. It has been previously reported that PPP1R15A levels are increased in the liver of PPP1R15B knock-out mice (Harding et al., Proc. Natl. Acad. Sci. U.S.A., 106, 1832-1837, 2009). It is unknown whether this compensatory response is specific to the liver or if it can happen in cells or other tissues. Furthermore, prior to this study, it was unknown whether PPP1R15A induction can be observed upon pharmacological inhibition of PPP1R15B, as they were no selective inhibitors of PPP1R15B prior to this study. FIG. 2B demonstrates that cells treated with a compound of Example 1 were found to induce PPP1R15A. This property, induction of PPP1R15A, can be used as a method to screen for PPP1R15B inhibitors as compounds which induce PPP1R15A expression in cells will possess PPP1R15B inhibition properties. For example, an assay using a PPP1R15A gene or promoter fused to a reporter gene can be designed and developed in to a HTS screen to identify compounds that induce PPP1R15A.

Assay 4: A Selective PPP1R15B Inhibitor Protects Cells from Stress (FIG. 3)

FIG. 3 demonstrates that a selective PPP1R15B inhibitor protects cells from stress. Cells where stressed with Tunicamycin (2.5 ug/ml) in the presence of 0.2-5 □M of a compound of Example 1. Cell viability was measured 3 days after treatment.

The inhibitor of Example 1 protects cells from cytotoxic stress caused by tunicamycin. Cytoprotection against ER stress can be measured by a suitable assay. In this instance, cytoprotection was measured in HeLa cells in which ER stress was elicited by the addition of media containing tunicamycin, a drug that blocks N-glycosylation, thereby preventing protein folding and inducing the unfolded protein response. Cell viability was then detected in the presence and absence of a compound of Example 1 after a set period of time, by measuring the reduction of WST-8 into formazan using the standard cell viability kit Cell Viability Counting Kit-8 from Dojindo. Cytoprotection from ER stress was measured in terms of the percentage increase in viable cells (relative to control) after ER stress.

Assay 5: A Selective PPP1R15B Inhibitor Prolongs eIF2α Phosphorylation During Stress-Recovery (FIG. 4)

The inventors reasoned that a PPP1R15B inhibitor should prolong eIF2α phosphorylation following stress. To reveal this activity, it was crucial to search for conditions where PPP1R15A is not expressed, to avoid confounding effects. The inventors took advantage of the fast kinetic and reversibility of stress induction by DTT (Bertolotti et al., Nat. Cell. Biol., 2, 326-332, 2000; Jousse et al., 2003) and monitored eIF2α phosphorylation in cells following a 30 minute treatment with 1 mM DTT and a wash out. The inventors found that the decline in eIF2α phosphorylation that normally occurs after the DTT-washout is delayed and this occurred before any substantial induction of PPP1R15A. Thus, careful monitoring of the kinetic of eIF2α dephosphorylation in the early phase of a stress-recovery paradigm such as the one described here can be used to identify other PPP1R15B inhibitors.

Compound of Example 1 in Mice (FIG. 5) has a Good Tissue Distribution

Analysis of mouse tissues (plasma, brain, spinal cord, pancreas, liver) at different time following oral gavage of a compound of Example 1 revealed that the PPP1R15B inhibitor has an extensive tissue distribution and therefore demonstrates application in the treatment of various diseases and disorders affecting different organs.

Treatment of Mice with a Compound of Example 1 is not Toxic to Mice (FIG. 6)

Mice were treated with Example 1 and monitored closely to detect any clinical signs. It was found that mice treated for 2 weeks with up to 10 mg/mg once a day of a compound of Example 1 were undistinguishable from mice treated with placebo and the mice gained weight normally (FIG. 6). This establishes that PPP1R15B inhibition is not toxic. This was surprising and unanticipated as prior to this study one would have speculated that PPP1R15B inhibitors would be so deleterious that they would have no therapeutic potential.

Treatment of Mice with a Compound of Example 1 does not Cause the Side Effects Caused by Guanabenz (FIG. 7)

In humans, the adrenergic agonist activity of Guanabenz has side effects including drowsiness and coma at high doses (A. H. Hall, Ann Intern Med 102; 787-788; 1985). Due to of these side effects, Guanabenz is no longer used in human. It is anticipated that Guanabenz derivatives have the side effects of Guanabenz, associated with alpha-2 adrenergic activity. While the structure-activity relationship of Guanabenz to alpha-2 adrenergic receptor is not available, the inventors surprisingly found here that Example 1 is devoid of the side effects of Guanabenz, while structurally very similar.

Assay 6: Induction of PPP1R15A in a Mammal Following Treatment with a Compound of Example 1 (FIG. 8)

PPP1R15A induction was assessed by qPCR on total mRNA extracted from brains of mice treated with the indicated doses of compound of Example 1.

Similar to what had been seen in cells, it was found that mice induced PPP1R15A following a treatment with a compound of Example 1 and that this induction was dose-dependent. This explains why a selective PPP1R15B inhibitor is tolerated in mice: PPP1R15A induction dephosphorylates eIF2a, ensuring that the eIF2α phosphorylation which results from PPP1R15B inhibition by a compound of Example 1 is only transient. This is important because a persistent phosphorylation of eIF2α is detrimental. The induction of PPP1R15A in vivo by a PPP1R15B inhibitor is a pharmacodynamic parameter that can be used to evaluate the efficacy and potency of PPP1R15B inhibitors in mammals in pre-clinical or clinical studies.

A Compound of Example 1 Prevents a Disease in a Mammal (FIG. 9)

Increasing folding by inhibition of PPP1R15B has the potential to benefit a very broad range of human pathologies. To test this, the inventors looked at Huntington's disease (HD), a proteostasis disease caused by accumulation of a misfolded protein, mutant Huntingtin. There are some reports indicating that mutant Huntingtin induces the UPR (Duennwald and Lindquist, Gene & Development, 22, 3308-3319, 2008; Nishitoh et al., Genes & Development, 16, 1345-1355, 2002). However, the inventors' failure to detect PPP1R15A in models of Huntington's disease suggested that PPP1R15A is not a therapeutic target for HD. As HD has no cure to date, the inventors tested whether HD could be prevented by PPP1R15B inhibition. The inventors found that treatment of HD mice with 2 mg/kg of a compound of Example 1 prevented the motor performances impairment (FIG. 9). This demonstrates that PPP1R15B is a valid therapeutic target and that therefore PPP1R15B inhibition will be useful in the treatment and prevention of diseases.

As demonstrated here, to determine whether a disease can be prevented or ameliorated by PPP1R15B inhibition, mouse models or humans can be treated with tolerable doses of inhibitor. To attest target inhibition in vivo, markers of the PPP1R15B pathway can be monitored and used as pharmacodynamics markers. Such markers can be PPP1R15A, as shown here (FIG. 8) or any other on-pathway targets such as UPR or ISR markers (including but not restricted to eIF2α phosphorylation, CHOP, ATF4). As shown here with a compound of Example 1, a PPP1R15B inhibitor will be useful for therapies as long as it is safe and this is determined by the selectivity of the compound for PPP1R15B.

Myelination in Explants from Neuropathic Mice (FIG. 10).

CMT is a group of myelin neuropathies caused by mutations in a number of genes. Mutations in the peripheral myelin protein PMP22 are the most common causes of CMT. A mutation in PMP22 (Trembler-J) causes the misfolding of PMP22 and a disease in mice that resembles CMT in human due to defects in myelin in the peripheral nervous system. Explants from PMP22 mutant mice recapitulates the severe hypomyelination observed in the human diseases. The inventors found that treatment of dorsal root ganglia culture (DRG) from PMP22 mutant mice improved myelination. It has been previously found that the DRG cultures from mutant mice are useful models to predict therapeutic efficacy of compounds. Thus, the data present here demonstrate that the compound of Example 1 will be useful to treat a disease caused by mutation or overproduction of PMP22, such as CMT disease. The compound of Example 1 will also be useful in the treatment of other myelin disorders.

Assessment of PPP1R15B Efficacy in a Metabolic Disease (FIG. 11)

It is known that metabolic diseases such as diabetes, obesity, fatty liver disease, and atherosclerosis are associated with pathological ER stress and it is believed that pharmacological modulators of the UPR may have therapeutic benefit. As there were no PPP1R15B inhibitors available prior to this study it was unclear whether PPP1R15B could be a therapeutic target in metabolic diseases. The inventors tested this possibility and found that treatment of obese mice with a compound of Example 1 reduced the pathological high blood glucose in these mammals (FIG. 11). This demonstrates that treatment with a compound of Example 1 can ameliorate a metabolic disorder.

Having shown in one disease model that treatment with a compound of Example 1 is beneficial, it is evident that the compounds of the invention will be beneficial to other mammalian metabolic disorders such as diabetes, obesity, fatty liver disease, and atherosclerosis.

Example B

Protein Expression and Purification

MBP-R15A$^{325-636}$-His and MBP-R15B$^{340-698}$-His were expressed and purified as described before (Das et al. Science, 2015). cDNA encoding for human PP1γ was cloned into the baculovirus transfer vector pDW464 to add a N-terminal biotin acceptor peptide (BAP). The vector also encodes for the E. coli biotin holoenzyme synthetase (BirA), so that BAP-tagged proteins can be biotinylated (bio-PP1c) in vivo in Spodoptere frugiperda (Sf9) insect cells (Duffy et al., Anal. Biochem., 262, 122-128, 1998). The Bac-to-Bac baculovirus expression system (Thermo Fisher Scientific) was used to generate the recombinant bacmid DNA and Sf9 insect cells were used to amplify the viral stocks. The protein was produced using Sf9 insect cells in Insect-Xpress media (Lonza). bio-PP1c was purified by anion exchange chromotography on a HiTrap Q HP column (GE Healthcare), followed by gel filtration (HiLoad 16/600 Superdex 200 column, GE Healthcare. The proteins were analyzed on BOLT SDS-PAGE 4-12% Bis-Tris gels (Thermo Fisher Scientific) stained with InstantBlue (Expedeon) and the presence of a biotinylated PP1 was confirmed by a western blot using a Pierce High Sensitivity Streptavidin-HRP antibody (Thermo Fisher Scientific). This results in a partially pure protein, full purification is reached in later stages due to the high affinity and specificity of the biotin to streptavidin (on the SPR chip).

Surface Plasmon Resonance (SPR)

Capture of bio-GBZ or bio-PP1c on the SA Sensor Chip

A Biacore T200 (GE Healthcare) system was used for all experiments and biotinylated GBZ (bio-GBZ) {Tsaytler: 2011ji} or bio-PP1 was captured on a Sensor Chip SA (GE Healthcare). The streptavidin coated surface was activated by 1 minute injection with a solution of 50 mM NaOH and 1 M NaCl three times at a flow rate of 10 µl/min. bio-GBZ or bio-PP1c was diluted in the running buffer (50 mM Tris pH 7.5, 100 mM NaCl, 0.1 mM EGTA, 0.05% Tween 20, 0.1% DMSO) and injected at approximately 300 nM concentration at a flow rate of 10 µl/min directly to streptavidin coated surface to reach immobilization level of bio-GBZ or bio-PP1c corresponding to ~200 and 6000 RU, respectively. A blank immobilization was performed for one of the SA sensor chip surface to use as a reference.

Determining Steady-State Binding Constants of Small Molecules to R15 Holophosphatase Complexes Using the Bio-PP1c Surface Small molecules were stored as 50 mM stock solutions in 100% DMSO. Prior to determining binding constants, serial dilutions of either 12 or 8 concentrations of the compounds were prepared in the running buffer in a 96-well plate. Prior to each compound dilution series the regulatory subunit, MBP-R15A$^{325-636}$-His or MBP-R15B$^{340-698}$-His, was diluted to 10 µM in the running buffer and captured on the bio-PP1c surface at a flow rate of 30 µl/min for 1 minute to form the holophosphatase complex on the sensor chip surface. This was followed by 1 minute stabilization period, to wash off any unspecific binding. Then, without regenerating the surface, the compound dilution series was injected onto the surface of the chip at a flow rate of 30 µl/min for 1 minute, followed by 2 minutes dissociation time. After each dilution series the surface was regenerated using 3 M NaCl for 90 seconds. After regeneration, SPR responses generally returned to base levels and the bio-PP1c surface was ready for the next compound dilution series. In order to be able to correct for small variations in DMSO concentration between samples, eight solvent samples ranging from 0.06 to 8% DMSO were injected every 50th cycle. The flow cell temperature was 10° C.

Data Analysis

Sensorgrams were analyzed using the Biacore T200 evaluation software and the binding constants determined based on a steady-state model. Kinetic experiments are carried out using different concentrations of the compound and their respective equilibrium binding levels determined. These equilibrium response levels ($R_{eq}$) are plotted against concentration and fitted using a global fit, which is able to determine steady-state affinity constants, i.e. the concentration at 50% saturation is $K_D$. The $K_D$ values are shown in Table 1.

Measurement of Cytoprotection Against ER Stress

HeLa cells (40,000 cells/ml) were plated in a 96-well plate and treated with different concentrations (0-20 µM) of a compound as indicated in the presence of 250 ng/ml Tunicamycin for 72 hours. To monitor cell death 1/2000 dilution of the CellTox green dye (Promega) was added to the media. The growth of the cells was monitored over time and pictures taken every 2 hours with the IncuCyte ZOOM system and analysed by the IncuCyte ZOOM software (Essen BioScience). Table 1 shows the ability of the compounds to protect cells from cytotoxic stress caused by tunicamycin. Cytoprotection against ER stress can be measured by a suitable assay. In this instance, cytoprotection was measured in HeLa cells in which ER stress was elicited by the addition of media containing tunicamycin, a drug that blocks N-glycosylation, thereby preventing protein folding and inducing the unfolded protein response. Cell viability was then detected in the presence and absence of a compound listed in Table 1 after a set period of time, by monitoring cell growth over time.

Cytoprotection from ER stress was measured in terms of the percentage increase in viable cells (relative to control) after ER stress.

$$\text{Growth ratio} = \frac{\text{Phase confluency (\%) at } X \text{ hours}}{\text{Phase confluency (\%) at 0 hours}}$$

$$\% \text{ of dead cells} = \frac{\text{Green confluencey (\%) at } X \text{ hours}}{\text{Phase confluency (\%) at } X \text{ hours}} \times 100$$

EC50

EC50 were extrapolated from dose response experiments on cell death. Data from IncuCyte was plotted and analysed in Prism. The "% of cell death" for each data point. For each concentration there is a % of cell death vs time, the area under the curve was taken and plotted agains log conc=>EC50 (analysis in Prism).

Assessment of Translation Rates

Cells (90,000 cells/ml) were plated in 12-well plates, treated as indicated, labelled with 100 µCi/ml 35S-methionine (Hartmann Analytic) for 10 minutes at 37° C., washed with ice-cold PBS and lysed in 120 µl Laemmli Buffer. Lysates were boiled at 95° C. for 5 minutes, sonicated and resolved on 4-12% Bolt Bis-Tris Plus Gels (Thermo Fisher Scientific). Gels were then stained with InstantBlue (Expedeon) and analyzed by phosphorimaging and quantified using ImageJ.

By monitoring translation rates as described above, the activities of R15A, R15B and R15A/B inhibitors can be defined as follows (also shown in FIG. 12). An R15A inhibitor has no effect on translation in unstressed cells but prolongs translation attenuation following stress. A selective R15B inhibitor transiently attenuate protein synthesis because R15A compensates for the inhibition of R15B. An R15A/B inhibitor persistently inhibits protein synthesis.

Translation can be inhibited at many levels. To ensure that the R15A and B inhibitors are on-target, we monitor the levels of ATF4 in cells treated with compounds. A R15A/B inhibitor persistently induce eIF2α phosphorylation and eIF2α phosphorylation results in ATF4 translation. We show here that an A/B inhibitor indeed induces ATF4, confirming target engagement in cells.

TABLE 1

| Compound (E) | R15A | R15B | PP1 | Selective binding towards R15A or R15B (based on SPR) | Cytoprotection from Tm (compared to GNB) | ⇒ max at [µM] | Effect on cell death | ⇒ EC50 [µM] | Effect on translation | ⇒ Inhibits |
|---|---|---|---|---|---|---|---|---|---|---|
| 1 | 8.32 ± 0.14 | 7.33 ± 1.79 | 6.28 | R15AB | 0% | — | Yes | 4.9 | | R15A/B |
| 2 | 46.45 ± 18.28 | 9.222 | — | R15B | 0% | — | Yes | 7.709 | | R15B |
| 3 | 4.49 ± 1.47 | 0.149 | 10.32 | R15AB | 52% | 2.5 | Yes | 9.166 | Persistent | R15A/B |
| 4 | 0.457± 0.13 | 0.022± 0.02 | 331.6 | R15AB | 80% | 20 | No | — | Persistent/ Transient | R15A/B |
| 5 | 8.45 ± 0.41 | 2.67 ± 0.40 | 30.59 | R15AB | 48% | 5 | Yes | 9.458 | | R15A/B |
| 6 | 5.427± 1.10 | 9.094± 1.37 | — | R15AB | 61% | 2.5 | Yes | 9.653 | Persistent | R15NB |
| 7 | 10.20 ± 2.57 | 4.336± 2.35 | 12.98 | R15AB | 46% | 5 | Yes | 11.5 | | R15AB |
| 8 | 6.37 ± 1.03 | 11.34 | 10.59 ± 3.82 | R15AB | 0% | — | Yes | 11.68 | | R15AB |
| 9 | 13.6 ± 0.8 | 39.6 ± 5.9 | 14.7 ± 1.4 | R15A | 67% | 5 | Yes | 11.98 | | Off target |
| 10 | 0.391± 0.14 | 0.440± 0.09 | | R15AB | 85% | 0.625 | Yes | 12.52 | Persistent | R15A/B |
| 11 | 16.2 ± 2.1 | 13.38 ± 047 | | R15AB | 34% | 5 | Yes | 12.7 | | R15AB |
| 12 | 7.24 ± 0.5 | 11.7 ± 0.3 | 30.7 ± 1.5 | R15AB | 51% | 5 | Yes | 15.13 | Persistent | R15A/B |
| 13 | 4.624± 0.59 | 6.684± 2.343 | — | R15AB | 73% | 5 | Yes | 15.48 | Persistent | R15AB |
| 14 | 5.446± 1.48 | 5.434± 1.26 | — | R15AB | 100% | 2.5 | Yes | 18.4 | Persistent | R15A/B |
| 15 | 11.17 ± 2.18 | 7.681± 0.28 | 6.143 | R15AB | 46% | 10 | Yes | 19.5 | | R15A/B |

TABLE 1-continued

| Compound (E) | R15A | R15B | PP1 | Selective binding towards R15A or R15B (based on SPR) | Cytoprotection from Tm (compared to GNB) | ⇒ max at [µM] | Effect on cell death | ⇒ EC50 [µM] | Effect on translation | ⇒ Inhibits |
|---|---|---|---|---|---|---|---|---|---|---|
| 16 | 1.05 ± 0.013 | 0.035± 0.02 | — | R15B | 92% | 2.5 | Yes | 20.76 | Transient | R15B |
| 17 | 13.0 ± 0.5 | 18.1 ± 1.8 | 12.0 ± 0.8 | R15AB | 66% | 20 | No | — | (No) | (R15A/B) |
| 18 | 10.20 ± 1.62 | 4.850± 0.14 | 10.17 ± 0.14 | R15AB | 54% | 2.5 | Yes | 23.8 | | R15A/B |
| 20 | 5.666± 0.72 | 5.173± 0.69 | — | R15AB | 88% | 5 | Yes | 37.83 | | R15AB |
| 21 | 0.832 | 0.537 | (—) | R15AB | 41% | 20 | No | — | Transient | R15B |
| 22 | 7.622 | 12.35 | — | R15AB | 48% | 20 | No | — | | R15AB |
| 23 | 1.424 | 1.048± 0.32 | — | R15AB | 53% | 20 | No | — | | R15AB |
| 24 | 18.13 ± 7.57 | 18.67 | 6.267 | R15AB | 62% | 20 | No | — | | R15AB |
| 25 | 6.18 ± 3.31 | 9.223± 0.19 | 3.65 | R15AB | 54% | 20 | No | | | |
| 26 | 23.1 ± 0.9 | 30.0 ± 2.3 | | R15AB | 57% | 10 | No | | | R15AB |
| 27 | 10.56 | ? | — | | 57% | 10 | No | | | R15AB |
| 29 | 7.873± 1.48 | 4.057 | — | R15AB | 62% | 10 | No | — | | R15AB |
| 30 | 5.15 ± 1.7 | 12.3 ± 0.6 | 12.8 ± 0.08 | R15AB | 85% | 10 | No | | No | R15A/B |
| 31 | 11.1 ± 1.6 | 14.3 ± 0.7 | 12.6 ± 1.4 | R15AB | 99% | 10 | No | | No | R15A |
| 32 | 4.818± 0.26 | 17.28 | — | | 100% | 5 | No | — | Persistent | R15A/B |
| 34 | 17.2 ± 1.9 | 31.3 ± 2.0 | | R15AB | 57% | 5 | No | — | | R15AB |
| GBZ + 16 | | | | | 100% | 1.25 | Yes | 12.6 | Persistent | R15A/B |

The invention claimed is:

1. A compound of 2-(2,3,4-trichlorobenzylidene)hydrazine-1-carboximidamide or a salt thereof.

2. The compound of claim 1, wherein the compound is an E-isomer of the compound.

3. A pharmaceutical composition comprising (E)-2-(2,3,4-trichlorobenzylidene)hydrazine-1-carboximidamide or a pharmaceutically acceptable salt thereof, and a pharmaceutically acceptable excipient.

4. A method of treating a disorder of a subject, the method comprising administering to the subject a therapeutically effective amount of the compound according to claim 2, wherein the disorder is a disorder associated with accumulation of misfolded proteins or a proteostasis disorder, the disorder being alleviated by the inhibition of PPP1R15B or by the inhibition of both PPP1R15A and PPP1R15B.

5. The method of claim 4, wherein the disorder is selected from Alzheimer's disease, Parkinson's disease, Huntington's disease, ataxias, retinal degeneration, glaucoma, Amyotrophic Lateral Sclerosis, tauopathies, or a prion disease.

6. The method of claim 4, wherein the disorder is a polyglutamine disorder.

7. The method of claim 6, wherein the polyglutamine disorder is Huntington's disease.

8. The method of claim 4, wherein the disorder is a myelin disorder.

9. The method of claim 8, wherein the myelin disorder is selected from multiple sclerosis, Pelizaeus-Merzbacher disease, vanishing white matter disease, acute disseminated encephalomyelitis, periventricular leukomalacia, periventricular white matter injury, Tabes Dorsalis, Devic's disease, optic neuritis, progressive multifocal leukoencephalopathy, transverse myelitis, chronic inflammatory demyelinating polyneuropathy, anti-MAG peripheral neuropathy, adrenoleukodystrophy, adrenomyeloneuropathy, diffuse white matter injury, Guillain-Barre Syndrome, central pontine myelinolysis, inherited demyelinating diseases, or Charcot Marie Tooth disease.

10. The method of claim 4, wherein the disorder is a disorder associated with accumulation of misfolded proteins that arises from a mutation in a protein resulting in the protein's misfolding and mislocalization or trafficking defects.

11. The method of claim 10, wherein the disorder is selected from cystic fibrosis, congenital hypothyroid goitre, familial neurohypophyseal diabetes insipidus, procollagen biosynthesis disorders, hypercholesterolemia, alpha-1 antitrypsin deficiencies, lysomal disorders, retinis pigmentosa, or inflammatory bowel disease.

12. The method of claim 4, wherein the disorder is a metabolic disease.

13. The method of claim 12, wherein the metabolic disease is selected from diabetes, obesity, insulin resistance, hyperlipidemia, fatty liver disease, or atherosclerosis.

14. A method of treating a subject having a disease state alleviated by the inhibition of PPP1R15A and PPP1R15B, the method comprising administering to the subject a therapeutically effective amount of the compound according to claim 2 to thereby inhibit PPP1R15A and PPP1R15B.

15. A process for preparing the pharmaceutical composition of claim 3, the process comprising combining the (E)-2-(2,3,4-trichlorobenzylidene)hydrazine-1-carboximidamide or pharmaceutically acceptable salt thereof with a pharmaceutically acceptable excipient.

* * * * *